(12) United States Patent
Godfrey et al.

(10) Patent No.: US 7,101,663 B2
(45) Date of Patent: Sep. 5, 2006

(54) PCR METHOD

(75) Inventors: Tony E. Godfrey, Pittsburgh, PA (US); James D. Luketich, Pittsburgh, PA (US); Siva Raja, Pittsburgh, PA (US); Lori A. Kelly, Jeanette, PA (US); Sydney D. Finkelstein, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 519 days.

(21) Appl. No.: 10/090,326

(22) Filed: Mar. 4, 2002

(65) Prior Publication Data

US 2003/0017482 A1     Jan. 23, 2003

Related U.S. Application Data

(60) Provisional application No. 60/273,277, filed on Mar. 2, 2001.

(51) Int. Cl.
*C12Q 1/68*     (2006.01)
*C12P 19/34*     (2006.01)

(52) U.S. Cl. ............................................ 435/6; 435/91.2

(58) Field of Classification Search .................... 435/6, 435/91.1, 91.2; 536/23.1, 24.3, 24.33, 24.32
See application file for complete search history.

(56) References Cited

U.S. PATENT DOCUMENTS

| | | | |
|---|---|---|---|
| 5,314,809 A | 5/1994 | Erlich et al. | |
| 5,814,491 A | 9/1998 | Vijg et al. | |
| 5,837,442 A | 11/1998 | Tsang | |
| 5,843,761 A | 12/1998 | Barnett et al. | |
| 5,882,856 A | 3/1999 | Shuber | |
| 5,965,710 A | 10/1999 | Bodmer et al. | |
| 5,985,552 A * | 11/1999 | Howell et al. ................ | 435/6 |
| 6,033,854 A * | 3/2000 | Kurnit et al. ................ | 435/6 |
| 6,057,105 A * | 5/2000 | Hoon et al. .................. | 435/6 |
| 6,168,948 B1 * | 1/2001 | Anderson et al. .......... | 435/287.2 |
| 6,355,422 B1 * | 3/2002 | Liu et al. .................... | 435/6 |

FOREIGN PATENT DOCUMENTS

| | | |
|---|---|---|
| WO | WO 98/08970 A1 | 3/1998 |
| WO | WO 99/13104 | 3/1999 |

OTHER PUBLICATIONS

Boehringer Mannheim (PCR Applications Manual, Boehringer Mannheim Gmbh, Germany, 1995.*
Durmaz et al. Journal of Microbiological Methods. vol. 29, pp. 69-75, 1997.*
Takano et al. The Journal of Clinical endocrinology and Metabolism, vol. 84, No. 3, pp. 951-955, 1999.*
Gerhard et al. Journal of Clinical oncology, vol. 12, No. 4, pp. 725-729, Apr. 1994.*
Brown et al. Surgery, vol. 117, No. 1, pp. 96-101, 1995.*
Nakanishi et al., Int. J. Caner 89, 411-417 (2000).*
GenBank Accession No. XM_012777 (SEQ ID No.: 1).
TaqMan One-Step RT-PCR Master Mix Reagents Kit, Protocol, *PE Biosystems* 1999.
Raja, S., Luketich, J.D., Ruff, D.W. and Godfrey, T.E., "Increased Sensitivity of One-Tube, Quantitative RT-PCR," *Bio Techniques* vol. 29, No. 4:702-706 (Oct. 2000).
ABI PRISM 7700 Sequence Detection System, User Bulletin #2, "Relative Quantitation of Gene Expression," *Applied Biosystems* (1997/updated Oct. 2001).
ABI PRISM 7700 Sequence Detection System, User Bulletin #5, "Multiplex PCR with TaqMan VIC Probes," *Applied Biosystems* (1998/updated Jan. 2001).
DeLong, E.R., DeLong, D.M. and Clarke-Pearson, D.L., "Comparing the areas under two or more correlated receiver operating characteristic curves: a nonparametric approach," *Biometrics* 44(3):837-845, 1988.
Gibson, U.E., Heid, C.A. and Williams, P.M. A novel method for real time quantitative RT-PCR, *Genome Res*, 6:995-1001, 1996.
Heid, C.A., Stevens, J., Livak, K.J. and Williams, P.M., "Real time quantitative PCR," *Genome Res*, 6:986-994, 1996.
Davidson, A.C. and Hinkley, D.V., "Bootstrap Methods and Their Application," Cambridge, United Kingdom: *Cambridge University Press*, 1997.
Battaglia, M., Pedrazzoli, P., Palermo, B., Lanza, A., Bertonlini, F., Gibelli, N., Da Prada, G.A., Zambelli, A., et al. "Epithelial tumour cell detection and the unsolved problems of nested RT-PCR: a new sensitive one step method without false positive results," *Bone Marrow Transplant* 22:693-698, 1998.
Collins, C., Rommens, J.M., Kowbel, D., Godfrey, T., Tanner, M., Hwang, S-I., Polikoff, D., Nonet, G., et al. Positional cloning of ZNF217 and NABC1: Genes amplified at 20q13.2 and overexpressed in breast carcinoma. *Proc. Natl. Acad Sci. USA* 95:8703-8708, 1998.
Fitzgerald RC, Triadafilopoulos G. "Recent Developments in the Molecular Characterization of Barrett's Esophagus." *Dig. Dis.* 16:63-80, 1998.

(Continued)

*Primary Examiner*—Kenneth R. Horlick
(74) *Attorney, Agent, or Firm*—Jesse A. Hirshman

(57) ABSTRACT

A method for balancing multiplexed PCR methods is provided. In the method, two or more sequential temporal PCR stages are used to effectively separate two or more PCR reactions in a single tube as an alternative to primer limiting to modulate the relative rate of production of a first amplicon by a first primer set and a second amplicon by a second primer set during the first and second amplification stages. Also provided are rapid RT-PCR methods that find particular use in intraoperative diagnoses and prognoses, for instance in diagnosing malignant esophageal adenocarcenoma by determining expression levels of carcinoembryonic antigen (CEA) in sentinel lymph nodes.

70 Claims, 18 Drawing Sheets

OTHER PUBLICATIONS

Liefers, G.-J., Cleton-Jansen, A.M., Corneli, J.H., et al., R.A. "Micrometastases and survival in stage II colorectal cancer" [see comments]. *N. Engl. J. Med.*, 339: 223-228, 1998.

Shivers, S.C., Wang, X., Li, W., Joseph, E., Messina, J., Glass, L.F., DeConti, R., Cruse, C.W., Berman, C., Fenske, N.A., Lyman, G.H. and Reintgen, D.S., "Molecular Staging of Malignant Melanoma: Correlation with Clinical Outcome," *JAMA*, 280: 1410-1415, 1998.

Bostick, P.J., Morton, D.L., Turner, R.R., Huynh, K.T., Wang, H.J., Elashoff, R., Essner, R. and Hoon, D.S., "Prognostic Significance of Occult Metastases Detected by Sentinel Lymphadenectomy and Reverse Transcriptase-Polymerase Chain Reaction in Early-Stage Melanoma Patients," *J. Clin. Oncol.*, 17: 3238-3244, 1999.

Godfrey, T.E., Kim, S.-H., Chavira, M., Ruff, D.W., Warren, R.S., Gray, J.W. and Jensen, R.H. "Quantitative mRNA expression analysis from formalin-fixed, paraffin-embedded tissues using 5' nuclease quantitative RT-PCR," *J. Mol. Diagn.*, 2:84-91, 2000.

Heagerty, P.J., Lumley, T. and Pepe, M.S., "Time-Dependent ROC Curves for Censored Survival Data and a Diagnostic Marker," *Biometrics*, 56(2):337-845, 2000.

Tassone, F., Hagerman, R.J., Taylor A.K., Gene, L.W., Godfrey, T.E., and Hagerman, P.J., "Elevated Levels of FMR1 mRNA in carrier males: a new mechanism of involvement in the fragile-X syndrome," *Am. J. Hum. Genet.*, 66:6-15, 2000.

Weiser MR, Montgomery LL, Susnik B, Tan LK, Borgen PI, Cody HS. "Is routine intraoperative frozen-section examination of sentinel lymph nodes in breast cancer worthwhile?" *Ann Surg Oncol.*; 7:651-655, 2000.

Godfrey TE. Raja S. Finkelstein SD, Kelly LA, Gooding W, Luketich JD. "Quantitative RT-PCR Predicts Disease Recurrence in lymph Node-Negative Esophagus Cancer Patients." *Proceedings from the 2001 Annual Meeting of the American Association of Cancer Researchers* 42. Mar. 1, 2001.

Miyake, Y., Fujiwara, Y., Ohue, M., Yamamoto, H., Suita, Y., Tomita, N., Sekimoto, M., Shiozaki, H. and Monden, M. "Quantification of micrometastases in lymph nodes of colorectal cancer using real-time fluorescence polymerase chain reaction," *Int. J. Oncol.* 16(2):289-293 2000.

Bercovich D et al. Quantitative ratio of primer pairs and annealing temperature affecting PCR products in duplex amplification. Biotechniques. Oct. 1999;27(4):762-4, 766-8, 770.

Dessau RB et al. Coronaviruses in spinal fluid of patients with acute monosymptomatic optic neuritis. Acta Neurol Scand. Aug. 1999;100(2):88-91.

Harris E at al. Typing of dengue viruses in clinical specimens and mosquitoes by single-tube multiplex reverse transcriptase PCR. J Clin Microbiol. Sep. 1998;36(9):2634-9.

Oshima A, et al. Cloning, sequencing, and expression of cDNA for human beta-glucuronidase, Proc Natl Acad Sci U S A. Feb. 1987;84(3):685-9.

Viehmann S et al. Multiplex PCR—a rapid screening method for detection of gene rearrangements in childhood acute lymphoblastic leukemia. Ann Hematol. Apr. 1999;78(4):157-62.

Wu DY et al. The effect of temperature and oligonucleotide primer length on the specificity and efficiency of amplification . . . DNA Cell Biol. Apr. 1991;10(3):233-8.

Ylitalo N et al. Detection of genital human papillomavirus by single-tube nested PCR and type-specific oligonucleotide hybridization. J Clin Microbiol. Jul. 1995;33(7):1822-8.

\* cited by examiner

Fig. 5

(SEQ ID NO: 1)

```
   1 ctcagggcag agggaggaag gacagcagac cagacagtca cagcagcctt gacaaaacgt
  61 tcctggaact caagctcttc tccacagagg aggacagagc agacagcaga gaccatggag
 121 tctccctcgg cccctcccca cagatggtgc atccctggc agaggctcct gctcacagcc
 181 tcacttctaa ccttctggaa cccgcccacc actgccaagc tcactattga atccacgccg
 241 ttcaatgtcg cagaggggaa ggaggtgctt ctacttgtcc acaatctgcc ccagcatctt
 301 tttggctaca gctggtacaa aggtgaaaga gtggatggca accgtcaaat tataggatat
 361 gtaataggaa ctcaacaagc taccccaggg cccgcataca gtggtcgaga gataatatac
 421 cccaatgcat ccctgctgat ccagaacatc atccagaatg acaggatt ctacaccota
 481 cacgtcataa agtcagatct tgtgaatgaa gaagcaactg ccagttccg ggtatacccg
 541 gagctgccca agcctccat tccagcaac aactccaaac ccgtggagga caaggatgct
 601 gtggccttca cctgtgaacc tgagactcag gacgcaacct acctgtggtg ggtaaacaat
 661 cagagcctcc cggtcagtcc caggctgcag ctgtccaatg caacaggac cctcactcta
 721 ttcaatgtca aagaaatga cacagcaagc tacaaatgtg aaacccagaa cccagtgagt
 781 gccaggcgca gtgattcagt catcctgaat gtcctctatg cccggatgc ccccaccatt
 841 tcccctctaa acacatctta cagatcaggg aaaatctga acctctcctg ccacgcagcc
 901 tctaacccac ctgcacagta ctcttggttt gtcaatggga cttccagca atccacccaa
 961 gagctcttta tccccaacat cactgtgaat aatagtggat cctatacgtg ccaagcccat
1021 aactcagaca ctggcctcaa taggaccaca gtcacgacga tcacagtcta tgcagagcca
1081 cccaaaccct tcatcaccag caacaactcc aaccccgtgg aggatgagga tgctgtagcc
1141 ttaacctgtg aacctgagat tcagaacaca acctacctgt ggtgggtaaa taatcagagc
1201 ctcccggtca gtcccaggct gcagctgtcc aatgacaaca ggaccctcac tctactcagt
1261 gtcacaagga atgatgtagg accctatgag tgtggaatcc agaacaaatt aagtgttgac
1321 cacagcgacc cagtcatcct gaatgtcctc tatggcccag acgaccccac catttccccc
1381 tcatacacct attaccgtcc agggggtgaac ctcagcctct cctgccatgc agcctctaac
1441 ccacctgcac agtattcttg gctgattgat gggaacatcc agcaacacac acaagagctc
1501 tttatctcca acatcactga agaacagcg gactctata cctgccaggc caataactca
1561 gccagtggcc acagcaggac tacagtcaag acaatcacag tctctgcgga gctgcccaag
1621 ccctccatct ccagcaacaa ctccaaaccc gtggaggaca aggatgctgt ggccttcacc
1681 tgtgaacctg aggctcagaa cacaacctac ctgtggtggg taaatggtca gagcctccca
1741 gtcagtccca ggctgcagct gtccaatggc aacaggaccc tcactctatt caatgtcaca
1801 agaaatgacg caagagccta tgtatgtgga atccagaact cagtgagtgc aaaccgcagt
1861 gacccagtca cctggatgt cctctatggg ccggacaccc catcatttc cccccagac
1921 tcgtcttacc tttcgggagc gaacctcaac ctctcctgcc actcggcctc taacccatcc
1981 ccgcagtatt cttggcgtat caatgggata ccgcagcaac acacacaagt tctctttatc
2041 gccaaaatca cgccaaataa taacgggacc tatgcctgtt ttgtctctaa cttggctact
2101 ggccgcaata attccatagt caagagcatc acagtctctg catctggaac ttctcctggt
2161 ctctcagctg ggccactgt cggcatcatg attggagtgc tggttggggt tgctctgata
2221 tagcagccct ggtgtagttt cttcatttca ggaagactga cagttgtttt gcttcttcct
2281 taaagcattt gcaacagcta cagtctaaaa ttgcttcttt accaaggata tttacagaaa
2341 agactctgac cagagatcga gaccatccta gccaacatcg tgaaacccca tctctactaa
2401 aaatacaaaa atgagctggg cttggtggcg cgcacctgta gtcccagtta ctcgggaggc
2461 tgaggcagga gaatcgcttg aacccgggag gtggagattg cagtgagccc agatcgcacc
2521 actgcactcc agtctggcaa cagagcaaga ctccatctca aaagaaaag aaaagaagac
2581 tctgacctgt actcttgaat acaagtttct gataccactg cactgtctga gaatttccaa
2641 aactttaatg aactaactga cagcttcatg aaactgtcca ccaagatcaa gcagagaaaa
2701 taattaattt catgggacta aatgaactaa tgaggattgc tgattcttta aatgtcttgt
2761 ttcccagatt tcaggaaact tttttcttt taagctatcc acagcttaca gcaatttgat
2821 aaaatatact tttgtgaaca aaaattgaga catttacatt ttctccctat gtggtcgctc
2881 cagacttggg aaactattca tgaatattta tattgtatgg taatatagtt attgcacaag
2941 ttcaataaaa atctgctctt tgtatgacag aatac
```

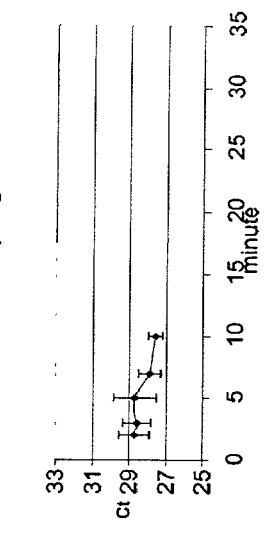
Fig. 12A
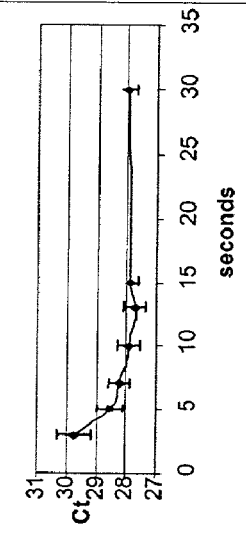
Fig. 12B
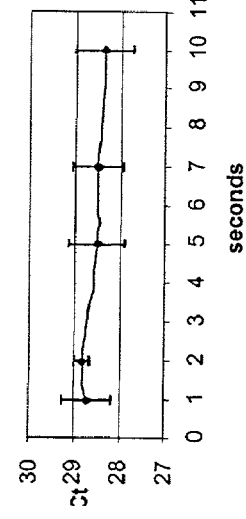
Fig. 12C
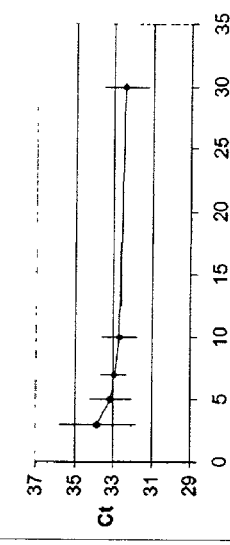
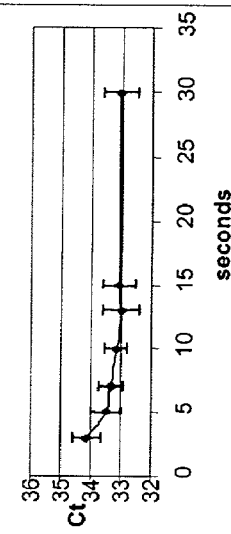
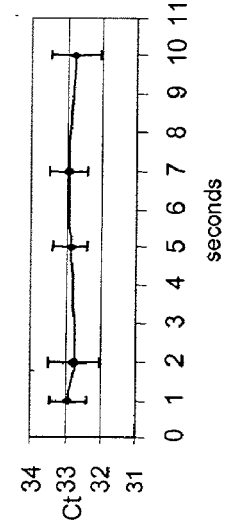

PCR METHOD

CROSS-REFERENCE TO RELATED APPLICATIONS

This application claims priority under 35 U.S.C. § 119(e) to U.S. Pat. application Ser. No. 60/273,277, filed Mar. 2, 2001, which is incorporated herein by reference in its entirety.

STATEMENT REGARDING FEDERALLY SPONSORED RESEARCH & DEVELOPMENT

This invention was made with government support under Grant No. CA90665-01, awarded by the National Institutes of Health. The government has certain rights in this invention.

BACKGROUND

This Application discloses a rapid PCR method, with particular focus on a rapid multiplex QRT-PCR method and related compositions and apparatuses.

Polymerase chain reaction (PCR) is a powerful tool in the field of molecular biology. This technique allows for replicating/amplifying trace amounts DNA fragments into quantities that can be analyzed in a meaningful way. As such this technology has been adapted to molecular biological applications like DNA sequencing, DNA fingerprinting, etc. Additionally, this method has the ability to detect specific DNA fragments in samples, whose presence may reflect a pathological state. Therefore, this method is finding new applications in the field of molecular diagnostics. Furthermore with the development of real-time quantitative PCR (QPCR), this technology has become more reliable as well as amenable to automation. Currently, this technology is used for the detection of viral and bacterial pathogens in clinical samples and for the detection of cancer cells in patients with a history of leukemias (and other cancers such as those that arise in the breast, lung, colon, esophagus and skin).

PCR in molecular diagnostics, despite its advantages, has several shortcomings. Often, this is a technique that is dependent on the technical expertise of the operator. Additionally, it is also very prone to contamination. The combination of these two above-mentioned factors results in false negative and false positive results respectively. Therefore, there is a need to incorporate internal controls along with the target of interest as well as automate the process to ensure operation within a closed system (to eliminate contamination). The incorporation of controls involves the amplification of several different sets of DNA fragments in addition to the target of interest. These controls provide information about the quality of the samples being analyzed as well as that of the assay in any given run. For technical reasons, analyzing multiple DNA targets within a sample in the same reaction tube through PCR (known as multiplexing) does not work well when the targets are not present in similar abundance at the beginning of the reaction. Historically, investigators have attempted to overcome this by limiting the primers in the PCR reaction. This approach is based on the idea that by limiting the reagents in one reaction, it stops the reaction at a point after adequate amplification has occurred for that target but before inhibition of amplification of other sequences. Though this method can increase the difference in initial abundance between the two targets that will still result in the successful amplification of both targets, it does not allow for the detection of a rare target in the milieu of a second target that is several orders of magnitude more abundant. Furthermore, when a rapid QPCR assay is called for, decreasing the primer concentration also worsens quantitation.

A further limitation of current PCR technologies is the time it takes to perform PCR diagnoses. Typical PCR reactions take hours, not minutes. As described below, decreasing the time it takes to carry out a PCR reaction is desirable for many reasons. Therefore, there is a need for an automated PCR based point of care molecular diagnostic system, especially a rapid, multiplexed (RT-)PCR assay.

SUMMARY OF THE INVENTION

Rapid and robust PCR and RT-PCR methods are provided that permit execution of a complete PCR reaction in minutes, not hours, permitting use of PCR in intraoperative diagnoses, for example, but without limitation, for detecting micrometastases in sentinel lymph nodes, as an superior alternative to, or in addition to typical pathological methods such as histopathological examination of lymph nodes.

Also provided is an alternative to primer limiting as a method for balancing a multiplex PCR reaction, especially quantitative PCR amplifications, with particular usefulness in QRT-PCR reactions. This method finds particular use when one target sequence to be amplified is far less prevalent than another to be amplified in the same reaction mixture. The method comprises the step of conducting a PCR amplification on a DNA sample in a PCR reaction mixture in a first amplification stage and a second amplification stage. The PCR amplification of the second amplification stage is conducted under different reaction conditions than the PCR amplification of the first amplification stage to modulate the relative rate of production of a first amplicon by a first primer set and a second amplicon by a second primer set during the first and second amplification stages. Additional amplification stages may be added.

Two non-limiting specific embodiments of this method are disclosed. In the first embodiment, the second primer set is added to the reaction mixture at the beginning of the second amplification stage, thereby limiting the physical presence of the second primer set during the first stage. In this method, the rarer target sequence preferably is amplified before the less-rare sequence which typically is a control, such as β-gus or 18SrRNA sequences.

In the second embodiment, the PCR reaction mixture includes the first primer set having a first effective Tm and the second primer set having a second effective Tm different from the first effective Tm. The relative rate of production of the first amplicon by the first primer set and the second amplicon by the second primer set during the first and second amplification stages is modulated by conducting the annealing step of the first amplification stage at a different temperature than the annealing step of the second amplification stage. In this second embodiment the annealing temperature for the second amplification stage may be higher or lower than the annealing temperature for the first amplification stage.

Also provided is a rapid RT-PCR method that is based upon the finding that the reverse transcription reaction of the RT-PCR method need not be performed for longer than about 10 minutes, and preferably only for about two minutes. This rapid step, when coupled with a rapid PCR procedure conducted sequentially with the RT reaction in the same reaction vessel as the RT reaction, permits intraoperative use of the RT-PCR reaction, especially when the entire process is automated.

Each of the above-described PCR and RT-PCR process find special utility in their use in quantitative PCR methods, such as QPCR and QRT-PCR, which are typically monitored during the PCR amplification by the accumulation of, or loss of, a fluorescent reporter, for instance by the use of TAQ-MAN and molecular beacon probes.

The above-described methods may be automated in a cartridge-based system, thereby reducing human error in the methods, as well as the potential for contamination. In an automated system, reagents for the various reactions are added sequentially according to a programmed sequence. A cartridge, for use in an automated system, for performing the described methods also is provided.

Also provided are specific uses for the rapid PCR methods described herein. In one embodiment, an intraoperative PCR diagnostic method is provided that includes the steps of: obtaining a tissue sample from a patient in an operation; analyzing the sample according to one of the above-described PCR methods; determining if expression of an indicator transcript exceeds a threshold level; and continuing the operation in a manner dictated by results of the analyzing step. In another embodiment, a method for rapid detection of a malignancy is provided that includes the steps of: obtaining nucleic acid from a tumor biopsy; performing a PCR method specific to an indicator transcript on the nucleic acid according to one of the above-described PCR methods; and determining if expression of the indicator transcript exceeds a threshold level, thereby indicating a malignancy.

In an additional embodiment, a method for rapid detection of metastasized adenocarcenoma of the esophagus is provided. The method includes the steps of: obtaining RNA from a sentinel lymph node; performing a quantitative RT-PCR method specific to CEA on the RNA according to any one of the above-described PCR methods; and determining if expression of CEA exceeds a threshold level.

Lastly, also provided are specific novel oligonucleotide primers useful in the detection of sequences specific to CEA and tyrosinase genes, as well as β-gus and 18SrRNA sequences.

BRIEF DESCRIPTION OF THE DRAWINGS

FIG. 5 provides the CEA nucleotide sequence, GenBank Accession No. $XM_{13}012777$ (SEQ ID NO:1).

FIGS. 12A–C show the optimization of the rapid QRT-PCR assay for β-gus and CEA. FIG. 12A compares the Ct values for assays with different denaturation times and a 30 second extension time. FIG. 12B compares the effect of different extension times on the Ct value when the denaturation time is held constant at 10 seconds. FIG. 12C demonstrates the effect of different RT times when the PCR conditions are constant.

DETAILED DESCRIPTION

Figure 1:
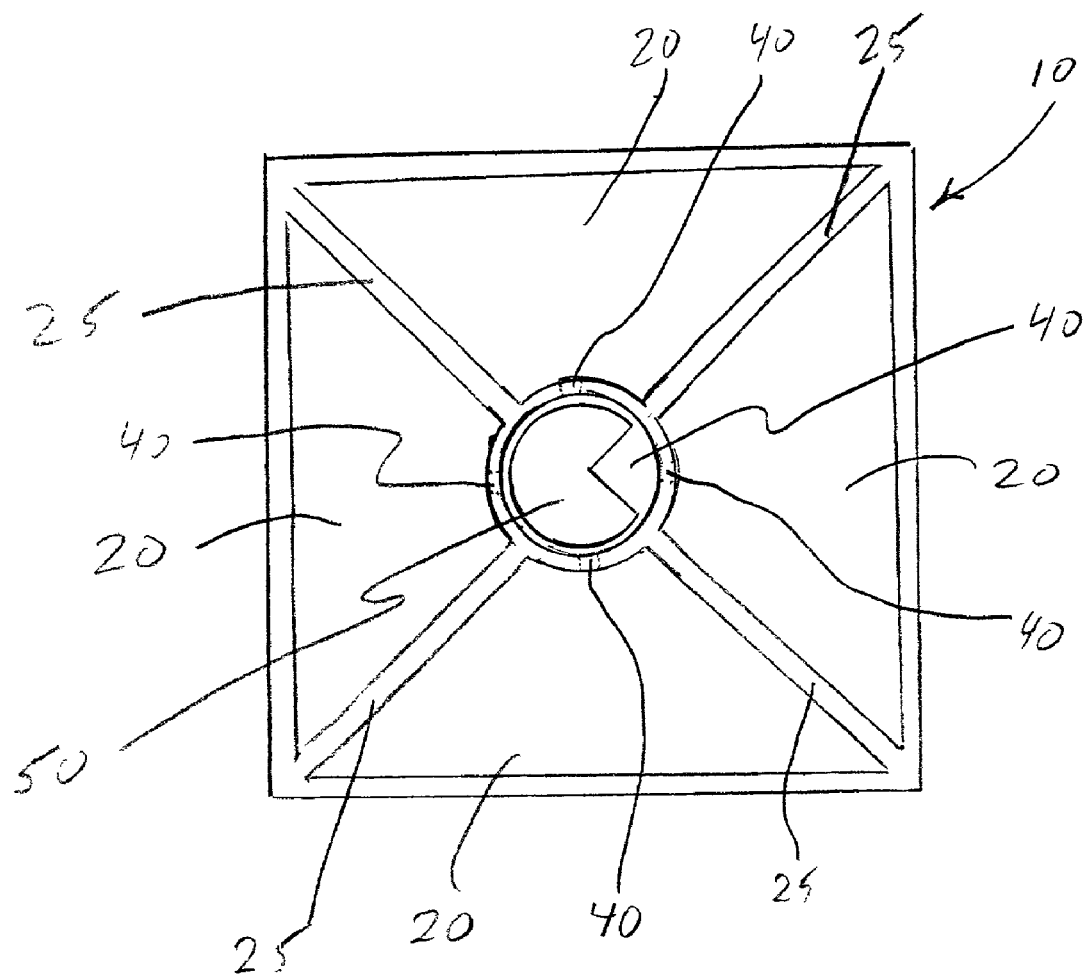
FIG. 1 is a schematic drawing of a cartridge according to one embodiment of the present invention.

Provided are improved PCR methods that permit rapid cycling and/or improved sensitivity for PCR-based molecular diagnostics, especially with respect to quantitative PCR methods, including QRT-PCR. These improved methods permit PCR to be used intraoperatively, and also are useful in detecting rare nucleic acid species, even in multiplexed PCR reactions that concurrently detect a more prevalent control nucleic acid.

A typical PCR reaction includes multiple amplification steps, or cycles that selectively amplify a target nucleic acid species. A full description of the PCR process, and common variations thereof, such as quantitative PCR (QPCR), real-time QPCR, reverse transcription PCR (RT-PCR) and quantitative reverse transcription PCR (QRT-PCR) is beyond the scope of this disclosure and these methods are well-described in the art and have been broadly commercialized. A typical PCR reaction includes three steps: a denaturing step in which a target nucleic acid is denatured; an annealing step in which a set of PCR primers (forward and backward primers) anneal to complementary DNA strands; and an elongation step in which a thermostable DNA polymerase elongates the primers. By repeating this step multiple times, a DNA fragment is amplified to produce an amplicon, corresponding to the target DNA sequence. Typical PCR reactions include 30 or more cycles of denaturation, annealing and elongation. In many cases, the annealing and elongation steps can be performed concurrently, in which case the cycle contains only two steps.

The lengths of the denaturation, annealing and elongation stages may be any desirable length of time. However, in attempting to shorten the PCR amplification reaction to a time suitable for intraoperative diagnosis, it has been found that the lengths of these steps can be in the seconds range, rather than the minutes range. Specifically, with certain new thermal cyclers being capable of generating a thermal ramp rate ($\delta T$) of at least about 5° C. per second, PCR amplifications in 20 minutes are possible. As used herein, the times provided for each step of the PCR cycle does not include ramp times. The denaturation step may be conducted for times of one second or less. In fact, some thermal cyclers do not have settings for "0 seconds" which may be the optimal duration of the denaturation step. That is, it is enough that the thermal cycler reaches the denaturation temperature. The annealing and elongation steps are optimally less than 10 seconds each, and when conducted at the same temperature, the combination annealing/elongation step may be less than 10 seconds.

As described herein, each cycle may be shortened considerably without substantial deterioration of production of amplicons by using substantially increased primer concentrations, typically greater than about 400 nM, and often greater than about 800 nM, though the optimal concentration of primers will vary somewhat from assay-to-assay. Sensitivity of RT-PCR assays may be enhanced by the use of a sensitive Reverse Transcriptase enzyme (described herein) and/or high concentrations of Reverse Transcriptase primer to produce the initial target PCR template.

The specificity of any given PCR reaction relies heavily, but not exclusively, on the identity of the primer sets. The primer sets are pairs of forward and reverse oligonucleotide primers that anneal to a target DNA sequence to permit amplification of the target sequence, thereby producing a target sequence-specific amplicon. As used herein, a "derivative" of a specified oligonucleotide is an oligonucleotide that binds to the same target sequence as the specified oligonucleotide and amplifies the same target sequence to produce essentially the same amplicon as the specified oligonucleotide but for differences between the specified oligonucleotide and the derivative. The derivative may differ from the specified oligonucleotide by insertion, deletion and/or substitution of any residue of the specified sequence so long as the derivative substantially retains the characteristics of the specified sequence in its use for the same purpose as the specified sequence.

As used herein, "reagents" for any enzymatic reaction mixture, such as a reverse transcription and PCR reaction mixture, are any compound or composition that is added to the reaction mixture including, without limitation, enzyme(s), nucleotides or analogs thereof, primers and primer sets, buffers, salts and co-factors. As used herein, unless expressed otherwise, "reaction mixture" includes all necessary compounds and/or compositions necessary to perform that enzymatic reaction, even if those compounds or compositions are not expressly indicated.

Multiplexed PCR assays may be optimized, or balanced, by time-shifting the production of amplicons, rather than by manipulating primer concentrations. This may be achieved by using two primer sets, each primer set having a different Tm so that a two-stage PCR assay can be performed, with different annealing and/or elongation temperatures for each stage to favor the production of one amplicon over the other. This time and temperature shifting method permits optimal balancing of the multiplex reaction without the difficulties faced when manipulation of primer concentrations is used to balance the reaction. This technique is especially useful in a multiplex reaction where it is desirable to amplify a rare cDNA along with a control cDNA, such as the CEA/β-GUS example shown below.

A quantitative reverse transcriptase polymerase chain reaction (QRT-PCR) method is provided for rapidly and accurately detecting low abundance RNA species in a population of RNA molecules (for example, and without limitation, total RNA or mRNA), including the steps of: a) incubating an RNA sample with a reverse transcriptase and a high concentration of a target sequence-specific reverse transcriptase primer under conditions suitable to generate cDNA; b) subsequently adding suitable polymerase chain reaction (PCR) reagents to the reverse transcriptase reaction, including a high concentration of a PCR primer set specific to the cDNA and a thermostable DNA polymerase to the reverse transcriptase reaction, and c) cycling the PCR reaction for a desired number of cycles and under suitable conditions to generate PCR product ("amplicons") specific to the cDNA. By temporally separating the reverse transcriptase and the PCR reactions, and by using reverse transcriptase-optimized and PCR-optimized primers, excellent specificity is obtained. The reaction is conducted in a single tube (all tubes, containers, vials, cells and the like in which a reaction is performed may be referred to herein, from time to time, generically, as a "reaction vessel"), removing a source of contamination typically found in two-tube reactions. The high concentration primers permit very rapid QRT-PCR reactions, typically on the order of 20 minutes from the beginning of the reverse transcriptase reaction to the end of a 40 cycle PCR reaction. The realization of such a rapid QRT-PCR experiment is assisted by the availability of thermal cycling devices capable of generating a thermal ramp rate (δT) of at least about 5° C. per second.

The reaction c) may be performed in the same tube as the reverse transcriptase reaction by adding sufficient reagents to the reverse transcriptase (RT) reaction to create good, or even optimal conditions for the PCR reaction to proceed. A single tube may be loaded, prior to the running of the reverse transcriptase reaction, with: 1) the reverse transcriptase reaction mixture, and 2) the PCR reaction mixture to be mixed with the cDNA mixture after the reverse transcriptase reaction is completed. The reverse transcriptase reaction mixture and the PCR reaction mixture may be physically separated by a solid, or semi-solid (including amorphous, glassy substances and waxy) barrier of a composition that melts at a temperature greater than the incubation temperature of the reverse transcriptase reaction, but below the denaturing temperature of the PCR reaction. The barrier composition may be hydrophobic in nature and forms a second phase with the RT and PCR reaction mixtures when in liquid form. One example of such a barrier composition is wax beads, commonly used in PCR reactions, such as the AMPLIWAX PCR GEM products commercially available from Applied Biosystems of Foster City, Calif. and the STRATASPHERE Magnesium Wax Beads, commercially available from Stratagene of La Jolla, Calif.

Alternatively, the separation of the reverse transcriptase and the PCR reactions may be achieved by adding the PCR reagents, including the PCR primer set and thermostable DNA polymerase, after the reverse transcriptase reaction is completed. Preferably the PCR reagents, are added mechanically by a robotic or fluidic means to make sample contamination less likely and to remove human error.

The products of the QRT-PCR process may be compared after a fixed number of PCR cycles to determine the relative quantity of the RNA species as compared to a given reporter gene. One method of comparing the relative quantities of the products of the QRT-PCR process is by gel electrophoresis, for instance, by running the samples on a gel and detecting those samples by one of a number of known methods including, without limitation, Southern blotting and subsequent detection with a labeled probe, staining with ethidium bromide and incorporating fluorescent or radioactive tags in the amplicons.

However, the progress of the PCR reaction typically is monitored by analyzing the relative rates of amplicon production for each PCR primer set. Monitoring amplicons production may be achieved by a number of processes, including without limitation, fluorescent primers, fluorogenic probes and fluorescent dyes that bind double-stranded DNA. A common method is the fluorescent 5' nuclease assay. This method exploits the 5' nuclease activity of certain thermostable DNA polymerases (such as Taq or Tfl DNA polymerases) to cleave an oligomeric probe during the PCR process. The oligomer is selected to anneal to the amplified target sequence under elongation conditions. The probe typically has a fluorescent reporter on its 5' end and a fluorescent quencher of the reporter at the 3' end. So long as the oligomer is intact, the fluorescent signal from the reporter is quenched. However, when the oligomer is digested during the elongation process, the fluorescent reporter is no longer in proximity to the quencher. The relative accumulation of free fluorescent reporter for a given amplicon may be compared to the accumulation of the same amplicons for a control sample and/or to that of a control gene, such as, without limitation, β-gus, β-actin or 18SrRNA to determine the relative abundance of a given cDNA product of a given RNA in a RNA population. Products and reagents for the fluorescent 5' nuclease assay are readily available commercially, for instance from Applied Biosystems.

Equipment and software also are readily available for controlling and monitoring amplicon accumulation in PCR and QRT-PCR according to the fluorescent 5' nuclease assay and other QPCR/QRT-PCR procedures, including the Smart Cycler, commercially available from Cepheid of Sunnyvale, Calif., the ABI Prism 7700 Sequence Detection System (TaqMan), commercially available from Applied Biosystems. A cartridge-based sample preparation prototype system (GenXpert) combines a thermal cycler and fluorescent detection device having the capabilities of the Smart Cycler product with fluid circuits and processing elements capable of automatically extracting specific nucleic acids from a tissue sample and performing QPCR or QRT-PCR on the nucleic acid. The system uses disposable cartridges that can be configured and pre-loaded with a broad variety of reagents. Such a system can be configured to disrupt tissue and extract total RNA or mRNA from the sample. The reverse transcriptase reaction components can be added automatically to the RNA and the QPCR reaction components can be added automatically upon completion of the reverse transcriptase reaction.

Further, the PCR reaction may be monitored of production (or loss) of a particular fluorochrome from the reaction. When the fluorochrome levels reach (or fall to) a desired level, the automated system will automatically alter the PCR conditions. In one non-limiting example, this is particularly useful in the multiplexed embodiment described above, where a more-abundant (control) target species is amplified by the first, lower Tm, primer set at a lower temperature than the less abundant species amplified by the second, higher Tm, primer set. In the first stage of the PCR amplification, the annealing step of the cycling reaction is conducted at a temperature that permits amplification of the more abundant target species. The annealing temperature then is automatically raised to essentially stop amplification of the more abundant target species.

In the above-described reactions, the amounts of certain reverse transcriptase and the PCR reaction components typically are atypical in order to take advantage of the faster ramp times of some thermal cyclers. Specifically, the primer concentrations are very high. Typical gene-specific primer concentrations for reverse transcriptase reactions are less than about 20 nM. To achieve a rapid reverse transcriptase reaction on the order of one to two minutes, the reverse transcriptase primer concentration was raised to greater than 20 nM, preferably at least about 50 nM, and typically about 100 nM. Standard PCR primer concentrations range from 100 nM to 300 nM. Higher concentrations may be used in standard PCR reactions to compensate for Tm variations. However, for purposes herein, the referenced primer concentrations are for circumstances where no Tm compensation is needed. Proportionately higher concentrations of primers may be empirically determined and used if Tm compensation is necessary or desired. To achieve rapid PCR reactions, the PCR primer concentrations typically are greater than 200 nM, preferably greater than about 500 nM and typically about 800 nM. Typically, the ratio of reverse transcriptase primer to PCR primer is about 1 to 8 or more. The increase in primer concentrations permitted PCR experiments of 40 cycles to be conducted in less than 20 minutes, as described below in Example 2.

A sensitive reverse transcriptase may be preferred in certain circumstances where either low amounts of RNA are present or a target RNA is a low abundance RNA. By the term "sensitive reverse transcriptase," it is meant a reverse transcriptase capable of producing suitable PCR templates from low copy number transcripts for use as PCR templates. The sensitivity of the sensitive reverse transcriptase may derive from the physical nature of the enzyme, or from specific reaction conditions of the reverse transcriptase reaction mixture that produces the enhanced sensitivity. One example of a sensitive reverse transcriptase is SensiScript RT reverse transcriptase, commercially available from Qiagen, Inc. of Valencia Calif. This reverse transcriptase is optimized for the production of cDNA from RNA samples of <50 ng, but also has the ability to produce PCR templates from low copy number transcripts. In practice, in the assays described herein, adequate results were obtained for samples of up to, and even in excess of, about 400 ng RNA. Other sensitive reverse transcriptases having substantially similar ability to reverse transcribe low copy number transcripts would be equivalent sensitive reverse transcriptase for the purposes described herein. Notwithstanding the above, the ability of the sensitive reverse transcriptase to produce cDNA from low quantities of RNA is secondary to the ability of the enzyme, or enzyme reaction system to produce PCR templates from low copy number sequences.

As discussed above, the procedures described herein also may be used in multiplex QRT-PCR processes. In its broadest sense, a multiplex PCR process involves production of two or more amplicons in the same reaction vessel. Multiplex amplicons may be analyzed by gel electrophoresis and detection of the amplicons by one of a variety of methods, such as, without limitation ethidium bromide staining, Southern blotting and hybridization to probes, or by incorporating fluorescent or radioactive moieties into the amplicons and subsequently viewing the product on a gel. However, real-time monitoring of the production of two or more amplicons is preferred. The fluorescent 5' nuclease assay is the most common monitoring method. Equipment is now available (for example, the above-described Smart Cycler and TaqMan products) that permits the real-time monitoring of accumulation of two or more fluorescent reporters in the same tube. For multiplex monitoring of the fluorescent 5' nuclease assay, oligomers are provided corresponding to each amplicon species to be detected. The oligomer probe for each amplicon species has a fluorescent reporter with a different peak emission wavelength than the oligomer probe(s) for each other amplicons species. The accumulation of each unquenched fluorescent reporter can be monitored to determine the relative amounts of the target sequence corresponding to each amplicon.

In traditional multiplex QPCR and QRT-PCR procedures, the selection of PCR primer sets having similar annealing and elongation kinetics and similar sized amplicons are desirable. The design and selection of appropriate PCR primer sets is a process that is well known to a person skilled in the art. The process for identifying optimal PCR primer sets, and respective ratios thereof (primer limiting, that is, limiting the abundance of the PCR primers for the more abundant RNA species in a multiplex PCR experiment to permit the detection of less abundant species) to achieve a balanced multiplex reaction also is known. By "balanced," it is meant that certain amplicon(s) do not out-compete the other amplicon(s) for resources, such as dNTPs or enzyme. Equalization of the Tm (melting temperature) for all PCR primer sets also is encouraged. See, for instance, ABI PRISM 7700 Sequence Detection System User Bulletin #5, "Multiplex PCR with TaqMan VIC Probes", Applied Biosystems (1998/2001).

Despite the above, for very low copy number transcripts, it is difficult to design accurate multiplex PCR experiments, even by limiting the PCR primer sets for the more abundant control species. One solution to this problem is to run the PCR reaction for the low abundance RNA in a separate tube for the PCR reaction for the more abundant species. However, that strategy does not take advantage of the benefits of running a multiplex PCR experiment. A two-tube process has several drawbacks, including cost, the addition of more room for experimental error and the increased chance of sample contamination, which is critical in PCR assays.

A method is therefore provided for performing a multiplex PCR process, including QRT-PCR and QPCR, capable of detecting low copy number nucleic acid species along with one or more higher copy number species. The difference between low copy number and high copy number nucleic acid species is relative, but is referred to herein as a difference in the prevalence of a low (lower) copy number species and a high (higher) copy number species of at least about 30-fold, but more typically at least about 100-fold. For purposes herein, the relative prevalence of two nucleic acid species to be amplified is more salient than the relative prevalence of the two nucleic acid species in relation to other nucleic acid species in a given nucleic acid sample because other nucleic acid species in the nucleic acid sample do not directly compete with the species to be amplified for PCR resources.

As used herein, the prevalence of any given nucleic acid species in a given nucleic acid sample, prior to testing, is unknown. Thus, the "expected" number of copies of a given nucleic acid species in an nucleic acid sample often is used herein and is based on historical data on the prevalence of that species in nucleic acid samples. For any given pair of nucleic acid species, one would expect, based on previous determinations of the relative prevalence of the two species in a sample, the prevalence of each species to fall within a range. By determining these ranges one would determine the -fold difference in the expected number of target sequences for each species.

The multiplex PCR method involves performing a two- (or more) stage PCR amplification, permitting modulation of the relative rate of production of a first amplicon by a first primer set and a second amplicon by a second primer set during the respective amplification stages. The PCR amplification of the second amplification stage is conducted under different reaction conditions ("different reaction conditions" include, without limitation, different temperatures for steps in the PCR cycle, such as the annealing step, or differences in the reagents in the PCR reaction mixture, such as differences in primers and/or primer concentrations) than in the first amplification stage. By this method, PCR amplifications to produce amplicons directed to a lower abundance nucleic acid species are effectively "balanced" with PCR amplifications to produce amplicons directed to a higher abundance nucleic acid species. Separating the reaction into two or more temporal stages may be achieved by omitting the PCR primer set for any amplicons that are not to be produced in the first amplification stage. The omitted PCR primer set may then be added to the PCR reaction mixture at the beginning of the second amplification stage. This is best achieved through use of automated processes, such as the GenXpert prototype system described above. Two or more separate amplification stages may be used to tailor and balance multiplex assays, along with, or to the exclusion of tailoring the concentration of the respective primer sets.

A second method for temporally separating the PCR amplification process into two or more stages is to select PCR primer sets with variation in their respective Tm. Two examples of such a method are provided in Examples 3 and 6, below. In one example, primers for a lower copy number nucleic acid species would have a higher Tm ($Tm_1$) than primers for a higher abundance species ($Tm_2$). In this process, the first stage of PCR amplification is conducted for a predetermined number of cycles at a temperature sufficiently high that there is substantially no amplification of the higher abundance species. After the first stage of amplification, the annealing and elongation steps of the PCR reaction are conducted at a lower temperature, typically about $Tm_2$, so that both the lower abundance and the higher abundance amplimers are amplified. It should be noted that Tm, as used herein and unless otherwise noted, refers to "effective Tm," which is the Tm for any given primer in a given reaction mix, which depends on factors, including, without limitation, the nucleic acid sequence of the primer and the primer concentration in the reaction mixture.

It should be noted that PCR amplification is a dynamic process. Without limitation, when using temperature to modulate the respective PCR reactions in a multiplex PCR reaction, the higher temperature annealing stage may be carried out at any temperature typically ranging from just above the lower Tm to just above the higher Tm, so long as the reaction favors production of the amplicon by the higher Tm primer set. Similarly, without limitation, the annealing for the lower temperature reaction typically is at any temperature below the higher Tm of the low temperature primer set that will allow sufficient amplification efficiency by the lower Tm primer set.

In the example provided above, in the higher temperature stage, the amplicon for the low abundance RNA is amplified at a rate faster than the amplicon for the higher abundance RNA (and preferably to the substantial exclusion of production of the second amplicon), so that, prior to the second amplification stage, where it is desirable that amplification of all amplicons proceeds in a substantially balanced manner, the amplicon for the lower abundance RNA is of sufficient abundance that the amplification of the higher abundance RNA does not interfere with the amplification of the amplicon for the lower abundance RNA. In the first stage of amplification, when the amplicon for the low abundance nucleic acid is preferentially amplified, the annealing and elongation steps may be performed above the higher Tm to gain specificity over efficiency (during the second stage of the amplification, since there is a relatively large number of low abundance nucleic acid amplicons, selectivity no longer is a significant issue, and efficiency of amplicon production is preferred). It, therefore, should be noted that although favorable in many instances, the temperature variations may not necessarily result in the complete shutdown of one amplification reaction over another.

In another embodiment, a first primer set with a first Tm may target a more-abundant template sequence (for instance, a control template sequence) and a second primer set with a higher Tm may target a less-abundant template sequence. In this case, the more-abundant template and the less-abundant template may both be amplified in a first stage at a temperature sufficient to allow sufficient amplification with the lower Tm primer set, typically at or above the Tm of the first, lower Tm, primer set. When a threshold amount of amplicon corresponding to the more abundant template is reached, the annealing and/or elongation temperature of the reaction is raised to effectively shut down amplification of the more abundant template.

Selection of three or more sets of PCR primer sets having three or more different Tms (for instance, $Tm_1 > Tm_2 > Tm_3$) can be used to amplify sequences of varying abundance in a stepwise manner, so long as the differences in the Tms are sufficiently large to permit preferential amplification of desired sequences to the substantial exclusion of undesired sequences for a desired number of cycles. In one process, the lowest abundance sequences are amplified in a first stage for a predetermined number of cycles. Next, the lowest abundance and the lesser abundance sequences are amplified in a second stage for a predetermined number of cycles. Lastly, all sequences are amplified in a third stage. As with the two-stage reaction described above, the annealing temperature for each stage may vary, depending on the relative efficiencies of each single amplification reaction of the multiplex reaction. It should be recognized that two or more amplimers may have substantially the same Tm, to permit amplification of more than one species of similar abundance at any stage of the amplification process. As with the two-stage reaction, the three-stage reaction may also proceed stepwise from amplification of the most abundant nucleic acid species at the lowest annealing temperature to amplification of the least abundant species at the highest annealing temperature.

By this sequential amplification method, an additional tool is provided for the "balancing" of multiplex PCR reactions besides the matching of Tms and using limiting amounts of one or more PCR primer sets. The exploitation of PCR primer sets with different Tms as a method for sequentially amplifying different amplicons may be preferred in certain circumstances to the sequential addition of additional primer sets. However, the use of temperature-dependent sequencing of multiplex PCR reactions may be coupled with the sequential physical addition of primer sets to a single reaction mixture.

Also provided is an internal positive control that confirms the operation of a particular amplification reaction for a negative result. The internal positive controls (IPC) are DNA oligonucleotides that have the same primer sequences as the target gene (CEA or tyrosinase) but have a different internal probe sequence. Selected sites in the IPCs optionally may be synthesized with uracil instead of thymine so that contamination with the highly concentrated mimic could be controlled using uracil DNA glycosylase, if required. The IPCs may be added to any PCR reaction mastermix in amounts that are determined empirically to give Ct values typically greater than the Ct values of the endogenous target of the primer set. The PCR assays are then performed according to standard protocols, and even when there is no endogenous target for the primer set, the IPC would be amplified, thereby verifying that the failure to amplify the target endogenous DNA is not a failure of the PCR reagents in the mastermix. In this embodiment, the IPC probe fluoresces differently than the probe for the endogenous sequences. A variation of this for use in RT-PCR reactions is where the IPC is an RNA and the RNA includes an RT primer sequence. In this embodiment, the IPC verifies function of both the RT and PCR reactions. Both RNA and DNA IPCs (with different corresponding probes) may also be employed to differentiate difficulties in the RT and PCR reactions.

The methods described herein are generally applicable to quantitative PCR and RT-PCR methods. Described herein and the attached manuscripts are methods for the detection of carcinoembryonic antigen (CEA) and prognosis of adenocarcinomas of the esophagus. The methods described herein are methods that are equally applicable to the identification of other micrometastases, including occult micrometastases, in a variety of other tumor types. The rapid protocols described herein may be run in about 20 minutes. This short time period permits the assay to be run intraoperatively so that a surgeon can decide on a surgical course during a single operation, rather than requiring a second operation, or requiring the surgeon to perform unneeded or overly broad prophylactic procedures. For instance, in the surgical evaluation of certain cancers, including breast cancer and melanoma, sentinel lymph nodes are removed in a first operation. The sentinel nodes are later evaluated for micrometastases, and, when micrometastases are detected in a patient's sentinel lymph node, the patient will need a second operation, thereby increasing the patient's surgical risks and patient discomfort associated with multiple operations. In the case of lung or esophageal cancer, intraoperative analysis of lymph nodes can be used to determine the extent of resection required and/or the need for neoadjuvant chemotherapy. With the ability to determine the expression levels of certain tumor-specific markers, such as, without limitation CEA, MUC-1, CK-19, tyrosinase and MART-1, in less than 30 minutes with increased accuracy, a physician can make an immediate decision on how to proceed. The rapid test also is applicable to needle biopsies taken in a physician's office. A patient need not wait for days to get the results of a biopsy (such as a needle biopsy of a tumor or lymph node), but can now get more accurate results in a very short time. The methods described herein are applicable to detect, without limitation, a variety of expressed RNAs, whether normal or abnormal, DNA rearrangements or the presence of additional or abnormal nucleic acids, such as viral nucleic acids.

In the commercialization of the above-described methods for multiplexed and non-multiplexed QRT-PCR and/or QPCR, certain kits for detection of specific nucleic acids will be particularly useful. One example of such a kit would include reagents necessary for the one-tube QRT-PCR process described above. In one example, the kit would include the above-described reagents, including reverse transcriptase, a reverse transcriptase primer, a corresponding PCR primer set, a thermostable DNA polymerase, such as Taq polymerase, and a suitable fluorescent reporter, such as, without limitation, a probe for a fluorescent 5' nuclease assay, a molecular beacon probe, a single dye primer or a fluorescent dye specific to double-stranded DNA, such as ethidium bromide. The primers may be present in quantities that would yield the high concentrations described above. Thermostable DNA polymerases are commonly and commercially available from a variety of manufacturers. Additional materials in the kit may include: suitable reaction tubes or vials, a barrier composition, typically a wax bead, optionally including magnesium; reaction mixtures (typically 10×) for the reverse transcriptase and the PCR stages, including necessary buffers and reagents such as dNTPs; nuclease- or RNase- free water; RNase inhibitor; control nucleic acid(s) and/or any additional buffers, compounds, co-factors, ionic constituents, proteins and enzymes, polymers, and the like that may be used in reverse transcriptase and/or PCR stages of QRT-PCR reactions.

A second kit is specific to the above-described multiplex PCR procedure. The kit may include, without limitation, a first PCR primer set for a low abundance nucleic acid, having a first Tm and a second PCR primer set for a more abundant nucleic acid, having a second Tm. The relative Tms of the primer sets are selected for their ability to balance a multiplex PCR reaction according to the methods described herein. In a kit for QRT-PCR, the kit also may include: any suitable reverse transcriptase, reverse transcriptase primers specific to the nucleic acids to be amplified, a barrier composition, such as a wax bead, a thermostable DNA polymerase and/or a suitable fluorescent reporter, such as, without limitation, a probe for a fluorescent 5' nuclease assay, a molecular beacon probe, a single dye primer or a fluorescent dye specific to double-stranded DNA, such as ethidium bromide. The kit may include a sensitive reverse transcriptase for the detection of low abundance RNAs. As above, additional materials in the kit may include: suitable reaction tubes or vials, a barrier, typically a wax bead, optionally including magnesium; reaction mixtures (typically 10×) for the reverse transcriptase and the PCR stages, including necessary buffers and reagents such as dNTPs; nuclease- or RNase- free water; RNase inhibitor; control nucleic acid(s) and/or any additional buffers, compounds, co-factors, ionic constituents, proteins and enzymes, polymers, and the like that may be used in reverse transcriptase and/or PCR stages of QRT-PCR reactions.

The above-described kits or cartridges also may include reagents and mechanical components suitable for the manual or automated extraction of nucleic acid from tissue samples. These reagents are known to those skilled in the art and typically are a matter of design choice. For instance, in an automated process, tissue may be disrupted ultrasonically in a suitable lysis solution provided in the kit or cartridge. The resultant lysate solution may then be filtered and RNA may be bound to RNA-binding magnetic beads also provided in the kit or cartridge. The beads/RNA may be washed, and the RNA eluted prior to the reverse transcriptase reaction. In the case of automated nucleic acid extraction, the choice of reagents and their mode of packaging (for instance disposable single-use cartridges) typically are dictated by the physical configuration of the robotics and fluidics of the specific extraction system, such as Cepheid's GenXpert prototype system.

The constituents of the kits may be packaged together or separately, and each constituent may be presented in one or more tubes or vials, or in cartridge form (a modular unit containing one or more reagents for use in an automated device), as is appropriate. The constituents, independently or together, may be packaged in a variety of states, including without limitation, in lyophilized, glassified, aqueous or other forms as is appropriate.

FIG. 1 is a schematic cross-section diagram of a cartridge 10 for use in the above-described automated methods. Cartridge 10 includes compartments 20 in which any desired reagent may be stored for use. Compartments 20 are separated by walls 25. Cartridge 10 includes multiple passageways 30 fluidly connected to a common passageway 40. A valve member 50 is shown within common passageway 40. Valve member 50 controls flow of reagent from individual compartments 20 into common passageway 40. Common passageway 40 is fluidly connected to a reaction vessel (not shown) into which reagents from compartments 20 are transferred. The reagents contained within compartments 20 may include, without limitation, reagents for cell lysis, for nucleic acid purification, for reverse transcription or for PCR reactions. FIG. 1 shows one of many possible permutations of a cartridge device useful in automating molecular purifications and assays. The cartridge and compartments may have any desired shape and size, as dictated by empirical factors as well as by designer preference. The choice of and configuration of fluid connections and valves also is a matter of design choice, and may vary greatly.

EXAMPLES

Example 1

One-tube QRT-PCR

With the introduction of real-time, fluorescence-based 5' nuclease PCR (Gibson, U. E., C. A. Heid and P. M. Williams. 1996. A novel method for real time quantitative RT PCR. Genome Res. 6:995–1001; Heid, C. A., J. Stevens, K. J. Livak and P. M. Williams. 1996. Real time quantitative PCR. Genome Res. 6:986–994) and instruments such as the ABI PRISM™ 7700 (TaqMan®) sequence detector (Applied Biosystems, Foster City, Calif., USA), quantitative RT-PCR is now a widely accepted method for measuring gene expression levels. Quantitative RT-PCR is a sensitive technique and is particularly useful for the analysis of samples containing limited amounts of nucleic acids, such as in clinical tissues (Collins, C., J. M. Rommens, D. Kowbel, T. Godrey, M. Tanner, S. I. Hwang, D. Polikoff, G. Nonet et al. 1998. Positional cloning of ZNF217 and NABC1: genes amplified at 20q 13.2 and overexpressed in breast carcinoma. Proc. Natl. Acad. Sci. USA 95:8703–8708). When quantitating these small amounts of RNA and/or very low-abundance mRNA species, obtaining maximum sensitivity from a quantitative RT-PCR is extremely important. While consecutive rounds of nested PCR are often used to obtain maximum sensitivity, this is difficult to achieve and still maintain accurate quantitation. Furthermore, multiple rounds of PCR increase the risk of contamination, a serious problem when working at the desired sensitivity levels. One-tube RT-PCR (RT and PCR in the same tube using the reverse PCR primer for the RT) reduces the risk of contamination when using the ABI PRISM 7700 because the reaction tubes are never opened.

Theoretically, a one-tube procedure should have the same sensitivity as a two-step approach (separate RT followed by PCR), but in practice this is not the case (Battaglia, M., P. Pedrazzoli, B. Palermo, A. Lanza, F. Bertolini, N. Gibelli, G. A. Da Prada, A. Zambelli et al. 1998. Epithelial tumour cell detection and the unsolved problems of nested RT-PCR: a new sensitive one step method without false positive results. Bone Marrow Transplant 22:693–698). It has been found that the sensitivity of one-tube RT-PCR is limited by the relative nonspecificity of the RT step. This nonspecificity arises from the fact that the RT is carried out at relatively low temperature and without a hot start, thus allowing nonspecific priming by both the desired RT "reverse" primer and also from the "forward" PCR primer. As the amount of target decreases in the input RNA sample, priming artifacts from the cold-start RT process can compete with, and reduce the efficiency of, PCR amplification of the desired target sequence. Thus, as RNA input decreases in a one-tube procedure, nonspecific side reactions eventually out-compete the desired reaction, and no specific product is generated. In a two-step or nested RT-PCR procedure, specificity can be achieved with the use of hot-start PCR and a primer set 5' upstream from the RT primer. However, this is not the case in a one-tube procedure unless one is willing to open the reaction tube to add new primers (thus making it a one-tube but two-step procedure). It has been hypothesized that by using an external RT primer and keeping the RT and PCR primers separated during the RT step, PCR specificity and therefore sensitivity in a one-tube RT-PCR should be maintainable. Here, a modified one-tube RT-PCR assay that greatly increases sensitivity and can be used for quantitative RT-PCR on the ABI PRISM 7700 is presented.

Standard one-tube reactions were set up for β-glucuronidase (β-gus) mRNA in 50 µL volumes with the following final concentrations: 10 nM β-gus RT primer (5'-TTTG-GTTGT-CTCTGCCGAGT-3') (SEQ ID NO:2), 100 nM each β-gus PCR primer (GUS-F, 5'-C-TCATTTG-GAATTTTGCCGATT-3')(SEQ ID NO:3); GUS-R, (5'-CCGAGTGAAGATCCC-CTTTTTA-3')(SEQ ID NO:4), 100 nM β-gus probe(5'-6-fam-TGAACAGTCACCGACG-AGAGTGCTGG-tamra-3') (SEQ ID NO: 5), 1× TaqMan reaction buffer (Applied Biosystems), 5.5 mM $MgCl_2$, 300 µM each dNTP, 20 U Rnase inhibitor, 62.5 U SUPER-SCRIPT II™ reverse transcriptase (Life Technologies, Rockville, Md., USA) and 1.25 U AmpliTaq Gold® (Applied Biosystems).

In the modified procedure, physical separation between the RT reaction mixture and the PCR primers was achieved by the use of AmpliWaxe® PCR gem 50 (Applied Biosystems). First, the β-gus PCR primers were pipetted into the PCR plate in a final 5.0-µL volume. One PCR gem 50 was placed in each well, the wells were capped and the plate was centrifuged briefly to avoid the adherence of reagents to the tube wall above the wax barrier. The plate was then heated to 80° C. for 2 min and cooled to 4° C. to produce a wax barrier. A 45 µL upper layer was then pipetted into each well. This mixture contained the β-gus RT primer, the RNA, Rnase inhibitor and SUPERSCRIPT II reverse transcriptase. Both layers were formulated to contain all of the remaining reaction components (buffer, nucleotides, $MgCl_2$) at the concentrations described above. The presence of AmpliTaq Gold in the RT layer is inconsequential because this enzyme is inactive until heated to 95° C.

All reactions were carried out on the ABI PRISM 7700 with the following thermocycler conditions: 48° C. hold for 30 min, 95° C. hold for 12 min, followed by 40 cycles of 95° C. for 20 s and 60° C. for 1 min. The wax layer remained intact for the RT step at 48° C. but was melted during the 12-min, 95° C. AmpliTaq Gold activation step, thus allowing the two layers to mix before the PCR begins. Data were analyzed with Applied Biosystems' sequence detection software.

First, the effect of the wax layer on the fluorescence detection in the TaqMan assay was evaluated to determine the extent of fluorescence quenching by the wax. Using randomly primed cDNA from a lung adenocarcinoma cell line (A549), 20 replicates of PCR for β-gus with and without the wax layer were performed. The results showed no decrease in the overall fluorescence (P=0.935) and no change in the cycle threshold value (P=0.55) between the two groups when compared by the independent samples t-test.

Figure 2:
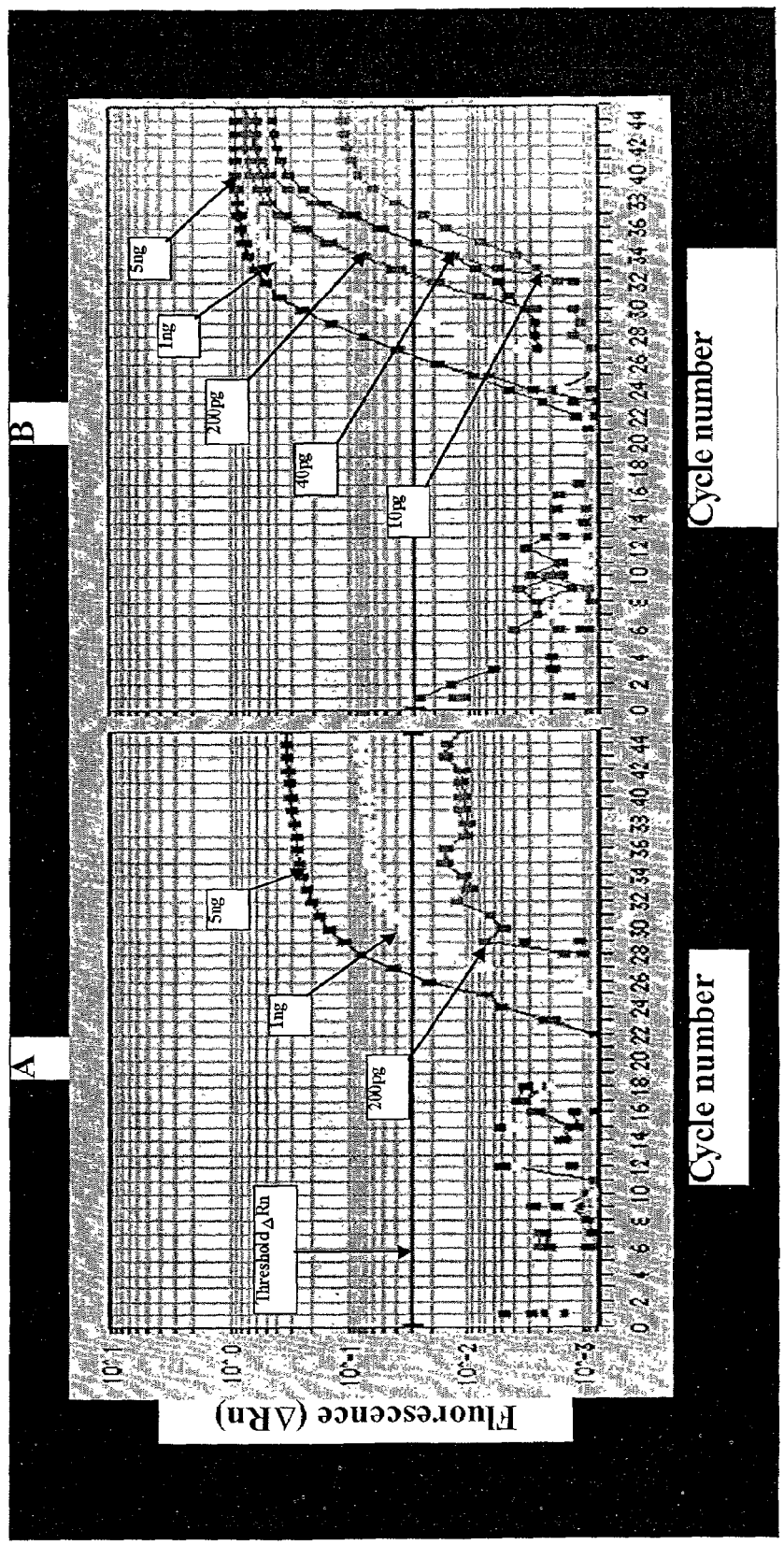
FIG. 2 shows two graphs comparing the sensitivity of the one-tube RT-PCR with (B) and without (A) a wax separating the RT and PCR reactions.
Figure 3:
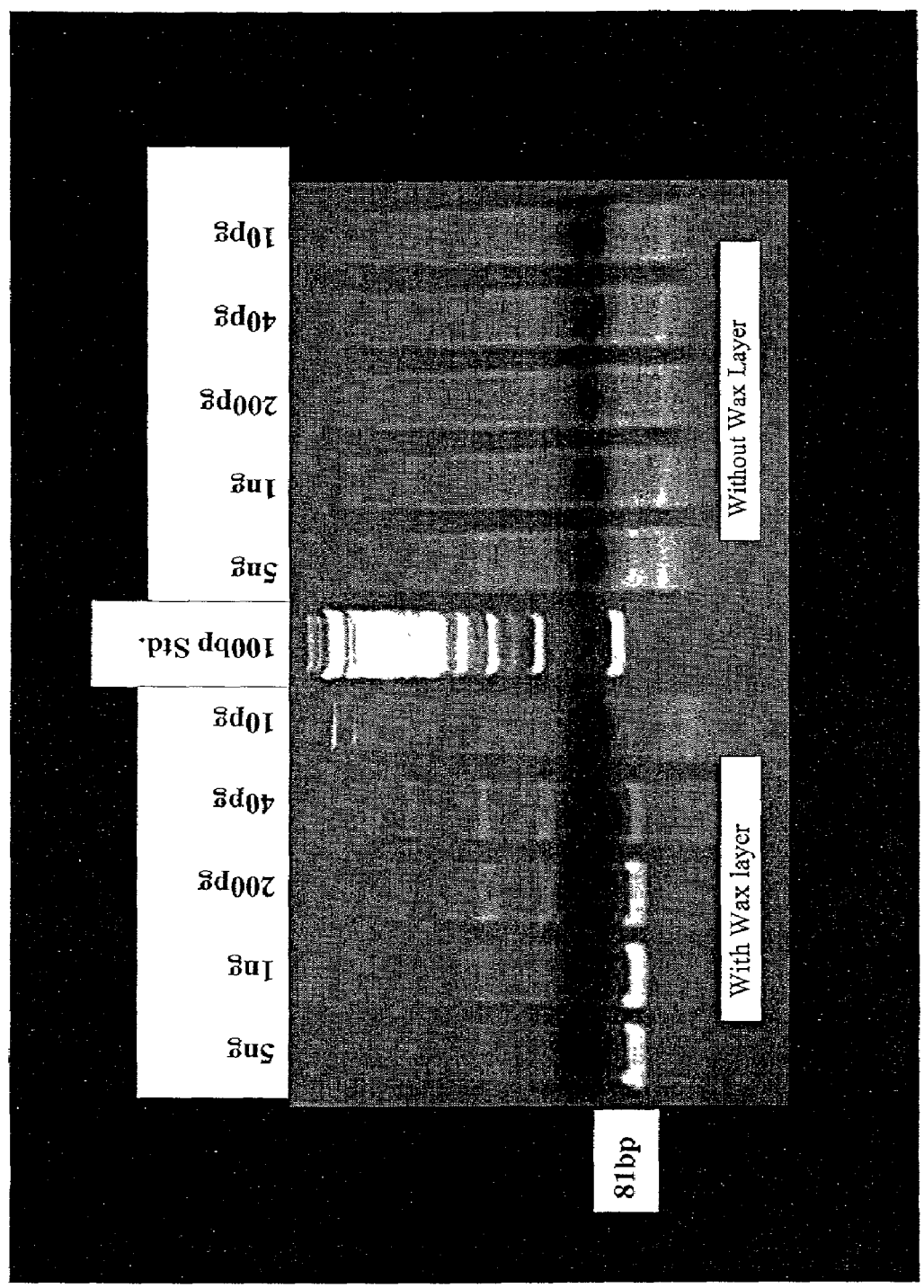
FIG. 3 is a photograph of an ethidium bromide-stained gel comparing RT-PCR product prepared with and without use of a wax layer to separate the RT and PCR reactions.

To compare the sensitivity of the one-tube RT-PCR with and without the wax, serial dilutions of spleen total RNA (Clontech Laboratories, Palo Alto, Calif., USA) from 5 ng to 10 pg were used. The results of the RT-PCR without the wax layer showed that the fluorescence (ΔRn) was weak even at 5 ng RNA input and decreased further by an average factor of 75% every dilution (FIG. 2A). As a result, the 200-pg sample fell below the threshold for detection. However, with the use of the wax layer, the ΔRn remained essentially the same down to the 40-pg dilution, and only at 10 pg was there a 60% drop in the ΔRn (FIG. 2B). Thus, this modified procedure resulted in at least a 20-fold increase in sensitivity. The efficiency (E) of the RT-PCR (as calculated by the formula $E \times 10^{(1/-s)}-1$, where "s" is the slope of the standard curve from the dilutions) (PE Applied Biosystems User Bulletin #2. 1997. Relative quantitation of gene expression. Applied Biosystems, Foster City, Calif.) was also improved by the use of the wax (67% without wax and 77% with wax). A 10-µL aliquot of each reaction was run out on a 10% non-denaturing polyacrylamide gel and stained with ethidium bromide (FIG. 3). With the wax layer, the 81-bp product, corresponding to the expected size, was visible in all but the 10-pg RNA dilution (demonstrating the extra sensitivity of TaqMan detection versus ethidium bromide). In the reactions without wax, however, no reactions produced a clean signal at 81 bp. Instead, there was a smear of nonspecific products at all RNA concentrations.

The same experiments were performed using Sensiscript RT® (Qiagen, Valencia, Calif., USA). With this enzyme, PCR product was just detectable down to the 40-pg dilution even without the use of the wax layer. However, the total fluorescence continued to drop with each consecutive dilution. With the addition of the wax, the ΔRn remained constant, and detection was easily achieved down to 10 pg. Notably, the efficiency of this one-tube reaction was near 100% (measured using the methods described above). Thus, the sensitivity of the one-tube RT-PCR for the 5' fluorogenic assay in the ABI PRISM 7700 is significantly enhanced by the use of the AmpliWax PCR gem 50. PCR gems were originally designed to facilitate hot start PCR, but this is no longer necessary with new enzymes for automatic hot start. Here, it is shown that these same AmpliWax PCR gems are beneficial in the context of a one-step quantitative RT-PCR. Furthermore by eliminating the need to open the PCR tubes the occurrence of cDNA or PCR product contamination was minimazed. Finally, the preservation of PCR specifically facilitates the amplification of the desired product, and as such, is relevant even in non-quantitative end-point assays.

Example 2

Quantitative RT-PCR in Less than Twenty Minutes

The following is a one-tube two-step assay for quantitative reverse transcription followed by polymerase chain reaction (QRT-PCR), which can be completed in less than twenty minutes using Cepheid's Smart Cycler. Current methods of QRT-PCR for the 5' fluorogenic assay in the Applied Biosystem's 7700 require more than two hours. By altering primer and probe concentrations and utilizing the fast ramping ability of the Smart Cycler, the reverse transcriptase reaction time was reduced to 2 minutes and the PCR time was reduced to 16 minutes using a 1 second denaturation and a 6 second extension for 40 cycles.

PCR reactions were designed for β-glucuronidase (β-gus) and carcinoembryonic antigen (CEA) cDNA respectively in 25µl volumes with the following final concentrations: 400nM each β-gus PCR primer (GUS-F, 5'-CTC ATT TGG AAT TTT GCC GAT T-3' (SEQ ID NO:3); (GUS-R, 5'-CCG AGT GAA GAT CCC CTT TTT A-3' )(SEQ ID NO:4) or CEA primer (CEA-F, 5'-AGA CAA TCA CAG TCT CTG CGG A-3')(SEQ ID NO:6); (CEA-R, 5'-ATC CTT GTC CTC CAC GGG TT-3') (SEQ ID NO:7), 200 nM β-gus probe (5'-6-fam-TGAACAGTCACCGACGAGAGT-GCTGG-tamra-3) (SEQ ID NO:5) or 200nM CEA probe (5'-6-fam-CAA GCC CTC CAT CTC CAG CAA CAA CT-tamra-3) (SEQ ID NO:8), 1× Platinum Taq reaction buffer, 4.5 mM MgC12, 300 uM each dNTP, 0.06 U/ul Platinum Taq DNA polymerase (GIBCO BRL).

Tests were run using $MgCl_2$ at 1.5, 2.5, 3.5 and 4.5 mM concentrations and it was determined that 4.5 mM is optimal for this assay. The cDNA for these reactions was generated from gene specific reverse transcriptase reactions for GUS and CEA using a 250 ng input of RNA from an A549 cell line (GUS) and fresh lymph node RNA that was positive for CEA.

RT-PCR reactions were designed for β-gus mRNA and CEA mRNA in 25 ul volumes with the same PCR concentrations as above and the following reverse transcriptase concentrations: 60 nM β-gus reverse transcriptase primer (5'-TTTGGTTGTCTCTGCCGAGT-3') (SEQ ID NO:2) or CEA reverse transcriptase primer (5'-GTG AAG GCC ACA GCA T-3') (SEQ ID NO: 9), 1 ul Sensiscript and 0.8U/ul RNase inhibitor. The RNA input for the RT-PCR was 400ng A549 and 25 ng lymph node.

The denaturation step was first optimized by comparing 1, 2, 5, 7 and 10 second denaturation at 95° C. in combination with a 30 second extension for 40 cycles. Platinum Taq activation was done at 95° C. for 30 seconds. The results of this testing show no significant loss of sensitivity between a 1 second denaturation versus a 10 second denaturation for either gene. Next, the extension step was optimized by comparing 3, 5, 7, 10, 13, 15 and 30 second extension at 64° C. in combination with a 15 second denaturation for 40 cycles. Platinum Taq activation was done at 95° C. for 30 seconds.

The results of this testing show minimal loss of sensitivity of approximately one and a half cycles from 30 second extension to 3 second extension for GUS. For CEA, no significant loss is seen from 30 second extension to 3 second extension.

Next, the combined effect of altering denaturation/extension time was evaluated by comparing a ⅓ second PCR to a 2/15 second PCR over 40 cycles The results show a 2.2 and 1.1 cycle loss in sensitivity for GUS and CEA, respectively. A 2/15 second PCR requires 22 minutes while a ⅓ second PCR requires 16 minutes, thus this insignificant loss in sensitivity is well worth cutting the reaction time by 6 minutes.

In an attempt to reduce the ramping time from denaturation to extension, the effect of decreasing the denaturation temperature from 95° C. to 90° C. to 85° C. was evaluated. For GUS, there is no significant loss in sensitivity when denaturation is done at 95° C. or 85° C. For CEA, the reaction failed when denaturation was done at 85° C. but no significant loss in sensitivity was seen from denaturation at 95° C. to 90° C. The amount of time gained by doing a 90° C. versus a 95° C. denaturation is about 1.5 minutes over 40 cycles.

Taq activation time was evaluated and no significant loss in sensitivity for either gene by decreasing Taq activation from 30 seconds to 10 seconds was found.

After optimizing the PCR conditions, the reverse transcriptase reaction was optimized. The reverse transcriptase reaction was done in a total volume of 15 µl. After completion the reaction, the mixture was held at 70° C. at which time the PCR components (total volume, 10 µl) were added. Reverse transcriptase reaction times of 2, 3, 5, 7 and 10 minutes were compared. The reverse transcriptase reactions were combined with PCR conditions that included a 1 second denaturation at 95° C. and a 5 second extension at 64° C. for 40 cycles for both genes.

The results of these reverse transcriptase reaction time trials show a loss in sensitivity of 1.1 cycle for GUS and 1.81 cycles for CEA from a 10 minute reverse transcriptase reaction to a 2 minute reverse transcriptase reaction. Next, the total effect of decreasing the RT-PCR times on the sensitivity of the assay was evaluated by comparing the following RT-PCR conditions: 1) a "gold standard" with a 10 minute reverse transcriptase reaction followed by 10 second denaturation and 15 second extension for 40 cycles, total run time of 38 minutes, 2) a 5 minute reverse transcriptase reaction followed by optimized PCR conditions of 1 second denaturation and 5 second extension for 40 cycles, total run time of 20 minutes, 3) a 2 minute reverse transcriptase reaction followed by optimized PCR conditions, total run time of 17 minutes, and 4) a "quick" RT-PCR with a 2 minute reverse transcriptase reaction followed by 1 second denaturation and 3 second extension for 40 cycles, total run time of 15 minutes. For Gus, the "gold standard" RT-PCR had a Ct (number of cycles required to reach a predetermined threshold, reference fluorescence level) of 25.88±0.78 while the 2 min reverse transcriptase reaction with optimized PCR conditions had a Ct of 29.42±0.7 showing a total cycle difference of 3.54. For CEA, the "gold standard" RT-PCR had a Ct of 29.94±2.2 while the 2 min RT with optimized PCR conditions had a Ct of 34.92±0.5 showing a total cycle difference of 4.98.

In an attempt to increase the sensitivity of the shorter protocol, the effects of increasing the primer concentrations for Gus and CEA were evaluated. The experiment described above was repeated with an increase of the concentration of the RT primer from 60 nM to 100 nM and the F/R PCR primers from 400 nM to 800 nM. The results of this test show a 2.3 cycle difference (4.98 with low primer concentrations) between the gold standard versus the 2 min optimal protocol for CEA and a 1.63 (3.54 with low primer concentrations) cycle difference for Gus. This small loss in sensitivity is insignificant considering that the total RT-PCR time was reduced from 38 minutes to 17 minutes.

The PCR efficiency for CEA was evaluated using the optimized conditions of 1 second denaturation and 6 second extension for 40 cycles on a dilution series of the fresh lymph node cDNA. The correlation coefficient of this assay is 0.9974 indicating excellent reproducibility. The PCR efficiency can be calculated as follows:

$$E = 10^{(1/-S)} - 1,$$

where S equals the slope of a standard curve of a serial dilution of template, for which Ct is plotted versus the log DNA concentration. Therefore, the PCR efficiency for this assay is 96.7%.

Next, the RT-PCR efficiency of the assay was evaluated using a 2 min reverse transcriptase reaction followed by 40 cycles of PCR using the optimized conditions. A fresh lymph node RNA 2× dilution series was prepared in 400 ng spleen RNA. RT-PCR for both CEA and GUS were performed. The mean GUS Ct was 28.39±1.36. The efficiency for this assay was greater than 100 percent. The same assay was done using an equal mixture of Superscript II and Sensiscript rather than only Sensiscript. The efficiency of this assay was closer to 100 percent.

Example 3

Rapid QRT-PCR: Multiplexed Assay

The Smart Cycler is currently capable of 4-color fluorescence detection and therefore allows multiplexing of QRT-PCR reactions. One goal is to multiplex internal controls for RT-PCR, an endogenous reference gene control to correct for RNA input, and the target gene (for example CEA) all in one tube. Initial tests multiplexing β-GUS and CEA worked well at moderate CEA mRNA levels but failed when very low levels of CEA were present. Thus, the sensitivity of this reaction was not adequate for micrometastasis detection. One method to overcome this is to limit the amount of PCR primer used for the endogenous control gene. Theoretically this allows the rare CEA mRNA species to more effectively compete for PCR reagents, especially in later cycles. Attempts to do this with β-Gus, or a second endogenous control gene (18s ribosomal RNA), also failed to give adequate sensitivity.

Figure 4:
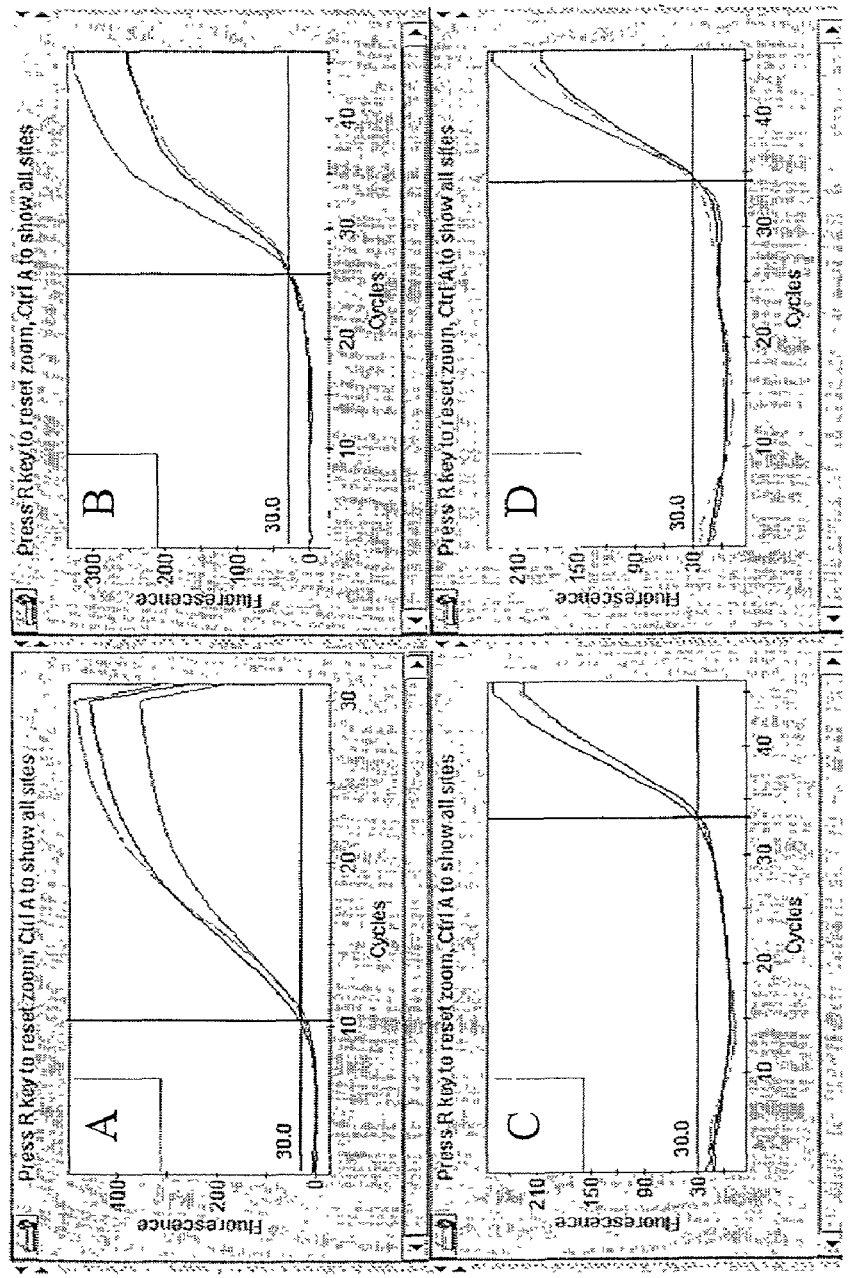
FIG. 4 provides four graphs showing the amplification of CEA and 18SrRNA in a multiplexed reaction as described in Example 3. Panels A and C show the results for 18SrRNA and CEA respectively when run in a singleplex using optimal conditions. Panels B and D show 18SrRNA and CEA multiplexed.

It was hypothesized that the problem lay in the initial cycles, when competition between the two PCR reactions was most critical. To overcome this, but still carry out the assay in a single tube with no extra handling, the 18S rRNA (and β-GUS) endogenous control primers were redesigned so that the annealing temperature was 10° C. below that of the CEA primers (all primers used in the QRT-PCR reactions described herein are listed below in Table 1). PCR was then carried out in two 20-cycle steps, the first with an anneal/extend temperature of 64° C. and the second with an anneal-extend temperature of 53° C. The multiplex reaction reagent concentrations were the same as those used in the singleplex reaction with the following modifications. The target gene primer concentrations were at 400 nM while that of the endogenous controls' were at 100 nM, the reverse transcriptase primer concentrations were at 60nM each and the cycling conditions were modified as previously mentioned. Theoretically the 18S rRNA primers would not function in the first 20 cycles and the CEA amplification could proceed without competition. In the next 20 cycles, CEA PCR product would already be boosted to the point that it could compete efficiently with the 18S rRNA PCR. The results of this experiment are shown in FIG. 4. Panels A and C show the results for 18S rRNA and CEA respectively when run in a singleplex using optimal conditions. Panels B and D show 18S rRNA and CEA multiplexed. Note that while these reactions were multiplexed in the same tube, with different fluorescent dyes, the software does not allow two dyes to be plotted on the same graph. In the singleplex reaction, 18S rRNA crossed the 30-fluorescence unit threshold at 10 cycles (Panel A). Using the new PCR primers, and modified protocol, the 18S rRNA PCR reaction did not cross threshold until 26 cycles (Panel B), 6 cycles after the anneal/extend temperature was dropped to 53° C. This reaction was expected to cross threshold at 30 cycles (20+10), thus it appears that there is some 18S rRNA PCR amplification occurring during the first 20 cycles, even at 64° C. In the CEA reactions the singleplex reached threshold at 33.5 cycles (Panel C) while the multiplexed CEA reached threshold at 34.5 cycles. Thus only one cycle sensitivity was lost in this reaction.

TABLE 1

| Name | Sequence |
| --- | --- |
| CEA probe | CAA GCC CTC CAT CTC CAG CAA CAA CT (SEQ ID NO: 8) |
| CEA RT | GTG AAG GCC ACA GCA T (SEQ ID NO: 9) |
| CEA-F77 | AGA CAA TCA CAG TCT CTG CGG A (SEQ ID NO: 6) |
| CEA-R77 | ATC CTT GTC CTC CAC GGG TT (SEQ ID NO: 7) |
| 18S probe | TGC TGG CAC CAG ACT TGC CCT C (SEQ ID NO: 10) |
| 18S-F89 | CCC TGT AAT TGG AAT GAG TCC AC (SEQ ID NO: 11) |

TABLE 1-continued

| Name | Sequence |
|---|---|
| 18S-R89 | GCT GGA ATT ACC GCG GCT (SEQ ID NO: 12) |
| 18S-F2-low Temp | CCC TGT AAT TGG AAT GAG T (SEQ ID NO: 13) |
| 18S-R2-low Temp | GCT GGA ATT ACC GCG (SEQ ID NO: 14) |
| Gus probe | TGA ACA GTC ACC GAC GAG AGT GCT GG (SEQ ID NO: 5) |
| GUS RT | TGG TTG TCT CTG CCG A (SEQ ID NO: 15) |
| Gus 81F | CTC ATT TGG AAT TTT GCC GAT T (SEQ ID NO: 3) |
| Gus 81R | CCG AGT GAA GAT CCC CTT TTT A (SEQ ID NO: 4) |
| Gus 80F-low Temp | CTC ATT TGG AAT TTT GCC (SEQ ID NO: 16) |
| Gus 80R-low Temp | CG AGT GAA GAT CCC CTT (SEQ ID NO: 17) |

Of note, the above-described CEA primers were designed to span the junction between exons 6 and 7 of the CEA mRNA. The primers also amplify sequences spanning the junction between exons 2–3 of the CEA mRNA. This primer set was selected to yield superior selectivity to certain earlier described primer sets. The addition of one or more flanking nucleotides of the CEA sequence (FIG. 5, GenBank Accession No. XM_012777) to the 5' or 3' ends of either of the CEA primers would not appreciably affect the above-described assays, except with respect to expected changes in the Tm of the primer set. Other CEA-specific primers may be selected from the same general regions (exon 2–3 and exon 6–7 junctions) that the above-described CEA forward and reverse primers are selected to the same or similar effect as the above-described CEA primers. Preferably, any selected primer sets will yield an amplicon of less than about 100 bases, which adds to the ability to conduct a rapid QRT-PCR assay.

Example 4

Prognostic Value of Quantitative Reverse Transcription-Polymerase Chain Reaction in Node-Negative Esophageal Cancer Patients Introduction The incidence of adenocarcinoma of the esophagus is increasing at an alarming rate, exceeding that of any other solid tumor. Up to 50% of patients present with advanced disease, yielding an overall 5-year survival of 10–13%. As with other tumor types, survival of esophageal cancer patients is strongly predicted by histological evidence of lymph node involvement. Although current histological methods for lymph node staging provide reliable information about populations of patients, they cannot predict individual patient outcome within that population. For example, 30–50% of histologically node-negative esophageal cancer patients will suffer disease recurrence within 5 years, despite a potentially curative resection. There is a circumstantial body of evidence indicating that this primary treatment failure is attributable to micrometastatic spread of the tumor that went undetected by routine histological evaluation. Thus, there is a clear need for more sensitive detection of lymph node micrometastases, thereby allowing more individualized prognosis and treatment planning of esophageal cancer patients.

The main problems with current lymph node evaluation are sampling error and poor sensitivity for detecting individual tumor cells or small tumor foci. Histological examination only samples a very small percentage of each lymph node, and it has been calculated that a pathologist has only a 1% chance of detecting a micrometastatic focus of three tumor cell diameter. Immunohistochemical staining for tumor markers improves the sensitivity of micrometastasis detection and, when combined with serial sectioning to reduce the sampling error, results in upstaging of a significant number of patients. This technique has been used in esophagus cancer, and 17% of histologically negative nodes were found to contain micrometastatic disease. In this report, IHC3-positive lymph nodes correlated with disease recurrence, but these findings were questioned in a later study in which IHC did not show any prognostic value. Other studies have used molecular methods such as RT-PCR to detect micrometastases. RT-PCR is capable of detecting the mRNA for tumor markers, such as CEA, cytokeratin 19, cytokeratin 20, and others, in a variety of tissues, including blood, bone marrow, and lymph nodes, that are histologically cancer free. In esophageal cancer, RT-PCR has been used on several small series of patients, but the clinical significance of RT-PCR-positive nodes is not known because little clinical follow-up has been reported. In other tumor types, studies have shown that RT-PCR improves sensitivity, but poor specificity and false-positive results in control lymph nodes from patients without cancer have made the clinical application of this information difficult. False positives are, at least in part, attributable to the previously described phenomenon of ectopic gene expression, which results in very low background levels of expression of most genes in all tissue types. Thus, although previous studies have used qualitative, gel-based RT-PCR methods, it is now becoming apparent that this simple plus/minus method for detection of tumor markers is not always a reliable sign of micrometastases. With the introduction of the fluorescent 5' nuclease assay, QRT-PCR is now a relatively simple technique. It was therefore hypothesized that a quantitative analysis would offer significant benefits over gel-based RT-PCR and would allow accurate prediction of disease recurrence in histologically node-negative esophageal cancer patients. The objectives of the present were 3-fold: (a) to determined the ability of QRT-PCR to accurately distinguish between background gene expression of CEA in lymph nodes and clinically relevant levels that are diagnostic of true micrometastasis; (b) to use real-time QRT-PCR to analyze lymph nodes from 30 node-negative esophageal cancer patients and correlated the results with disease recurrence; and (c) to compare QRT-PCR with standard gel-based RT-PCR on the same samples. It was found that QRT-PCR can easily discriminate background expression from true metastatic disease, QRT-PCR is both sensitive and specific for predicting disease recurrence in nodenegative esophageal cancer patients, and QRT-PCR has greater specificity than gel-based RT-PCR. From these results, it is believed that quantitation addresses all of the problems that have kept RT-PCR from becoming a useful clinical test for micrometastatic disease.

Materials and Methods

Patients: Tissue from 140 paraffin blocks containing 387 lymph nodes were studied from 30 patients who underwent curative resection for histologically lymph node-negative esophageal cancer. The Section of Thoracic Surgery performed all surgeries at the University of Pittsburgh Medical Center between 1991 and 1998. Vital status and recurrence information was obtained from a combination of medical record review, personal contact with the Primary Care Physician, and death certificates. Follow-up data were confirmed for all patients as of August 2001. The median follow-up time for surviving patients was 49 months (range, 28–91 months). Demographics and clinical characteristics were collected (Table 2). Tissue blocks from 10 primary tumors (8 adenocarcinoma and 2 squamous cell carcinoma) and 4 histologically positive lymph nodes were obtained as positive controls. Negative control (benign) lymph nodes were obtained from patients who underwent esophageal surgery for causes unrelated to cancer (hernia repairs and antireflux procedures) and whose lymph nodes were removed incidentally.

TABLE 2

Clinical Characteristics of the study population.

| | | QRT-PCR Result | |
|---|---|---|---|
| Characteristic | Patients (n = 30) | Negative (n = 19) | Positive (n = 11) |
| Gender | | | |
| Male | 22 | 15 | 7 |
| Female | 8 | 4 | 4 |
| Months of follow up | | | |
| Median | 36.0 | 44.6 | 28.0 |
| Range | 5–90.6 | 5–90.6 | 6.3–57.4 |
| Mean Age at Diagnosis | 68.3 | 68.8 | 67.5 |
| Adjuvant Therapy | | | |
| Chemotherapy | 16 | 7 | 9 |
| Radiation | 9 | 3 | 6 |
| Lymphadenopathy on scan | 8 | 3 | 5 |
| Tumor Type | | | |
| Adenocarcinoma | 26 | 18 | 8 |
| Squamous cell | 4 | 1 | 3 |
| pT category* | | | |
| pT1 | 10 | 8 | 2 |
| pT2 | 5 | 4 | 1 |
| pT3 | 10 | 5 | 5 |
| Stage* | | | |
| I | 10 | 8 | 2 |
| IIA | 15 | 9 | 6 |
| Mean Number of Nodes examined (range) | 12.5 (2–31) | 12 (2–31) | 15 (3–23) |

*Four patients who received chemotherapy had no tumor at time of surgery

Tissue and RNA Isolation: All tissues used in the study were formalin-fixed, paraffin-embedded archival specimens obtained from the Pathology tissue banks. H&E-stained slides were also retrieved for each tissue block and were examined to confirm the original node-negative diagnosis. Tissue blocks were mounted on a microtome, and 5–15 5.0 cM sections were cut and placed in 2.0 ml of RNase-free tubes. At the same time, 2 5.0 μM sections were cut (first and last cuts) and mounted on microscope slides for immunohistochemical staining with antibodies against CEA. RNA was isolated using methods described previously (Godfrey, T. E., Kim, S.-H., Chavira, M., Ruff, D. W., Warren, R. S., Gray, J. W., and Jensen, R. H. Quantitative mRNA expression analysis from formalin-fixed, paraffin-embedded tissues using 5' nuclease quantitative RT-PCR. *J. Mol. Diagn.*, 2: 84–91, 2000) and stored in RNA secure resuspension solution (Ambion, Austin, Tex.). The RNA was DNase treated with the DNA free kit (Ambion) and quantitated spectrophotometrically.

QRT-PCR: QRT-PCR was carried out using the 5' nuclease assay and an Applied Biosystems 7700 Sequence Detection Instrument (TaqMan). CEA expression was measured relative to the endogenous control gene, β-gus, using the comparative CT method described previously (Godfrey, T. E., Kim, S.-H., Chavira, M., Ruff, D. W., Warren, R. S.,Gray, J. W., and Jensen, R. H. Quantitative mRNA expression analysis from formalin-fixed, paraffin-embedded tissues using 5' nuclease quantitative RT-PCR. *J. Mol. Diagn.*, 2: 84–91, 2000.; Tassone, F., Hagerman, R. J., Taylor, A. K., Gane, L. W., Godfrey, T. E., and Hagerman, P. J. Elevated Levels of FMR1 mRNA in carrier males: a new mechanism of involvement in the fragile-X syndrome. *Am. J. Hum. Genet.*, 66: 6–15, 2000). All QRT-PCR assays were carried out at two RNA inputs, 400 and 100 ng, and duplicate reactions were set up for each concentration. Thus, the reported CEA expression levels are an average of four independent QRT-PCR reactions. RT-negative controls were run for all samples using 400 ng of RNA but omitting the reverse transcriptase. Template-negative controls were also run on each PCR plate. A calibrator RNA sample was amplified in parallel on all plates to allow comparison of samples run at different times (Godfrey, T. E., Kim, S.-H., Chavira, M., Ruff, D. W., Warren, R. S.,Gray, J. W., and Jensen, R. H. Quantitative mRNA expression analysis from formalin-fixed, paraffin-embedded tissues using 5' nuclease quantitative RT-PCR. *J. Mol. Diagn.*, 2: 84–91, 2000.; PE Applied Biosystems user bulletin #2. Relative quantitation of gene expression, Perkin-Elmer, Corp., Norwalk, Conn., 1997.).

For maximum sensitivity and to eliminate the risk of cross contamination, a single-tube QRT-PCR procedure described previously was used (Raja, S., Luketich, J. D., Ruff, D. W., Kelly, L. A., and Godfrey, T. E. A Method for increased sensitivity of one-step quantitative RT-PCR. *Biotechniques*, 29: 702–705, 2000). In this procedure, physical separation of the reverse transcription reaction mixture (RT) and the PCR primers using a wax layer results in a more specific and sensitive RT-PCR. The PCR primers were pipetted into the PCR plate in a 10 μl volume. One Ampliwax PCR gem 50 (Applied Biosystems) was then placed in each well, and the plate was heated to 80° C. for 2 min and cooled to 4° C. to produce the wax barrier. A 40 μl upper layer was then pipetted into each well. The final concentrations of the reaction components were as follows: 1× PCR buffer A, 300 nM each deoxynucleotide triphosphate, 3.5 mM $MgCl_2$, 0.4 unit/μl RNase Inhibitor, 1.25 units/μl Superscript II reverse transcriptase (Life Technologies, Inc., Gaithersburg, Md.), 0.06 unit/μl Amplitaq Gold (Applied Biosystems), 20 nM reverse transcriptase primer, 200 nM of each PCR primer, 200 nM probe (β-Gus primers and probe were at 100 nM), and 100 or 400 ng total RNA. The oligonucleotide sequences used are shown in Table 3. All RT-PCR reactions were carried out on the ABI 7700 with the following thermocycler conditions: 48° C. hold for 40 min, 95° C. hold for 12 min followed by 45 cycles of 95° C. for 15 s, and 64° C. (60° C. for β-gus) for 1 min. Data were analyzed using Sequence Detection Software (Applied Biosystems) with thresholds set at 0.03 for CEA and 0.045 for β-gus.

TABLE 3

Oligonucleotide sequences used for CEA and-Gus RT-PCR

| Oligonucleotide | B-Gus | CEA |
| --- | --- | --- |
| Forward primer | CTCATTTGGAATTTTGCCGATT (SEQ ID NO: 3) | AGACAATCACAGTCTCTGCGG (SEQ ID NO: 6) |
| Reverse primer | CCGAGTGAAGATCCCCTTTTTA (SEQ ID NO: 4) | ATCCTTGTCCTCCACGGGTT (SEQ ID NO: 7) |
| RT primer | TGGTTGTCTCTGCCGA (SEQ ID NO: 15) | GTGAAGGCCACAGCAT (SEQ ID NO: 9) |
| Probe* | TGAACAGTCACCGACGAGAGTGCTGG (SEQ ID NO: 5) | CAAGCCCTCCATCTCCAGCAACAACT (SEQ ID NO: 8) |

*TaqMan probes were labeled with 5' 6-carboxyfluorescein and 3' 6-carboxytetramethylrhodamine.

Gel-based RT-PCR Analysis: To avoid the possibility of PCR product contamination, all PCR plates from QRT-PCR runs were stored unopened until the quantitative analyses were complete. PCR products from the two 400 ng RNA input reactions and the 400 ng No-RT control were then separated on a 4% agarose gel, stained with ethidium bromide, and visualized on a gel documentation system. Patients were classified as RT-PCR positive if a correctly sized band was observed in both of the duplicate reactions but not in the No-RT control.

Statistical Analysis: Comparisons of CEA levels in control tissues samples (FIG. 6) were conducted with the Mann-Whitney U Test. For pathologically negative lymph nodes from esophageal cancer patients, the primary end point was disease recurrence measured from the time of surgery to the time of diagnosed recurrence or last date of follow-up. The highest CEA levels from each patient's tissue blocks were used to construct a ROC curve using recurrence as the gold standard. The CEA expression level cutoff value was identified that produced the most accurate classification, and that level was used to classify patients as QRT-PCR positive or negative for risk of recurrence. Because a second set of patients was not available for prospective validation of the cutoff, the cutoff selection procedure was evaluated statistically by cross validation, and the SDs of ROC curve statistics were calculated by bootstrap resampling (Davison, A. C., and Hinkley, D. V. Bootstrap Methods and Their Applications. Cambridge, United Kingdom: Cambridge University Press, 1997). Kaplan-Meier disease-free and overall survival curves were plotted for clinical and pathological factors including standard RT-PCR and QRT-PCR results. The analysis of disease-free survival was conducted by log-rank tests, and multivariate analysis was performed by constructing Cox proportionate hazards models. The list of predictors included categorical factors gender, tumor pathology, classification by RT-PCR and QRT-PCR, preoperative chemotherapy and/or radiotherapy, and pathological T stage, as well as quantitative factors of CEA expression level, age, and number of nodes removed for examination. All comparisons between models were based on differences between likelihood ratio tests for nested models. The adequacy of the proportional assumption was checked two ways: by plotting the log cumulative hazard by log time and by plotting Schoenfeld residuals and estimating the correlation between the regression coefficient and time.

RESULTS - Characteristics of Node-negative Patients: TNM classification of the 30 patients with node-negative esophageal cancer included $T_1N_0M_0$ (n=10), $T_2N_0M_0$ (n=5), and $T_3N_0M_0$ (n=10). One patient with biopsy diagnosed cancer had no evidence of cancer on the resection specimen, and four patients who received neoadjuvant therapy had no detectable tumor remaining at the time of resection. The location of the primary tumor included 25 lower third, 5 mid, and 0 upper esophageal sites. There were 26 adeno and 4 squamous cell cancers. There were 22 males and 8 females, and the median age of the patients at diagnosis was 70 years. Seventeen of the 30 patients have died, 10 from their cancers and 7 from other causes. For surviving patients, the median follow-up was 49 months (range, 28–91 months). The median overall survival was 36 months. A full breakdown of patient characteristics is provided in Table 4, below.

Figure 6:
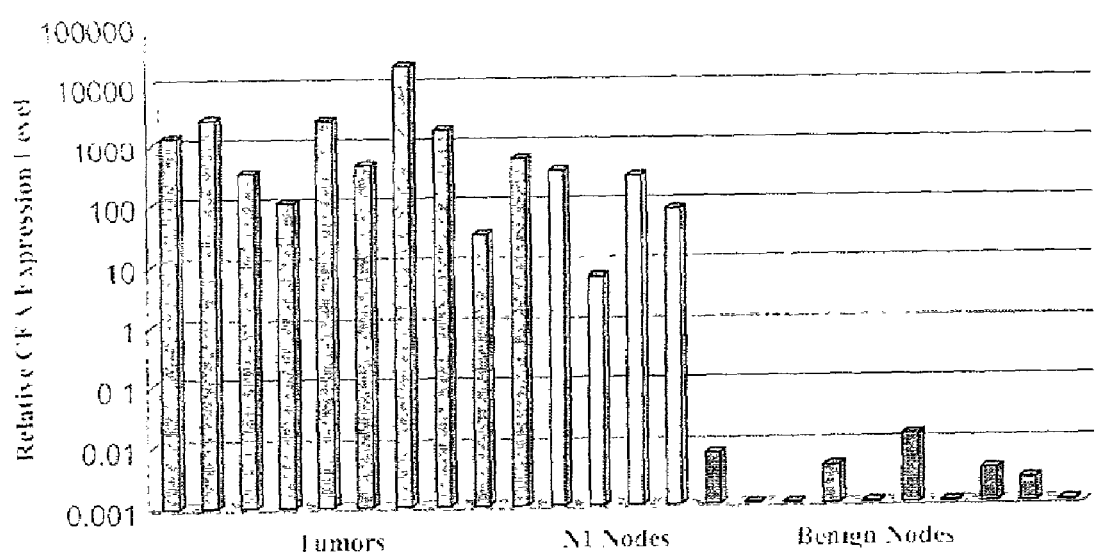
FIG. 6 is a graph showing the relative CEA expression measured in 10 esophageal tumors (light gray), 4 histologically positive ($N_1$) lymph nodes (white), and 10 benign lymph nodes from patients without cancer (dark gray).

Quantitative Analysis of CEA Expression: Initially, RNA was isolated and analyzed from three sources, distinct from the node-negative study group, and included primary esophageal tumors, lymph nodes that were histologically positive for metastases ($N_1$), and benign lymph nodes from patients without cancer. CEA expression was detected in all tumors, and $N_1$ nodes and in 50% of benign lymph nodes (FIG. 6). Individual, pairwise comparisons were carried out using a Mann- Whitney U test, and expression levels in both tumor and $N_1$ nodes were found to be significantly higher than in benign lymph nodes (P=0.002 and 0.0021, respectively). CEA expression was slightly higher in tumor samples than in $N_1$ lymph nodes, but this was not statistically significant (P=0.171).

Figure 7:
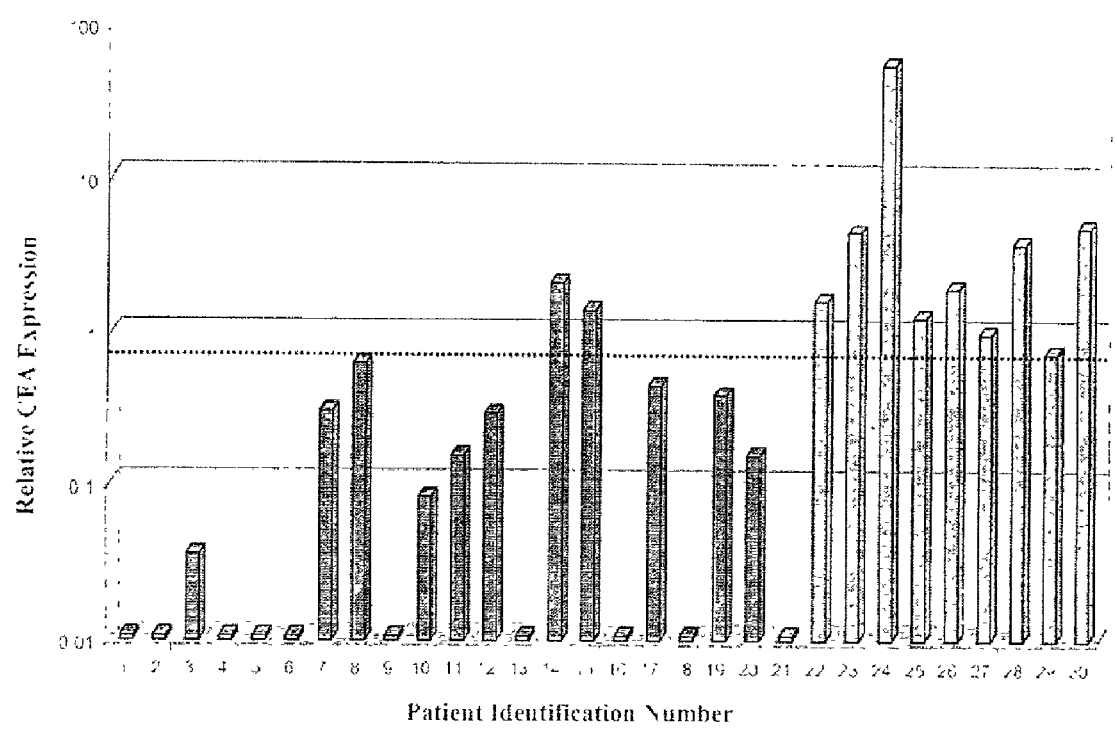
FIG. 7 shows the Relative CEA expression measured in histologically negative lymph nodes from 30 esophageal cancer patients. Graph shows the highest CEA level found for each patient. Patients 1–20 (dark gray columns) did not recur, whereas patients 21–30 (light gray columns) did recur. The dotted line indicates the most accurate cutoff value for predicting recurrence. Using this cutoff, QRT-PCR correctly classified 90% of patients with respect to disease recurrence at 3 years.
Figure 8A:
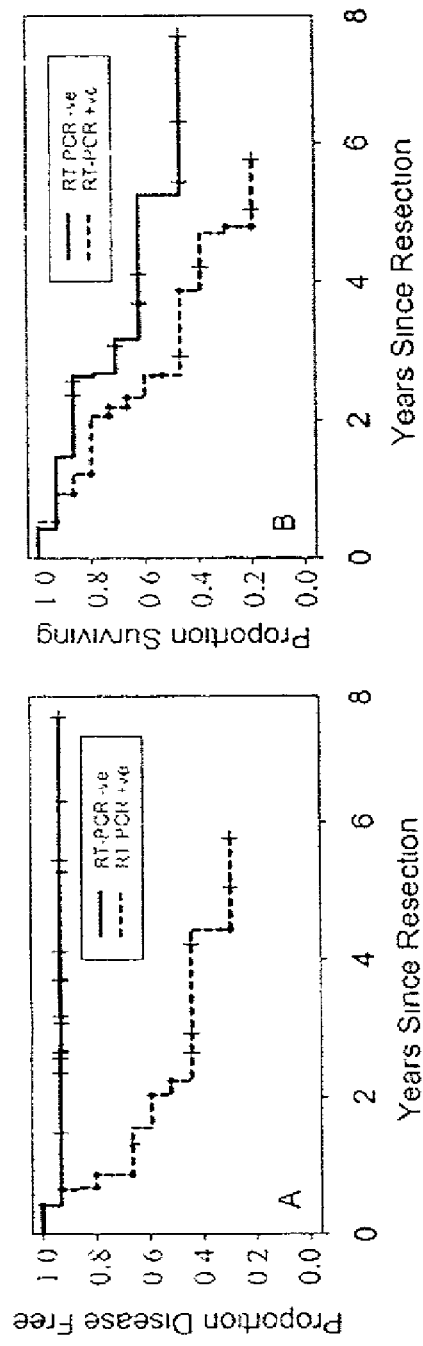
FIGS. 8A–D are Kaplan-Meier survival curves for disease-free survival for patients classified by RT-PCR (8A and 8B) and QRT-PCR (8C and 8D). Although log-rank tests indicate that both predictors are statistically significant, the superior specificity of QRT-PCR compared with RT-PCR leads to a greater ability to differentiate patients on the basis of their risk of recurrence (P=0.0038 for RT-PCR and <0.0001 for QRT-PCR).
Figure 8B:
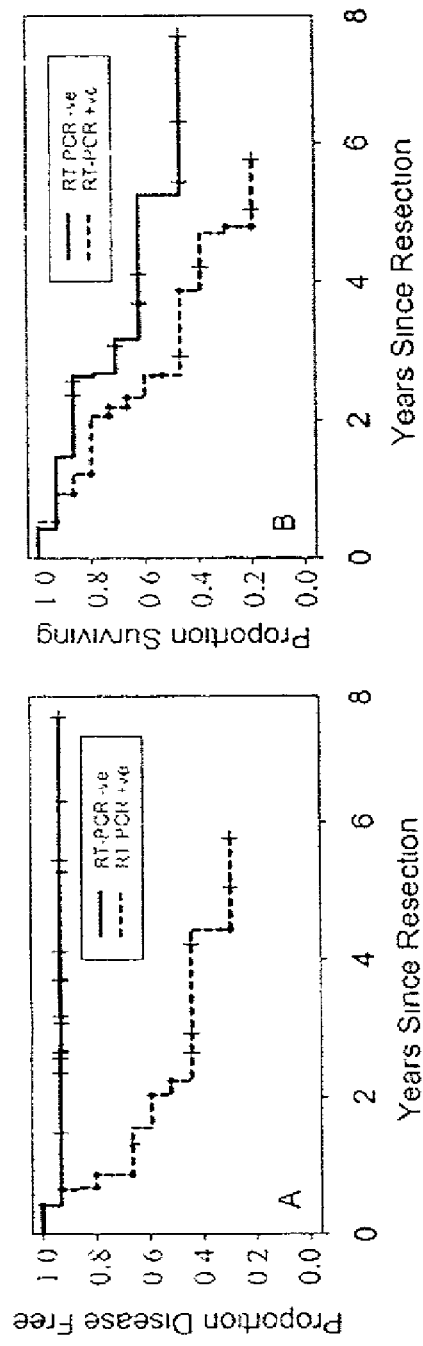
Figure 8C:
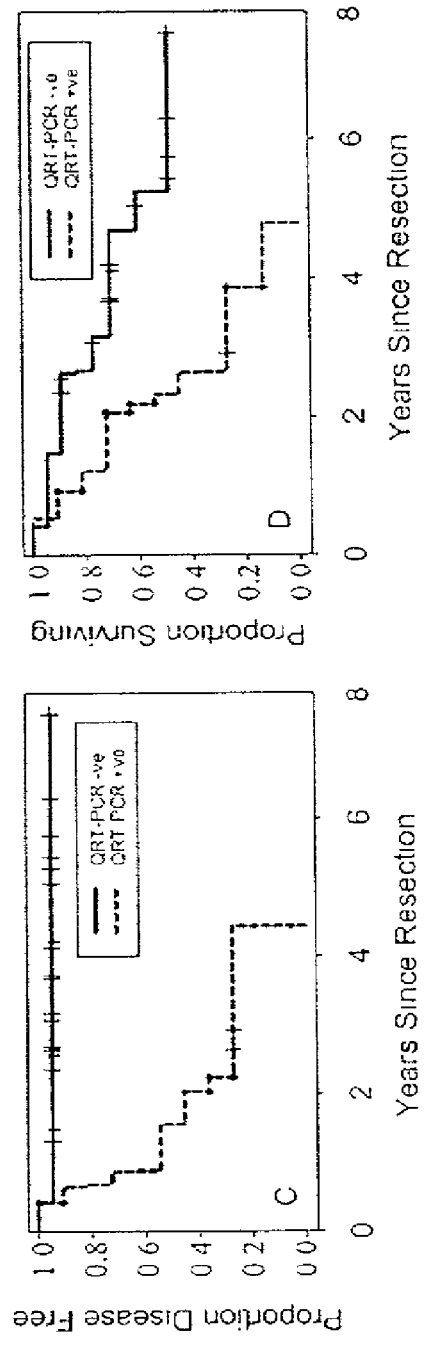
Figure 8D:
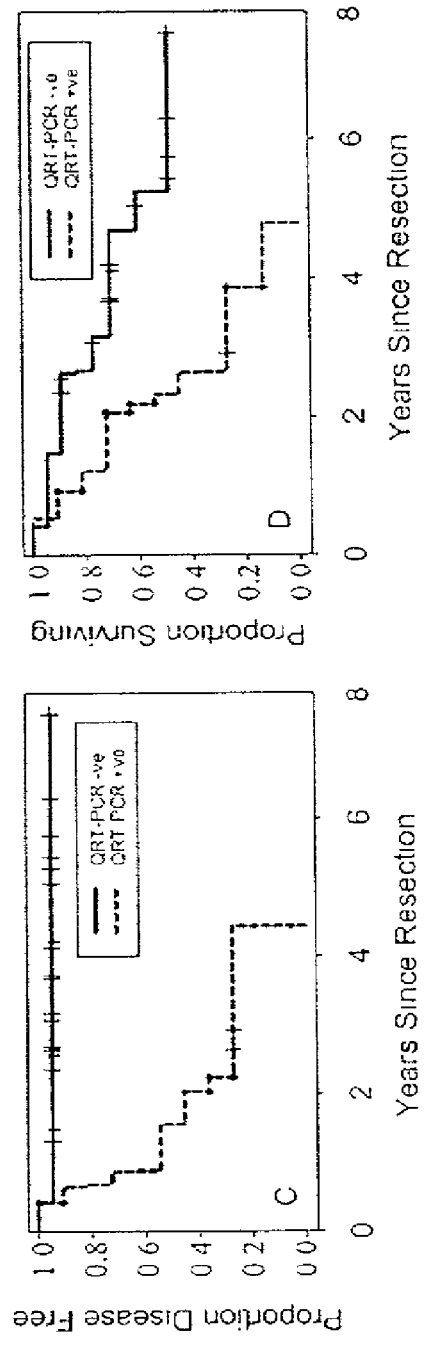

Analysis of histologically negative ($N_0$) lymph nodes from the study group demonstrated a wide range of CEA expression. Expression ranged from undetectable to one node with CEA expression equal to that seen in histologically positive lymph nodes. Data from the most highly expressing node from each patient, in conjunction with disease recurrence information, were analyzed using a ROC curve analysis. From this analysis, an expression level cutoff that most accurately predicted recurrence was determined (FIG. 7). The area under the ROC curve was 0.88 with a 95% confidence of 0.71 to 0.97, indicating that classification accuracy is significantly better than chance alone. Of the 140 tissue blocks analyzed, 12 (9%) had CEA expression levels above the cutoff point, and a total of 11 patients (34%) had one or more blocks with expression above the cutoff. These 11 patients were classified as having QRT-PCR evidence of occult micrometastases. Sections from all but 1 (patient 28) of the "most positive" tissue blocks were negative for immunohistochemical staining with antibodies against CEA.

Gel-based Analysis of CEA Expression: A total of 25 (18%) tissue blocks were positive for CEA expression using the gel-based assay, and 15 (50%) patients had at least one positive block in this analysis. In 2 of the 10 lymph nodes from patients with benign disorders, a CEA PCR product was present on the gel-based assays. A comparison of the quantitative and gelbased assays showed that all samples positive on gels also gave signals in the TaqMan assay.

Occult Metastases and Recurrence: Of the 30 patients studied, 10 suffered disease recurrence and died by the end of the study. Of the remaining 20 patients, 7 died from other causes and 13 remain alive with no evidence of recurrent disease. One patient suffered an early anastomatic recurrence that was treated with photodynamic therapy and radiotherapy. This patient was later diagnosed with, and died of, small cell lung cancer. Using the most accurate cutoff for the quantitative assay, a total of 11 patients were classified as QRT-PCR positive, and 9 of these suffered recurrence. The same 9 patients were identified as RT-PCR positive using the gel-based assay, along with 6 other patients who did not recur. Sensitivity and specificity for predicting disease recurrence using the QRT-PCR assay was 90 and 90%, with a positive predictive value of 82%. Using the gelbased assay, the sensitivity and specificity were 90 and 70% with a positive predictive value of 60%. FIG. 8 shows disease-free survival for the patient cohort classified by RT-PCR (A) and QRT-PCR (C) as well as overall survival (B and D). Disease-free survival of patients who were RT-PCR negative was 94% when using either assay. Patients with a positive classification had poorer prognosis by either method. The log-rank test indicates that both QRT-PCR (P=0001) and gel-based RT-PCR (P=0038) are significant predictors of recurrence in node-negative esophageal cancer patients. Overall survival was also worse in QRT-PCR- or RT-PCR-positive patients (P=0.0006 and 0.106, respectively).

Besides QRT-PCR and RT-PCR, the only other clinical, pathological, or treatment factors found to predict disease recurrence in this cohort were pathological T stage (log-rank test, P=0.0777) and preoperative chemotherapy and/or radiotherapy (log rank test, P=0.0307). In a multivariate analysis, the likelihood ratio statistics from Cox regression models showed that the classification of CEA as a binary variable, QRT-PCR positive or negative, was a significant and independent predictor of recurrence when compared with pathological T stage and preoperative chemotherapy or radiotherapy.

Discussion

Lymph node involvement is the strongest prognostic factor in many solid tumors, and detection of lymph node micrometastases has received much interest in the recent literature. Current lymph node evaluation involves microscopic examination of H&E-stained tissue sections and suffers from two major limitations: (a) single tumor cells, or small foci of cells, are easily missed; and (b) only one or two tissue sections are studied, and thus the vast majority of each node is left unexamined. Serial sectioning can overcome the issue of sampling error, and IHC can identify individual tumor cells. The combination of these methods, however, is too costly and time consuming for routine analysis and is limited to special cases such as sentinel lymph node examination. RT-PCR overcomes the problem of sampling error because larger amounts of tissue can be analyzed, and several reports indicate that RT-PCR identifies more positive lymph nodes than IHC. This was also the case in the present study, where only one of the QRT-PCR- positive lymph node blocks was positive by IHC analysis.

Recent studies also show that non-QRT-PCR positivity correlates with disease recurrence, but the specificity reported in these studies is low. In one study by Liefers et al. (13. Liefers, G. J., Cleton-Jansen, A. M., van de Velde, C. J., Hermans, J., van Krieken, J. H., Cornelisse, C. J., and Tollenaar, R. A. Micrometastases and survival in stage II colorectal cancer [see comments]. N. Engl. J. Med., 339: 223–228, 1998.), 14 of 26 histologically $N_0$ colon cancer patients had evidence of micrometastatic disease using RT-PCR, and the remaining 12 were RT-PCR negative. Of the 12 RT-PCR $N_0$ patients, only 1 recurred during the 6-year follow-up period, whereas of the 14 RT-PCR $N_1$ patients, 7 suffered recurrence. Thus, using recurrence as an end point, this study achieved a sensitivity of 88%. The specificity, however, was only 61%, because 7 patients with RT-PCR-positive nodes did not recur. Other studies have shown a similar low specificity for non-QRT-PCR in melanoma patients. Shivers et al. (Shivers, S. C., Wang, X., Li, W., Joseph, E., Messina, J., Glass, L. F., DeConti, R., Cruse, C. W., Berman, C., Fenske, N. A., Lyman, G. H., and Reintgen, D. S. Molecular staging of malignant melanoma: correlation with clinical outcome. JAMA, 280: 1410–1415, 1998) achieved 86% sensitivity and 51% specificity, and Bostick et al. (Bostick, P. J., Morton, D. L., Turner, R. R., Huynh, K. T., Wang, H. J., Elashoff, R., Essner, R., and Hoon, D. S. Prognostic significance of occult metastases detected by sentinel lymphadenectomy and reverse transcriptase-polymerase chain reaction in early-stage melanoma patients. J. Clin. Oncol., 17: 3238–3244, 1999) reported 100% sensitivity and 67% specificity. This low specificity, along with an inability to accurately control for inter-run variability, has limited the potential of RT-PCR in a clinical setting.

In the current study, the use of TaqMan RT-PCR to quantitatively assay CEA expression and detect occult micrometastases in lymph nodes of histologically $N_0$ esophageal cancer patients was evaluated. This quantitative analysis resulted in the definition of a clinically relevant CEA expression level cutoff and the overcoming of the problems associated with background, or ectopic, CEA expression reported by others. Using this approach, 11 of 30 patients were identified as being QRT-PCR positive, and 9 of these patients suffered disease recurrence. Only 1 of the 19 patients who were QRT-PCR negative suffered recurrence during the course of this study. Interestingly, of the 20 patients who did not recur, 11 had detectable CEA expression higher than that seen in control lymph nodes (higher than background levels), and two were above the cutoff level for predicting disease recurrence. In some cases, this could indicate the presence of limited nodal disease that was cured by surgery, because even $pN_1$ patients can have an expected 5-year survival of ~20%. CEA expression in the remaining samples could possibly be a result of either individual disseminated tumor cells that are unable to survive and are possibly undergoing apoptosis, cell-free RNA in the lymph system as a result of tumor cell apoptosis at the primary site, or contaminating cells introduced inadvertently by the surgeon.

Both disease-free survival and overall survival were significantly higher in the QRT-PCR-negative patients compared with QRT-PCR-positive patients. Furthermore, disease-free survival in the QRT-PCR-positive group was only 27% at 3 years, indicating that micrometastatic disease may be as clinically significant as histological $N_1$ disease. With the exception of one patient, only one positive tissue block was identified per patient, indicating limited disease spread. All positive lymph nodes were locoregional and would therefore confer $N_1$ status, rather than $M_{1a}$, as defined by celiac or cervical lymph node involvement. The limited nodal involvement in these histologically $N_0$ patients emphasizes the need for adequate lymph node sampling, from different nodal stations, during staging procedures.

Although the subset of patients with node-negative disease has been relatively small in the past, the dramatic increase in esophageal cancer has led to surveillance programs that are identifying patients with early stage disease more frequently. Methods for accurate staging of these patients will thus become even more important. Comparison herein of the quantitative data with gel-based analysis of the same samples showed that QRT-PCR improves the test specificity while maintaining the same high sensitivity. QRT-PCR also gives objective results, which are amenable to automated, hands-free analysis, with minimal risk of PCR product cross-contamination. Such automation will be essential if QRT-PCR is to become a routine clinical assay.

In addition, the quantitative procedure allows for use of rigorous controls to confirm the accuracy and reliability of the assay from run to run. For example, in the described experiments, a calibrator sample was run on all PCR plates to correct for day to day variability. Using this methodology, reproducibility tests indicate that the 95% confidence limits on measurements are 0.511 cycles (data not shown). The ability to accurately assess the reproducibility of the quantitative assay will be essential if RT-PCR is to be used in a clinical setting. In a gel-based assay, this level of assay verification is not attainable. It is acknowledged that the predictive ability of classifying patients by their CEA levels determined by QRT-PCR will be optimistic because the cutoff value was evaluated in the same patients in whom it was determined. It is likely that if the same procedure for the most accurate cutoff were applied to a second set of patients, the classification would be less successful. To this end, a reanalysis of the sensitivity, specificity, and classification accuracy was conducted by cross-validation (n=10000). The cross-validation estimates of specificity were 0.82 and accuracy of 0.82 (compared with 0.90 and 0.90, respectively, in the original sample). Thus, the classification success of the original sample was slightly overstated, but even after correction for this optimism, classification by QRT-PCR remains an improvement over the gel-based assay.

In conclusion, these data demonstrate that QRT-PCR can detect, with high specificity, micrometastatic disease in histologically negative lymph nodes of esophagus cancer patients. It also has been shown that the presence of micrometastatic disease is a strong, independent predictor of cancer recurrence and that quantitation is superior to standard RT-PCR assays. Quantitative RT-PCR should be able to identify which patients with early stage esophageal cancer are at high risk for recurrence and who might benefit from additional therapy. Finally, this quantitative approach should result in similar benefits in other tumor types.

TABLE 4

Survival and RT-PCR data of individual patients

| Patient ID | T stage | Adjuvant therapy | | Outcome | | Survival | | CEA status | |
|---|---|---|---|---|---|---|---|---|---|
| | | Chemotherapy | Radiation | Vital Status | Disease status[a] | Overall | Disease Free | QRT-PCR | RT-PCR |
| 1 | 2 | None | None | Alive | NED | 43.9 | 43.9 | − | − |
| 2 | 1 | None | None | Alive | NED | 28.4 | 28.4 | − | − |
| 3[b] | 1 | Post | Post | Alive | NED | 30.8 | 30.8 | − | − |
| 4 | 1 | Pre | None | Dead | Other | 17.8 | 17.8 | − | − |
| 5 | 1 | None | None | Alive | NED | 90.6 | 90.6 | − | − |
| 6 | 3 | Pre | None | Alive | NED | 60.6 | 60.6 | − | + |
| 7 | 1 | None | None | Alive | NED | 50.5 | 50.5 | − | + |
| 8 | 2 | None | None | Alive | NED | 75.6 | 75.6 | − | − |
| 9 | 1 | None | None | Dead | Other | 38.1 | 38.1 | − | − |
| 10 | 3 | Pre | None | Alive | NED | 69.1 | 69.1 | − | + |
| 11 | 2 | None | None | Alive | NED | 44.6 | 44.6 | − | − |
| 12 | 3 | Pre | Pre | Dead | Other | 31.7 | 31.7 | − | − |
| 13 | 1 | None | None | Dead | Other | 63.1 | 63.1 | − | − |
| 14[b] | 0[c] | Pre | Pre | Alive | NED | 35.0 | 35.0 | + | + |
| 15[b] | 1 | None | None | Dead | Other | 31.8 | 31.8 | + | + |
| 16 | 0[d] | None | None | Alive | NED | 49.4 | 49.4 | − | − |
| 17 | 2 | None | None | Alive | NED | 36.9 | 36.9 | − | − |
| 18 | 1 | None | None | Alive | NED | 65.2 | 65.2 | − | − |
| 19 | 0[c] | Pre | None | Dead | Other | 56.3 | 15.8 | − | + |
| 20 | 3 | Pre | Pre | Dead | Other | 32.2 | 32.2 | − | − |
| 21 | 3 | None | None | Dead | NED | 5.0 | 5.0 | − | − |
| 22 | 3 | Pre | None | Dead | Recurred | 24.8 | 24.3 | + | + |
| 23 | 1 | Pre | None | Dead | Recurred | 57.4 | 53.0 | + | + |
| 24 | 3 | Pre | None | Dead | Recurred | 28.0 | 7.9 | + | + |
| 25[b] | 3 | None | None | Dead | Recurred* | 6.3 | 5.0 | + | + |
| 26 | 3 | Pre | Pre | Dead | Recurred | 11.1 | 10.6 | + | + |
| 27 | 2 | Pre | Pre | Dead | Recurred | 14.6 | 10.4 | + | + |
| 28 | 0[c] | Pre | Pre | Dead | Recurred | 46.4 | 8.3 | + | + |
| 29 | 3 | Pre | Pre | Dead | Recurred | 26.3 | 18.7 | + | + |
| 30 | 0[c] | Pre | Pre | Dead | Recurred | 31.9 | 27.0 | + | + |

[a]NED, no evidence of disease.
[b]Patients with squamous cell carcinoma.
[c]Patients who had no residual tumor after chemotherapy.
[d]Patient with cancer on biopsy, but not at resection.

Example 5

Intra-operative Quantitative RT-PCR Detects Nodal Metastasis in Patients with Esophageal Cancer

Introduction

Surgical decisions in esophageal cancer and other malignancies are often based on intra-operative frozen section analysis of lymph nodes. The 5-year survival of patients with esophageal cancer remains poor at 5–10% due to the presence of advanced disease in many patients at the time of initial presentation. If local and regional lymph nodes are histologically negative however, there is a dramatic improvement in the 5-year survival. Nevertheless, 30–50% of histologically node negative patients suffer disease recurrence. This is most likely due to the limitations of current staging techniques in the detection of micrometastases. As a result, other techniques such as immunohistochemistry or reverse transcriptase-polymerase chain reaction (RT-PCR) have been used in attempts to detect histologically occult micrometastases.

Studies on esophagus, colon, melanoma and breast cancers have shown that RT-PCR can detect histologically occult micrometastases, and may predict recurrence. These data have been criticized however, due to the occurrence of false positive results in control samples and the subsequent low specificity and positive predictive value of the RT-PCR assay. It has been shown that Quantitative RT-PCR (QRT-PCR) allows the distinction of background, ectopic, gene expression from true micrometases and can therefore avoid false positives and increase specificity for predicting disease recurrence. The next goal is to be able to provide the surgeon with this critical information at a time when important surgical decisions are made, intra-operatively.

Described in this Example is the development and testing of an extremely rapid QRT-PCR assay that can be carried out in less than 30 minutes. To validate the rapid assay, it is compared to standard QRT-PCR and to clinical outcomes in patients with esophageal cancer.

Materials and Methods

Patients

For the retrospective analysis, lymph nodes were studied from 30 patients (Table 6) who underwent curative resection for histologically lymph node-negative esophageal cancer. All surgeries were performed in the Division of Thoracic Surgery at the University of Pittsburgh Medical Center between 1991 and 1998. Clinical follow up was obtained from the medical records and was confirmed for all patients as of August 2001. The median clinical follow up time for all patients was 36 months and for the surviving patients was 49 months (range 28–91 months).

TABLE 6

Clinical Characteristics of the study population.

|  | | QRT-PCR Result | |
| --- | --- | --- | --- |
| Characteristic | Patients (n = 30) | Negative (n = 17) | Positive (n = 13) |
| Gender | | | |
| Male | 22 | 14 | 8 |
| Female | 8 | 3 | 5 |

TABLE 6-continued

Clinical Characteristics of the study population.

|  | | QRT-PCR Result | |
| --- | --- | --- | --- |
| Characteristic | Patients (n = 30) | Negative (n = 17) | Positive (n = 13) |
| Months follow up | | | |
| Median | 36 | 43.9 | 31.8 |
| Range | 5–90.5 | 5–90.5 | 6.3–75.6 |
| Mean Age at Diagnosis | 68.3 | 68.4 | 68.2 |
| Tumor Type | | | |
| Adenocarcinoma | 26 | 16 | 10 |
| Squamous cell | 4 | 1 | 3 |
| Stage* | | | |
| 0† | 1 | 1 | 0 |
| I | 10 | 8 | 2 |
| IIA | 15 | 8 | 7 |
| Median Number of Nodes examined | 12.5 | 12 | 15 |

*4 patients who received chemotherapy had no tumor at time of surgery.
†1 patient had cancer on biopsy but not at resection.

For the prospective analysis, lymph node samples were obtained from 12 patients undergoing either staging or resection for esophageal cancer identified by the Section of Thoracic Surgery at the University of Pittsburgh Medical Center from 1999 to 2000 (Table 7). Control nodes from patients without cancer were obtained incidentally from patients undergoing abdominal surgery for anti-reflux procedures. At th time of excision, one half of each lymph node was frozen in liquid nitrogen for analysis and the reminder was sent for routine pathological analysis. The exercise tissue was part of the routine clinical course at our institutional and, as such, no additional tissue was removed for any purely research purpose. All tissues were collected as part of an ongoing, TRB approved, Esophagus Cancer Risk Registry protocol at the University of Pittsburgh.

TABLE 7

Tumor stage and histology for patients in the rapid QRT-PCR study on fresh frozen lymph nodes.

| Patient | stage | Tumor Type |
| --- | --- | --- |
| 12 | IIA | adeno |
| 13 | IIA | adeno |
| 14 | I | adeno |
| 15 | IIA | adeno |
| 16 | IIA | adeno |
| 17 | IIA | squamous |
| 18 | III | adeno |
| 19 | III | adeno |
| 20 | III | adeno |
| 21 | III | adeno |
| 22 | III | adeno |
| 23 | III | adeno |

Tissue and RNA Isolation

All tissues used in the retrospective study were foramalin-fixed, paraffin-embedded archival specimens obtained from the Pathology tissue banks. Hematoxylin and eosin stained slides were also retrieved for each tissue block and were examined to confirm the original node-negative diagnosis. Tissue blocks were mounted on a microtome and 5–15, 5.0

μM sections were cut and placed in 2.0 ml RNase free tubes. At the same time, 2, 5.0 μM sections were cut (first and last sections) and mounted on microscope slides for H&E staining as well as immunohistochemical staining with antibodies against CEA. RNA was isolated using previously described methods (Godfrey TE, Kim S-H, Chavira M, Ruff DW, Warren RS, Gray JW et al. Quantitative mRNA expression analysis from formalin-fixed, paraffin-embedded tissues using 5' nuclease quantitative RT-PCR. *Journal of Molecular Diagnostics* 2000; 2(2):84–91.) and quantitated spectrophotometrically.

The fresh frozen lymph node tissues were embedded in OCT compound and 10–15, 4.0 μM sections were cut. At the same time, 2, 4.0 μM sections were cut (first and last sections) and mounted on microscope slides for H&E staining. The remaining sections were placed in 1.5 ml RNase free tubes with the lysis buffer from the RNeasy Mini kit (Qiagen, Valencia, Calif.). RNA was extracted using the manufacturers recommended protocol with the following modifications. Centrifugation times over 1 minute were reduced to 1 minute, and the RNA was reconstituted in 60 μl RNA secure resuspension solution (Ambion, Austin, Tex.). Although most of the samples were processed together, five samples were processed individually to determine the median extraction time per sample. The RNA yield and purity was determined spectrophotometrically for quality control purposes.

Quantitative Reverse Transcription-PCR

QRT-PCR was carried out using the 5' nuclease assay. Rapid QRT-PCR was carried out on the Cepheid Smart Cycler® (CSC) real-time DNA amplification and detection system as described below. Standard QRT-PCR was carried out on the Applied Biosystems 7700 Sequence Detection Instrument (TaqMan®) using a one-tube QRT-PCR procedure described herein.

Rapid QRT-PCR

CEA expression was measured relative to the endogenous control gene, β-glucuronidase (β-GUS) using the comparative $C_T$ method described previously (Godfrey TE, Kim S-H, Chavira M, Ruff DW, Warren RS, Gray JW et al. Quantitative mRNA expression analysis from formalin-fixed, paraffin-embedded tissues using 5' nuclease quantitative RT-PCR. *Journal of Molecular Diagnostics* 2000; 2(2):84–91.; Tassone F, Hagerman RJ, Taylor AK, Gane LW, Godfrey TE, Hagerman PJ. Elevated levels of FMR1 mRNA in carrier males: a new mechanism of involvement in the fragile X syndrome. *Am. J. Hum. Genet.* 2000; 66(1):6–15.). All QRT-PCR assays were carried out on 400ng of total RNA in triplicate. Both CEA and β-GUS PCR primers were designed and tested not to amplify genomic DNA. However, control reactions were still run using RNA without reverse transcription (NO-RT control) and water (no-template control) in place of cDNA as PCR template. Together these control reactions rule out the possibility that signal is generated from either genomic DNA contamination of the RNA, or PCR product contamination of the reagents. In addition, a calibrator RNA sample was amplified in parallel on all runs to allow comparison of samples run at different times(Godfrey et al. (2000); PE Applied Biosystems User Bulletin #2. ABI Prism 7700 Sequence Detection System: Relative Quantitaion of Gene expression. 1997. Norwalk, Conn., Perkin Elmer Corp.), and to determine reproducibility of the assay.

The final concentrations of the reaction components were as follows: 1× PCR Platinum Taq buffer, 300 nM each dNTP, 4.5 mM $MgCl_2$, 0.8U/μl RNase Inhibitor, 1.25μl Sensiscript reverse transcriptase (Qiagen, Valencia, Calif.), 0.06U/μl Platinum Taq (Gibco, Gaithersburg, Md.), 60 nM RT primer, 400 nM each PCR primer, 200 nM probe and 400 ng of total RNA. The total RNA input for the fresh tissue analysis was 5 μl of the sample. For the fixed tissue analysis, 5 μl of an 80 ng/μl dilution of the RNA stock was used. In the rapid assay, the RT reaction was carried out without the PCR primers or probe, then the tube was opened and the primers and probe were added. This was necessary because a standard one-step QRT-PCR lacked the sensitivity to detect rare messages. The oligonucleotide sequences used were as follows: β-GUS RT primer 5' TGG TTG TCT CTG CCG A 3' (SEQ ID NO:15), β-GUS forward PCR primer 5' CTC ATT TGG AAT TTT GCC GAT T 3' (SEQ ID NO: 3), β-GUS reverse PCR primer 5' CCG AGT GAA GAT CCC CTT TTT A 3' (SEQ ID NO:4), β-GUS probe 5'-Vic TGA ACA GTC ACC GAC GAG AGT GCT GG 3' (SEQ ID NO:5), CEA RT primer 5' GTG AAG GCC ACA GCA T 3' (SEQ ID NO:9), CEA forward PCR primer 5' AGA CAA TCA CAG TCT CTG CGG A 3' (SEQ ID NO:6), CEA reverse PCR primer 5' ATC CTT GTC CTC CAC GGG TT 3' (SEQ ID NO:7) and CEA probe 5'-Fam CAA GCC CTC CAT CTC CAG CAA CAA CT 3' (SEQ ID NO:8). Rapid QRT-PCR reactions were carried out on the CSC with the following thermocycler conditions; 48° C. hold for 5 minutes, 70° C. for 60 seconds (for the addition of the PCR primers and probe), 95° C. hold for 30 seconds (for Platinum Taq activation) followed by 45cycles of 95° C, for 2 seconds and 64° C. for 15 seconds. Data was analyzed with Smart-Cycler Software (Ver 1.0) using the second derivative method for determining the threshold. For the fixed tissue analysis, a 30 minute RT reaction was required because of the reduced sensitivity associated with the degradation inherent in fixed tissue RNA samples.

Statistical Analysis

The predictive validity of rapid QRT-PCR determination of CEA expression level was evaluated by proportionate hazards regression for disease-free survival. Disease-free survival was defined as the time from surgery to the time of diagnosed recurrence of esophageal cancer. Deaths due to other causes and patients alive without disease as of Aug. 1, 2001 were censored. CEA expression level was also used to classify patients as either QRT-PCR positive or negative. The cutoff level for classification, determined by ROC curve analysis (DeLong ER, DeLong DM, Clarke-Pearson DL. Comparing the areas under two or more correlated receiver operating characteristic curves: a nonparametric approach. *Biometrics* 1988; 44(3):837–845; Heagerty PJ, Lumley T, Pepe MS. Time-dependent ROC curves for censored survival data and a diagnostic marker. *Biometrics* 2000; 56(2): 337–344), was defined as the CEA expression level value that produced the most accurate classification using disease recurrence as the standard. Sensitivity and specificity of QRT-PCR results were calculated for diagnosing occult metastasis. Patients classified as QRT-PCR positive or negative based on the classification method were tested for differences in disease-free survival with the log rank test.

Results

Archived Tissue Analysis

Figure 9:
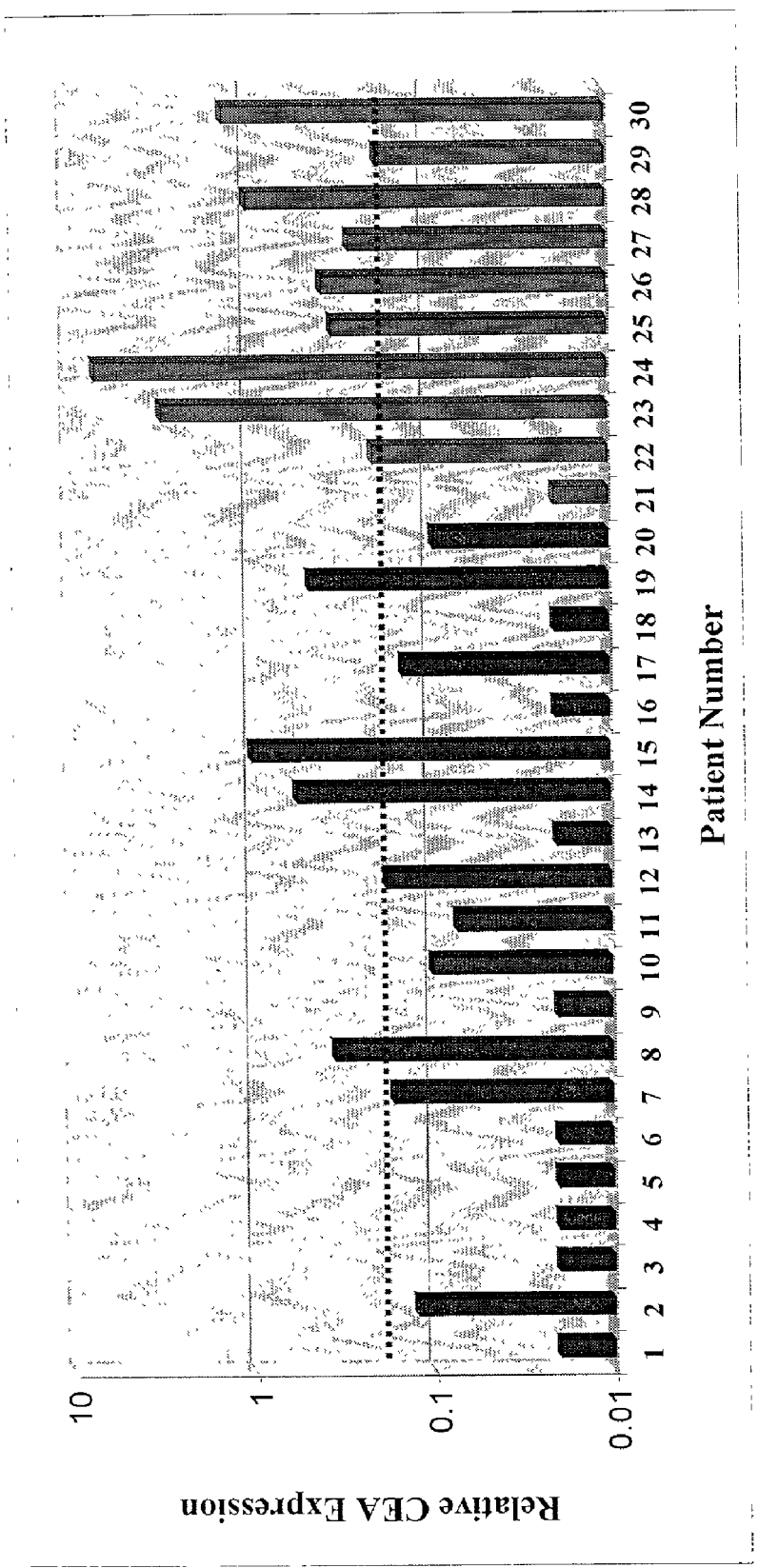
FIG. 9 shows a SmartCycler analysis of CEA expression in formalin-fixed lymph nodes from 30 pathologically node negative esophagus cancer patients. Gray bars (21–30) indicate patients who suffered recurrence, black bars (1–20) indicate patients who did not suffer recurrence. Lymph nodes with no detectable CEA expression have been arbitrarily plotted at a level of 0.02. The dotted line indicates the most accurate CEA expression cut-off value (0.183) for predicting disease recurrence.
Figure 10:
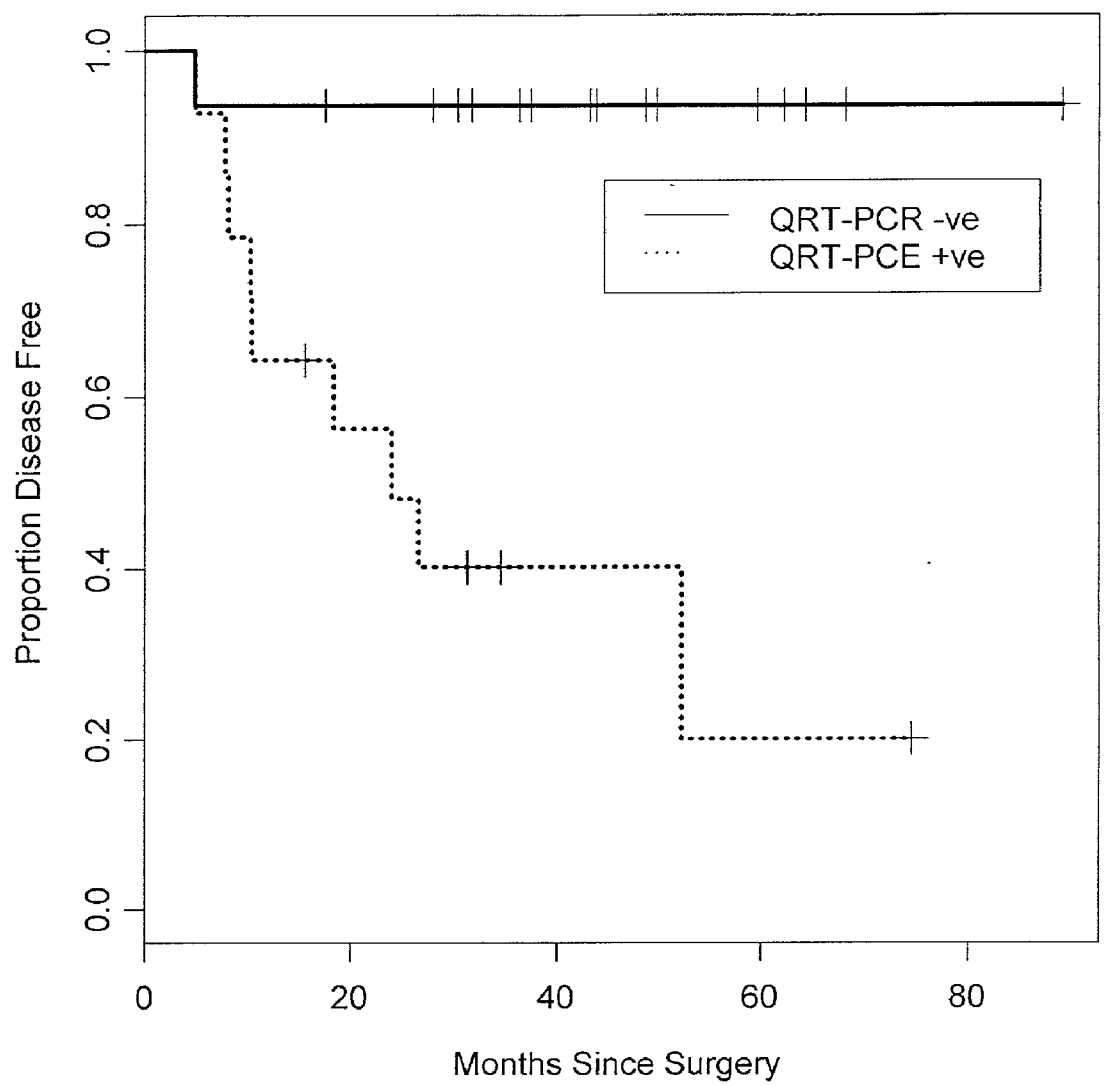
FIG. 10 shows a Kaplan-Meier disease free survival curve for 30 $pN_0$ esophagus cancer patients stratified as LN positive or negative (above or below the cut-off value of 0.183) based on Smartcycler QRT-PCR.

Initially, archived, histologically negative ($N_0$) lymph nodes from 30 patients with esophageal cancer were analyzed (FIG. 9). Of the 30 tissue blocks analyzed, 13 had CEA expression higher than the ROC curve determined cutoff (CEA expression greater than 0.183). In this group, 9 patients suffered disease recurrence and died by the end of the study, 2 patients have died from other causes and 2 are alive without disease. Of the remaining 17 QRT-PCR negative patients, 1 suffered disease recurrence at 5 months and died by the end of this study, 5 have died from other causes and 11 remain alive and disease free (Table 8). Using the rapid QRT-PCR assay, the sensitivity and specificity for predicting disease recurrence were 90% and 80% respectively and 83% of patients in the cohort were classified correctly. FIG. 10 shows the Kaplan-Meier disease-free survival curves for QRT-PCR positive and negative patients. Survival of patients who were QRT-PCR negative and positive was 94% and 20% respectively at 5 years. The survival functions for these two groups were significantly different (p=0.001, log rank test).

TABLE 8

Rapid QRT-PCR results on 30 pN0 esophagus cancer patients using a CEA expression cut-off of 0.183. Sensitivity was 90% (9/10) and specificity was 80%.

|  | Recurrence (true +ve) | No recurrence (true −ve) |
| --- | --- | --- |
| QRT-PCR positive | 9 | 4 |
| QRT-PCR negative | 1 | 16 |

Using the proportionate hazards model for disease free survival, the relative risk (RR) of an increase of one unit of CEA expression was 1.52 (1.11–2.09, p-0.027) and that of having CEA expression greater than 0.183 was 3.78 (1.34–10.7, p=0.0007) compared to CEA expression less than or equal to 0.183.

Fresh Tissue Analysis

Figure 11:
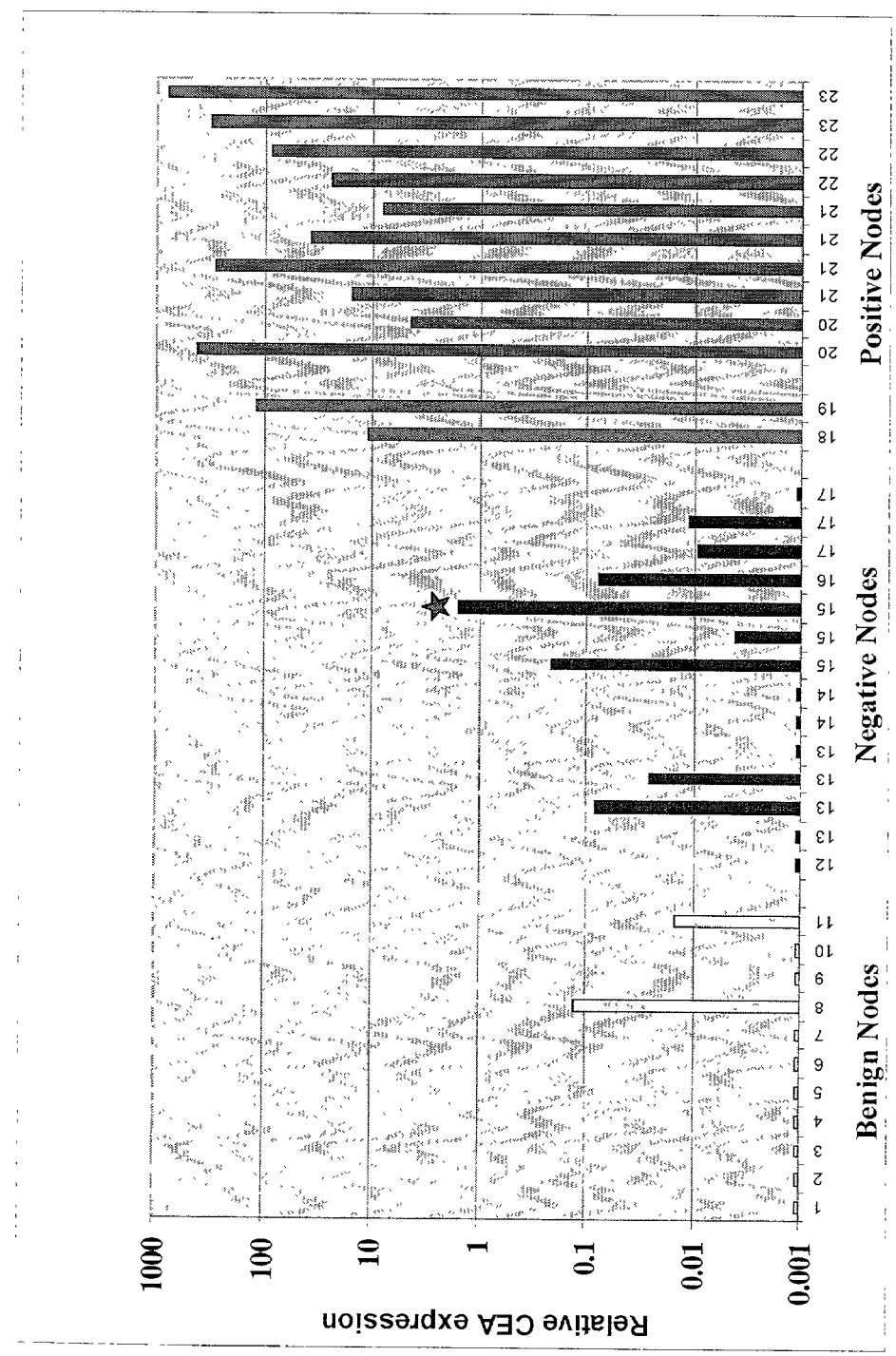
FIG. 11 shows Smartcycler analysis of CEA expression in frozen lymph nodes. White (1–11)=nodes from patients without cancer; black (12–17)=nodes determined on final pathology to be negative for disease; gray (20–23)=nodes found to be positive for disease; gray (18 and 19)=nodes that were negative by intra-operative frozen section but positive on fixed tissue histology; star =highly expressing node from a node negative patient who suffered disease recurrence. The value of 0.001 was arbitrarily assigned to all samples that had no detectable expression of CEA.

Fresh frozen sections of lymph nodes from patients undergoing minimally invasive staging for esophageal cancer, or benign esophageal disorders, were analyzed. In the 11 lymph nodes from the benign cases, rapid QRT-PCR detected very low levels of CEA expression in only 2 lymph nodes (patients 8 and 11, FIG. 11). This low level in the benign cases presumably represented background, ectopic CEA expression. The highest level of CEA expression in any benign node was 34-fold lower than the lowest expressing positive node (FIG. 11), which had only a small focus of tumor involvement.

Of the 26 lymph nodes from 12 patients with esophageal cancer, 12 (6 patients) were ultimately shown to be positive on final pathology. In 2 (2 patients) of these lymph nodes however, intra-operative frozen section analysis was negative and $N_1$ status was determined post-operatively. Rapid QRT-PCR showed CEA expression levels in these 2 nodes to be in the range of the histologically positive nodes (patient 18 and 19, FIG. 11). In the 6 patients who had histologically node negative esophageal cancer, only one had a single node with increased CEA expression by rapid QRT-PCR (patient 15, FIG. 11). This patient had a clinical recurrence of his esophageal cancer at a follow-up of 16.5 months.

Analysis of the calibrator samples on each run revealed that, over 13 separate runs, the standard deviation of the delta Ct value was 0.14 cycles (~10% standard deviation of relative expression measurements). Additionally, the QRT-PCR required approximately twenty-five minutes for all 40-cycle runs. With an RNA isolation time of 7 minutes, the entire assay takes around 30 minutes. Therefore, this is a very rapid and reproducible assay.

Discussion

In many malignancies, as in esophagus cancer, TNM staging yields the best prognostic information. The absence of nodal involvement is associated with a more localized lesion suggesting that a cure may be obtained by surgical resection alone. Nodal metastases however, are indicators of tumor spread beyond the site of the primary tumor and, as such, necessitate systemic treatment. Although the role of chemotherapy in esophageal cancer remains controversial, some trials have shown trends indicating the benefit of pre-operative chemotherapy. One advantage of this approach is that more patients are able to complete the chemotherapy protocol, than would otherwise do so if they were to receive treatment following a very morbid surgical procedure. ongoing prospective, randomized clinical trials should resolve the utility of pre-operative chemotherapy in esophagus cancer patients in the near future. With the advent of minimally invasive surgical approaches to staging, there exists the potential to stage prior to resection and offer pre-operative chemotherapy when appropriate. Therefore, the accurate determination of nodal stage prior to attempted curative resection could become very important in the decision-making process for patients with esophageal cancer.

Currently, intra-operative nodal staging is performed by frozen sectioning and H&E staining. While this methodology has at least a 93% correlation with the gold standard of formalin fixed, H&E stained tissue examination, both methods suffer significant limitations. Specifically, 30–50% of histologically node negative esophagus cancer patients suffer disease recurrence despite potentially curative resection. This finding is most likely due to sampling error that is inherent in the conventional methodologies, as well as a lack of sensitivity for detecting micrometastases. Single tumor cells, or small foci of cells, are easily missed since only one or two 4 μM sections are studied and the vast majority of each node is left unexamined. Serial sectioning of lymph nodes can reduce the sampling error and thus minimize this limitation. For example, in studies on breast cancer, serial sectioning of lymph nodes, combined with immunohistochemistry, led to an upstaging in an additional 10–23% of nodes that were negative by routine histopathologic evaluation. This method is not routinely used however due to the significant time and labor involved in serial sectioning of numerous lymph nodes from each case.

In the last decade, many studies have used RT-PCR to detect tumor related mRNAs in lymph nodes in attempts to improve the sensitivity of micrometastasis detection. Studies on several cancer types have reported that RT-PCR is a reasonable prognostic indicator, but despite this, RT-PCR has not made its way into clinical practice. The main reasons for this are poor specificity (40–60%), false positive results in control nodes from patients without cancer and the lack of standardized assays for multi-center trials. In other work, it has been shown that a quantitative approach to RT-PCR (QRT-PCR) can overcome false positives due to background or ectopic gene expression, and can increase the specificity for predicting disease recurrence Godfrey TE, Raja S, Finkelstein SD, Kelly LA, Gooding W, Luketich JD. Quantitative RT-PCR Predicts Disease Recurrence in lymph Node-Negative Esophagus Cancer Patients. Proceedings from the 2001 *Annual Meeting of the American Association of Cancer Researchers* 42. Mar. 1, 2001. Due to the techniques used in that study, however, the RNA isolation and RT-PCR assay requires 4–6 hours to complete. As a result, that method can only be utilized post-operatively. Intraoperative QRT-PCR can be a reality only if it is performed rapidly enough to yield a result in a time frame comparable to intra-operative frozen section analysis (approximately 20–30 minutes). Along with rapid RNA isolation and reverse transcription protocols, this requires extremely fast PCR ramping times such as those attainable with the Roche Light Cycler® or the Cepheid Smart Cycler®. The Cepheid instrument was used herein due to the relative ease of use (no glass capillaries), independent control of each reaction site, availability of four color multiplexing and the potential for automated sample preparation and QRT-PCR. With this instrument it has been shown that a QRT-PCR assay can be performed on OCT embedded tissue sections within 30 minutes from RNA extraction to result. With modifications to the protocol reported here, QRT-PCR can be carried out in 18.5 minutes (data not shown). Using our rapid assay, a retrospective analysis of RNA from archival tissues with a median patient follow-up of 36 months was performed. Data showed that the rapid assay predicted disease recurrence with a sensitivity and specificity of 90% and 80% respectively. This data was comparable with the slower, and more traditional, TaqMan based analysis (90% and 90%). In the fresh tissue analysis, it was possible to distinguish all the histologically positive nodes from the benign control nodes in under 30 minutes. Using the expression level of CEA, it was also possible to characterize pathologically negative nodes as having an expression pattern that resembled either benign or pathologically positive nodes.

From this data, it appears that rapid QRT-PCR is at least as sensitive as fixed tissue examination and is more sensitive than intraoperative frozen section examination. This is demonstrated by the 2 positive nodes that were deferred or misdiagnosed during the intraoperative examination. To confirm this data, study of a much larger number of fresh lymph nodes is planned with the object to correlate the results with pathologic staging. As the data set matures, QRT-PCR will be correlated with with recurrence. This will permit determination of an optimal CEA expression cut-off value in the fresh tissue data set since this may be different from the cut-off for archived tissues. Due to the preliminary fresh tissue data, and problems inherent in analysis of archived tissues, it is possible that specificity and positive predictive values will improve with analysis of fresh tissues.

Further development of this technology will be necessary to bring intraoperative QRT-PCR from bench to bedside. In a clinical setting, the QRT-PCR assay has to be a simple and automated process with minimal handling. Towards this end, the goal is to develop a cartridge based processor for automated analysis. It is envisioned that the end product will be a single-use, disposable cartridge capable of both RNA isolation and quantitative RT-PCR set up. When integrated with a rapid cycling, real-time quantitative thermal cycler, this system will provide a QRT-PCR result from frozen sections in less than 25 minutes. Upon its development, and the identification of new and accurate markers, this technology could also be used for molecular analysis of surgical margins as well as an adjunct to fine needle aspirate cytology. Thus, molecular information regarding micrometastases and completeness of resection could, for the first time, be made available intraoperatively to the surgeon. Furthermore, the availability of an automated and reproducible QRT-PCR format will allow the true molecular diagnostic value of QRT-PCR to be evaluated in standardized multi-center trials.

Example 6

Description of a Novel Method for Multiplexing Polymerase Chain Reaction

Introduction

Despite the enormous power and flexibility of the Polymerase Chain Reaction (PCR), this technology has been slow to find its way into clinical diagnostic laboratories. In large part, this is due to the fact that the PCR process (from sample processing to reaction set-up and data analysis) is labor intensive, prone to contamination and technically quite demanding. As a result, false positive and false negative results are frequent and constitute a major concern in the clinical setting. Even so, most major clinical diagnostic laboratories are still running a handful of internally validated, PCR-based assays for a variety of applications such as viral detection and minimal residual disease detection in leukemia patients. Technological advances that simplify and, if possible, automate PCR procedures would greatly enhance the reproducibility and reliability of these assays.

One such technological advance, the introduction of rapid cycling, quantitative PCR instruments, is opening up new potential uses for molecular testing. The ability to complete PCR assays in less than 30 minutes now makes it possible to carry out time dependent, point of care molecular diagnostics such as testing for group B streptococcus in pregnant women and nosocomial agents in immunocompromised patients. In cancer diagnostics, such rapid tests bring the possibility of primary cancer diagnosis on core biopsies or fine needle aspirates (FNA) while the patient is still in the clinic, tumor profiling at the time of surgery to determine response to chemotherapy and intraoperative testing of lymph nodes and surgical margins to determine extent of disease and treatment options. For example, Reverse Transcription-PCR (RT-PCR) has been shown in many studies to improve the sensitivity of cancer cell detection in lymph nodes of cancer patients otherwise staged as node negative. These patients are at higher risk for disease recurrence and may benefit from more aggressive therapy. In the case of lung cancer for example, patients with mediastinal lymph node involvement may benefit from neoadjuvant chemotherapy but lymph node status needs to be determined prior to major surgical intervention. This can be achieved through minimally invasive surgery or even ultrasound guided FNA. Accurate intraoperative lymph node diagnosis would allow negative patients to undergo complete tumor resection while surgery would be halted in node positive patients to allow administration of chemotherapy. A similar scenario exists in patients with breast cancer or melanoma. In both diseases, sentinel lymph node positivity results in a complete lymph node dissection.

Since current intraoperative lymph node analysis methods are not very sensitive (~70% in breast cancer(Weiser MR, Montgomery LL, Susnik B, Tan LK, Borgen PI, Cody HS. Is routine intraoperative frozen-section examination of sentinel lymph nodes in breast cancer worthwhile? *Ann Surg*

Oncol. 2000;7:651–5)and 47% in melanoma(Fitzgerald RC, Triadafilopoulos G. Recent developments in the molecular characterization of Barrett's esophagus. Dig. Dis. 1998;16: 63–80.)) many patients are not diagnosed as lymph node positive until after completion of the surgery. These patients then have to undergo a second surgical procedure to complete the lymph node dissection. A more sensitive, intraoperative lymph node assessment would clearly benefit these patients. This example illustrates just one potential use of rapid PCR-based assays but many more are likely to be forthcoming in the near future. Once again however, advances are needed in PCR technology to make these exciting possibilities practical in the clinical diagnostic laboratory.

The recent introduction of fluorescence-based PCR, and RT-PCR, has greatly simplified data analysis steps by eliminating the need for post-PCR processing and gel electrophoresis. Added benefits of this technology include reduced assay contamination (since PCR tubes are never opened) and, of course, the ability to obtain highly accurate and reproducible quantitative results. Quantitation not only enhances the clinical utility of many potential diagnostic tests but also provides the ability to verify assay sensitivity and reproducibility from test to test with the use of external quality control standards. Internal quality controls are also required, including amplification of endogenous control sequences to check for quality and quantity of the template DNA or RNA, and internal positive controls to verify that the assay worked in the case of a negative result. While these 'internal' controls can actually be set up in separate tubes, it would be advantageous if all assays could be run (multiplexed) in the same PCR tube, taking advantage of different colored fluorogenic probes to distinguish the PCR products. Unfortunately, standard multiplex PCR does not work well when the amplification targets are not present in similar abundance at the beginning of the reaction and it is especially difficult to maintain accurate quantitation over a wide range of target concentrations. The dynamic range of a quantitative multiplex can be improved to some degree by severely limiting the PCR primer concentration for the more abundant gene in the PCR reaction. While this approach works reasonably well for standard RTPCR assays, the concept of primer limiting goes against the requirements of a rapid PCR assay, where higher primer concentrations are necessary to maintain amplification. Here, a method is described for multiplex PCR that has the same sensitivity and quantitative dynamic range as a singleplex PCR, and that can also be performed in a rapid RT-PCR reaction. It is demonstrated herein that this methodology is applicable to multiple different amplification targets and that, with the addition of a synthetic oligonucleotide mimic, it provides for an internally controlled, rapid, multiplex QRT-PCR. The value of this method in cancer diagnostics is demonstrated here by the detection of tumor cells in lymph nodes of esophageal cancer and melanoma patients. This rapid, intraoperative, QRT-PCR may eventually be used for more accurate intraoperative cancer staging and will therefore result in more appropriate and timely treatment of cancer patients.

Materials and Methods

Tissues and RNA isolation: All patient tissue samples were obtained through University of Pittsburgh IRB approved protocols. The lymph nodes from patients with esophagus cancer, and the benign nodes (obtained incidentally from patients undergoing anti-reflux procedures) were snap frozen in liquid nitrogen and RNA was extracted using the RNeasy Mini kit (Qiagen, Valencia Calif.) following the manufacturer's protocol. The histologically positive and negative lymph nodes from melanoma patients were obtained as formalin-fixed and paraffin embedded archived samples and RNA was extracted using previously described protocols (Godfrey T E, Kim S H, Chavira M, Ruff D W, Warren R S, Gray J W, Jensen R H. Quantitative mRNA expression analysis from formalin-fixed, paraffin-embedded tissues using 5' nuclease quantitative reverse transcription-polymerase chain reaction. *J Mol Diagn.* 2000;2:84–91.).

Development of the Rapid PCR Assay: Rapid PCR was initially tested using cDNA synthesized from human colon total RNA (Ambion, Austin Tex.) as template. PCR primers and probes for β-glucuronidase (β-gus) and carcinoembryonic antigen (CEA) were designed to be cDNA specific with amplicon sizes of 81 and 77 base pairs, respectively. Known pseudogenes for CEA were avoided and control PCR on 200 ng of genomic DNA was negative. PCR was performed in 25 µL reactions containing 800 nmol/L of each primer, 200 nmol/L of each probe (primer and probe sequences are shown in Table 9) and the PCR master mix [1× Platinum Taq reaction buffer, 4.5 mmol/L MgCl2, 300 µmol/L of each dNTP and 0.09 U/µL Platinum Taq DNA polymerase (Invitrogen, Carlsbad Calif.)]. Assays were performed on the Cepheid Smartcycler™ (Cepheid, Sunnyvale, Calif.) and analyzed with Smartcycler software v1.2b. PCR denaturation (95° C.) times of 10, 7, 5, 2 and 1 second, and annealing/extension (64° C.) times of 30,15,10,7,5 and 3 seconds were initially tested on a single cDNA input. The optimal rapid PCR cycling conditions (1 sec denaturation followed by a 6 sec annealing/extension) were then used to compare the rapid PCR protocol with more conventional cycling times of 10 sec denaturation and 30 sec annealing/extension. This was carried out on a serially diluted CEA standard curve to determine any effect of the rapid PCR protocol over a wide range of CEA inputs. The CEA cDNA was serially diluted (8×) in a constant background of β-gus template (purified β-gus PCR product) in amounts that were empirically determined to give constant β-gus cycle threshold (Ct) values between 19 and 20 cycles. Similar experiments were carried out to optimize and validate the tyrosinase assay.

TABLE 9

Primer and probe sequences

| Name | Sequence (5'→3') |
|---|---|
| CEA-F | AGACAATCACAGTCTCTGCGGA (SEQ ID NO: 6) |
| CEA-R | ATCCTTGTCCTCCACGGGTT (SEQ ID NO: 7) |
| CEA probe-FAM | FAM - AGCUGCCCAAGCCCU-BHQ1* (SEQ ID NO: 18) |
| CEA RT | GTGAAGGCCACAGCAT (SEQ ID NO: 9) |
| Gus 81F | CTCATTTGGAATTTTGCCGATT (SEQ ID NO: 3) |
| Gus 81R | CCGAGTGAAGATCCCCTTTTTA (SEQ ID NO: 4) |
| Gus 80F | CTCATTTGGAATTTTGCC (SEQ ID NO: 16) |
| Gus 80R | CGAGTGAAGATCCGCTT (SEQ ID NO: 17) |
| Gus probe | Texas Red - TGAACAGTCACCGACGAGAGTGCTGG-BHQ2 (SEQ ID NO: 5) |
| Gus RT | TTTGGTTGTCTCTGCCGAGT (SEQ ID NO: 2) |
| Tyrosinase-F | ACTTACTCAGCCCAGCATCATTC (SEQ ID NO: 19) |
| Tyrosinase-R | ACTGATGGCTGTTGTACTCCTCG (SEQ ID NO: 20) |
| Tyrosinase probe | FAM-TCTCCTCTTGGCAGATTGTCTGTAGCCGA-BHQ1 (SEQ ID NO: 21) |
| Tyrosinase RT | CGTTCCATTGCATAAAG (SEQ ID NO: 22) |
| Internal control probe | Alexa 546 - AGCATCATCCTCTGCATGGTCAGGTCAT-BHQ1 (SEQ ID NO: 23) |

*C and U were changed to their propyne pyrimidine counterparts

Development of the rapid reverse transcription assay. The RNA input for the RT-PCR was a mixture of 400 ng obtained from the A549 lung adenocarcinoma cell line and 25ng from a lymph node with metastatic esophageal adenocarcinoma.

RT-PCR reactions were performed for β-gus and CEA mRNA in 25μL containing the PCR master mix described above plus 60 nmol/L β-gus and CEA RT primers, 1 μL SensiScript reverse transcriptase (Qiagen) and 0.8U/μL RNase inhibitor. RT reaction was carried out at 48° C. in a 20.5 μL volume and the PCR primers and probes were added to the reaction mixture in a 4.5 μL volume during a 70° C. hold following the RT. This was done in order to maintain PCR specificity and sensitivity. RT was tested using 30, 10, 7, 5, 3 and 2 minutes to determine the fastest RT possible without loss of sensitivity.

Multiplex PCR Assays: In the temperature-controlled multiplex, both primer and probe sets for CEA and β-gus were added to the reaction mixture. In this case however, the β-gus primers (β-gus-80, 400 nmol/L) were redesigned to have a $T_m$ of 50° C. compared to the CEA primers which have a $T_m$ of 60° C. PCR was performed with a one second denaturation, a four second hold at 53° C. for annealing and a six second hold at 64° C. for extension and optical read (total anneal/extend time of ten seconds). The 53° C. anneal step was eliminated one cycle after the β-gus amplification plot reached threshold (determined beforehand in a separate singleplex reaction) and subsequent cycles were carried out with only the 64° C. anneal/extend as in the optimal, rapid PCR singleplex assay. Simple multiplexing was performed using 800 nM primers for both genes and utilized our standard β-gus-81 ($T_m$60° C.) primer set. The conventional primer-limited multiplex was carried out using 300 nmol/L β-gus-81 primers since this was determined to be the lowest concentration that did not result in a significant increase (>1 cycle) in the β-gus Ct values in a rapid PCR. The first 20 PCR cycles using the conventional methodologies were performed with an anneal/extend time of 10 seconds at 64° C. followed by a change to 6 seconds for the remaining cycles. This was done in order to better simulate the conditions used in the temperature-controlled multiplex and allow direct comparison of the methods. All three multiplex methods were tested on serial dilutions of CEA cDNA (as described above) in order to determine the accuracy and dynamic range compared with singleplex reactions.

Internal positive controls. The internal positive controls (IPC) are DNA oligonucleotides that have the same primer sequences as the target gene (CEA or tyrosinase) but have a different internal probe sequence (Table 10). Selected sites in the IPC's were synthesized with uracil instead of thymine so that contamination with the highly concentrated mimic could be controlled using uracil DNA glycosylase if required. The IPCs were added to the reaction mastermix in amounts that were determined empirically to give Ct values of 36–37 cycles. The rapid triplex assays were then performed as described for the primer-limited multiplex (duplex) above with the addition of the internal control (IC) probe at a concentration of 200 nmol/L.

were tested using rapid, multiplexed QRT-PCR in order to demonstrate the utility of this technique. Lymph node RNA was analyzed using a triplex QRT-PCR (β-gus, CEA or Tyrosinase and appropriate mimic), with the temperature controlled primer limiting technique. Reverse transcription was carried out as described above with a 5 minute RT followed by a 30 second hold at 70° C. for addition of PCR primers. Cycle threshold values for β-gus were determined in a prior, singleplex run so that the temperature change could be initiated at the appropriate cycle in the multiplex reaction.

Results

Figure 13:
FIG. 13 shows Ct values for β-gus and CEA in a 8-fold serial dilution of CEA in a constant background of β-gus. This figure compares the slow conventional PCR (10 sec denaturation followed by a 30 sec annealing/extension step) with rapid PCR (1 sec denaturation followed by a 6 second annealing/extension step). ♦=10, 30 GUS; □=1, 6 GUS; ∆=10,30 CEA; and ●=1,6 CEA.

Rapid PCR development: Rapid PCR assays were developed separately for all genes in singleplex assays prior to using them in a multiplex reaction. For development of the rapid PCR assays, the effect of reducing both the denaturation time (10, 7, 5, 2, 1 seconds at 95° C.) and the anneal/extend time (30,15,13,10,7,6,3 seconds at 64° C.) was evaluated to determine any observed changes in Ct values. For the denaturation time test the anneal/extend time was kept constant at 30 seconds and for the anneal/extension time test the denaturation time was kept constant at 10 seconds. It was found that reducing the denaturation time to 1 second had no effect on the Ct values for either CEA or β-gus genes (FIG. 12, panel A). Similarly, reducing the annealing/extension time had minimal effect (~0.5 cycles) on the Ct values for both genes down to 5 seconds while a 3 second anneal/extend resulted in a Ct increase of 1.1 cycles for CEA and 1.8 cycles for β-gus when compared with the 30 second anneal/extend control (FIG. 12, panel B). Thus, for further testing a 1 second denaturation and a 6 second anneal extend were chosen. To evaluate the effect of the rapid PCR assay on sensitivity and quantitation over a wide range of CEA input amounts a serially diluted standard curve of CEA cDNA in a constant background of β-gus PCR target was generated. Using this standard curve, the rapid assay was compared with a more conventional PCR with 10 second denaturation and 30 second anneal/extension (FIG. 13). The rapid assay resulted in an average increase in Ct value of 1.6 cycles for CEA and 0.2 cycles for β-gus. These increases appear to be consistent from point to point, and as a result, the quantitative ability of the rapid assay is equal to that of the slower PCR. The total PCR time to run 40 cycles using the rapid assay was 15 minutes versus 48 minutes for the slower PCR protocol.

Rapid reverse transcription: Rapid analysis of gene expression by RT-PCR requires that both the reverse transcription and PCR components of the assay are rapid. For this reason the effect of reducing the reverse transcription time from 30 minutes down to 10,7,5,3 and 2 minutes (FIG. 12, panel C) was evaluated. In this assay, the PCR times

TABLE 10

CEA and Tyrosinase internal positive control mimics.

CEA mimic: (SEQ ID NO: 24)
*AGACAATCACAGTCTCTGCGGA*AGCATCATCCTCTGCATGGTCAGGTCAT*AACTCCAAACCCGTGGAGGACAAGGAT*
Tyrosinase mimic: (SEQ ID NO: 25)
*ACTTACUCAGCCCAGCAUCAUUCT*AGCATCATCCTCTGCATGGTCAGGTCAT*TTGGAGGAGUACAACAGCCAUCAGT*

Italic = gene specific primer sites, Bold = probe sequence from bacterial β-galactosidase gene.

Figure 14:
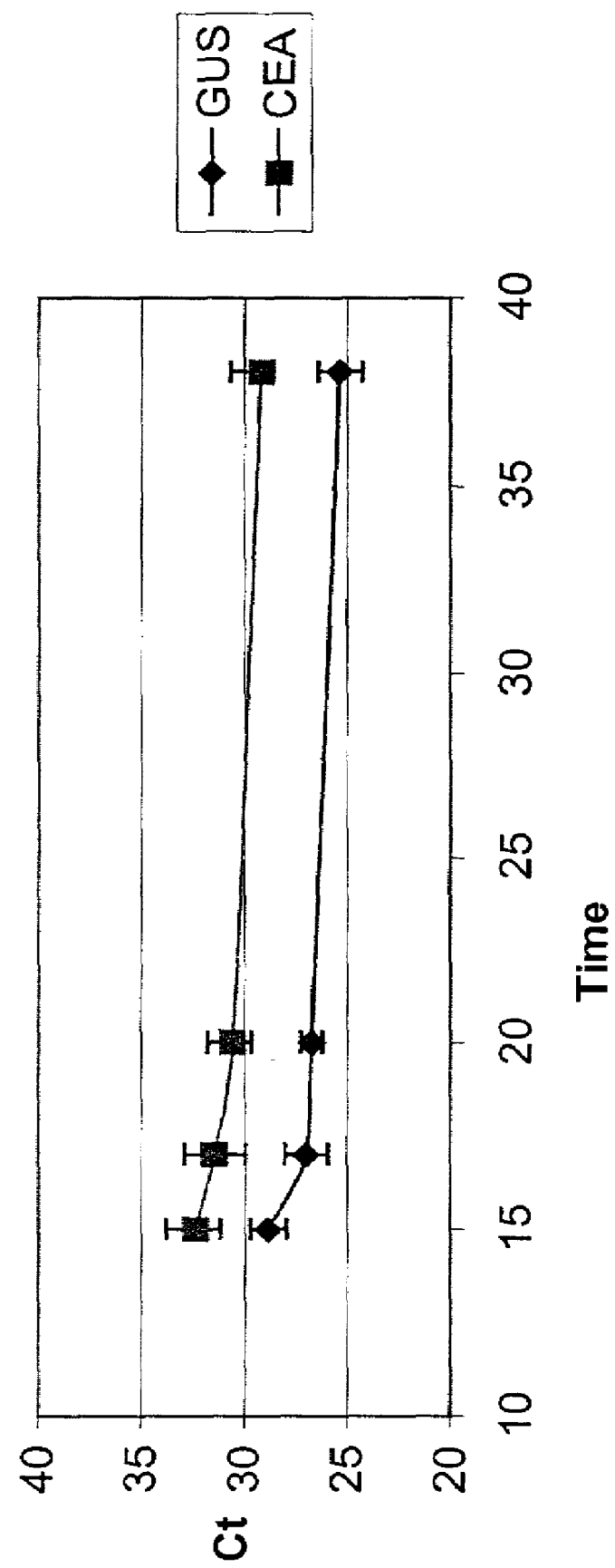
FIG. 14 is a RT-PCR run time comparison between a 15 min (2 min RT and ⅓ PCR), 17 min (2 min RT and ⅙ PCR), 20 min (5 min RT, ⅙ PCR) and a 38 min (10 min RT and ⁵⁄₁₅ PCR) assays.

Lymph node assays. Histologically positive and negative lymph nodes from esophageal cancer and melanoma patients were held constant at 2 second denaturation and 15 second anneal/extension. The results showed an increase in Ct value of only 1.1 and 0.6 cycles for β-gus and CEA respectively with a 5 minute reverse transcription and 1.1 and 1.8 cycles with a 2 minute reverse transcription when compared with 30 minutes. While none of these differences were significant for individual time point comparisons, there does appear to be a clear trend towards increased Ct with reduced time as would be expected. The combined effect of decreasing both the RT and PCR times on the sensitivity of the assay was evaluated using 4 different RT and PCR parameter combinations (FIG. 14). Once again a trend was observed towards higher Ct's with shorter RT-PCR protocols but with a 20 minute total RT-PCR time (5 minute RT with a ⅙ PCR) the Ct difference was only 1.4 cycles for both genes when compared with a 38 minute total RT-PCR (10 minute RT, ¹⁰⁄₁₅ PCR).

Figure 15:
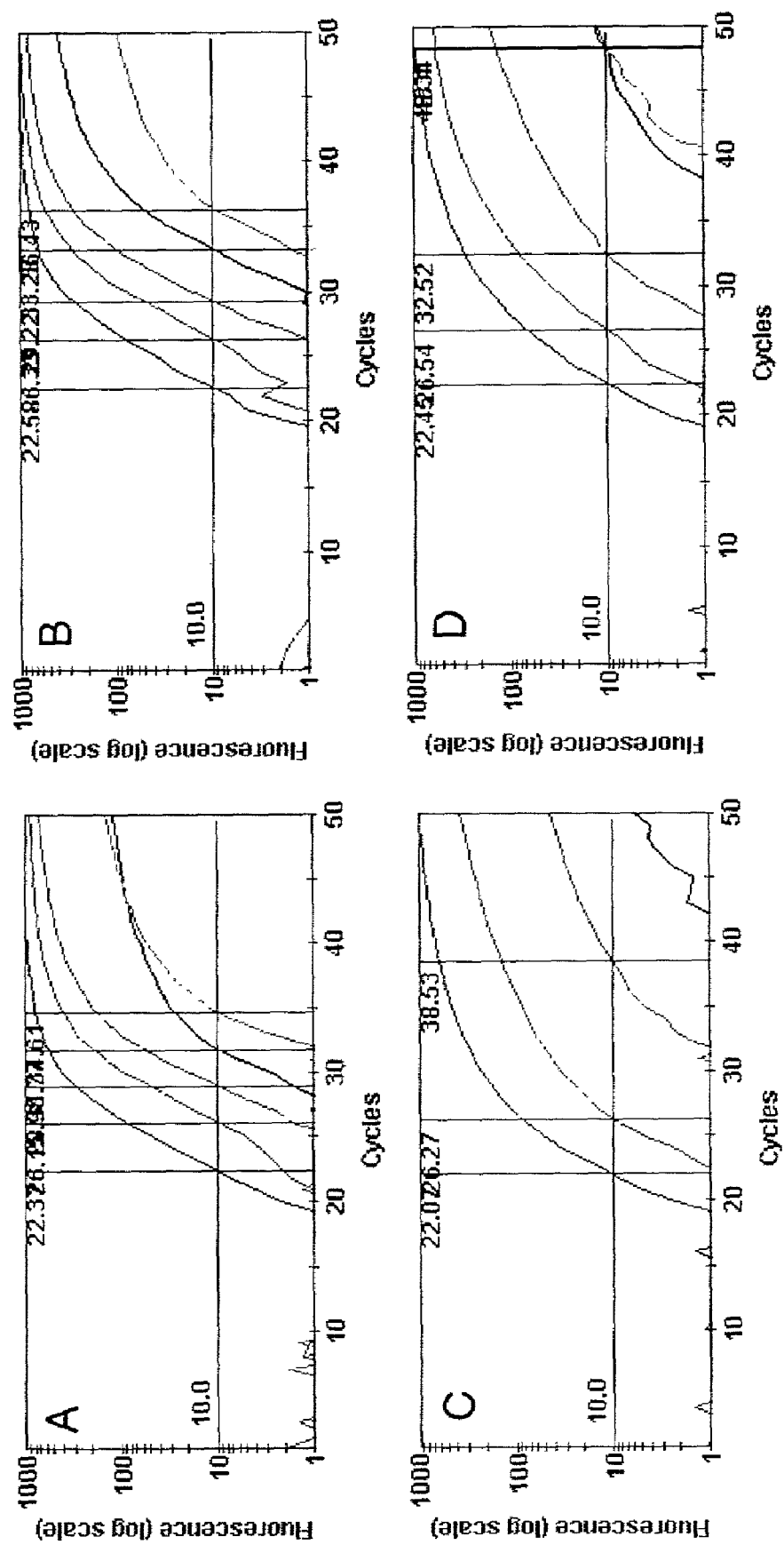
FIG. 15 shows four amplification plots for CEA singleplex (panel A), CEA in the temperature-controlled multiplex (panel B), CEA in the ordinary multiplex (panel C) and CEA in the conventional primer limiting multiplex (panel D)

Multiplex PCR assay: Testing of different multiplexing methods was carried out on the same dilution series of CEA in constant background of β-gus that was used for the rapid PCR development. This dilution series spanned approximately 12 cycles, corresponding to a 4,096 fold difference in the starting CEA abundance between the first and the last points on the curve (FIG. 15, panel A ). The dilution series was used to compare singleplex reactions for each gene with a simple multiplex PCR (FIG. 15, panel C), a conventional primer limited multiplex PCR (FIG. 15, panel D) and our temperature controlled, primer limited multiplex PCR (FIG. 15, panel B). When a simple multiplex reaction was carried out for both CEA and β-gus only the first three of five points from the series reached threshold for CEA while the reaction for the more abundant β-gus amplified consistently (not shown). Similar results were observed for the conventional primer limited reaction while the temperature controlled primer limiting produced results almost identical to the singleplex reactions.

Figure 16:
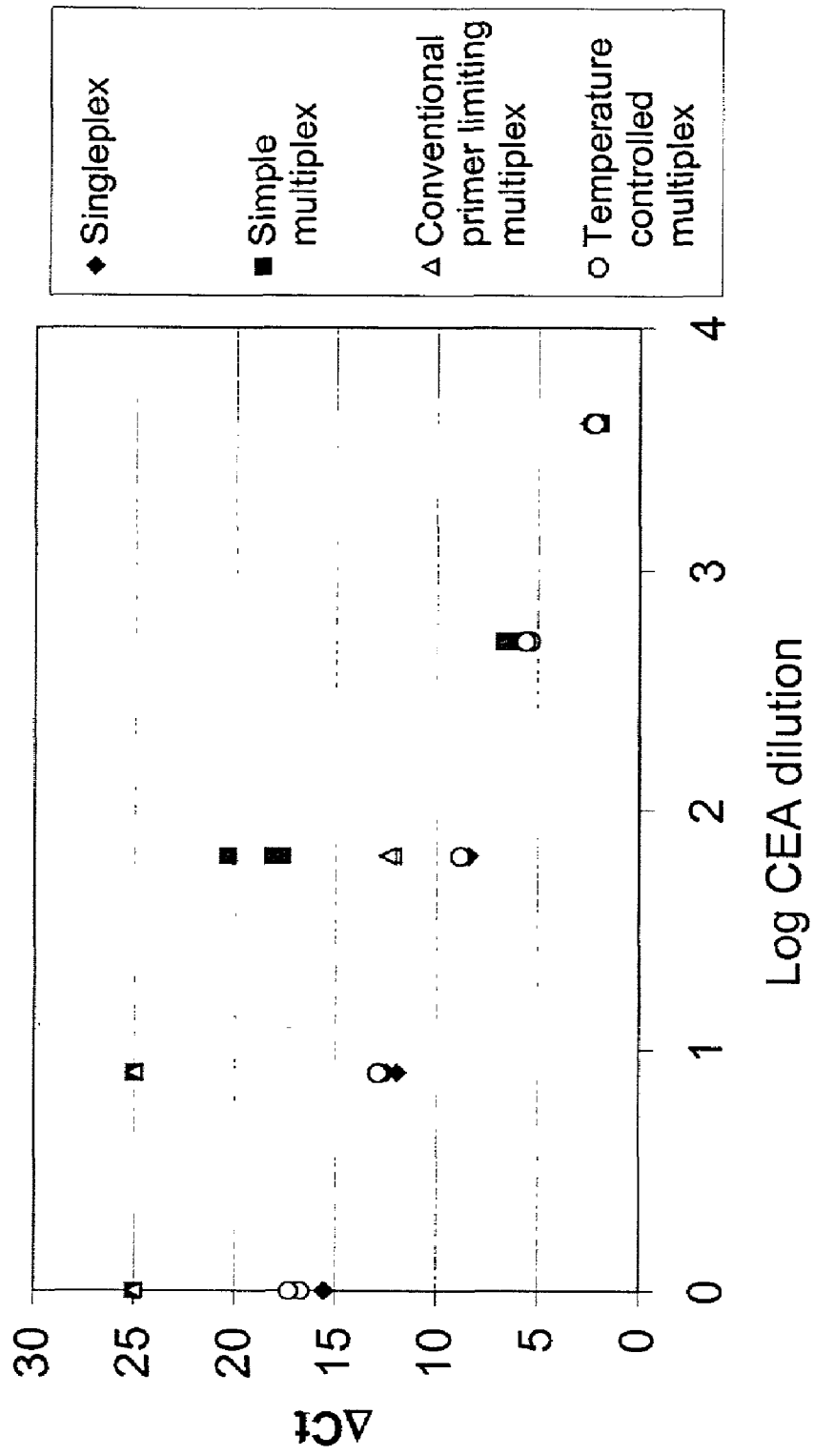
FIG. 16 shows a comparison of the singleplex PCR for CEA with the temperature-controlled multiplex, ordinary multiplex and the conventional primer limiting multiplex. The delta Ct values for a serial dilution of CEA in constant background of β-gus are compared. Delta Ct of 25 is used to denote a dilution point that failed to amplify.

Perhaps, more relevant than the range of CEA concentrations is the range of delta Ct (difference in Ct value between the more abundant β-gus gene and the CEA target gene) that can be achieved with the different techniques. In these experiments the β-gus Ct was constant for all assays between 19 and 20 cycles and thus the largest delta Ct in this dilution series with a singleplex assay was almost 15 cycles (~32,000 fold difference in abundance). FIG. 16 shows the delta Ct's plotted for each of the three multiplexing methods as well as the singleplex data. In the simple multiplex the third point in the series had a Ct value of 38.5 cycles compared with 29.0 for the same point in the singleplex reaction, while subsequent points failed to amplify at all. Thus the simple multiplex demonstrates a lack of quantitation with a true delta Ct of ~8 cycles, as well as a very limited dynamic range. The conventional primer limited multiplex worked a little better (delta Ct for the third dilution point was 4.0 cycles higher than the singleplex) but once again, dilution points four and five failed to amplify. Thus it seems that despite its feasibility in standard PCR reactions, conventional primer limiting is not amenable to rapid assays where increased primer concentrations are required. In comparison, the temperature controlled multiplex amplified all points on the dilution series and no difference was observed in the delta Ct until the last point. These results clearly demonstrate that the temperature controlled primer limit was comparable to singleplex reactions in the rapid QPCR assay while all other multiplexing approaches remained inadequate. Furthermore, this technique has been utilized on other targets, such as tyrosinase, and the method appears to be easily adaptable to new targets.

Figure 17:
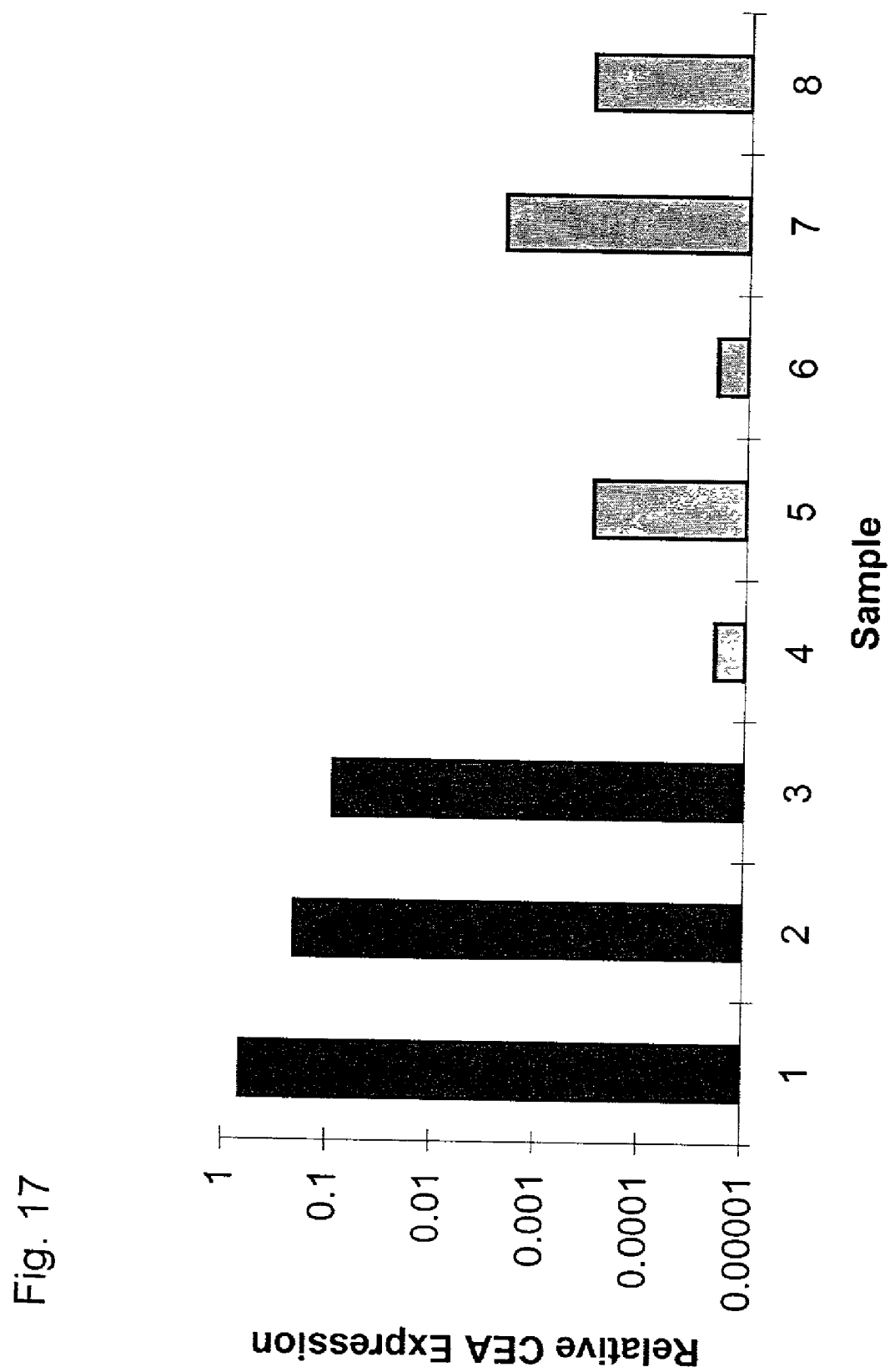
FIG. 17 is a histogram of CEA expression relative to β-gus in lymph nodes. Bars in Black (1–3) correspond to lymph nodes from patients with cancer with histological evidence of cancer. Bars in Gray (4–8) correspond to lymph nodes from patients without cancer. Samples 4 and 6 had no detectable CEA expression.
Figure 18:
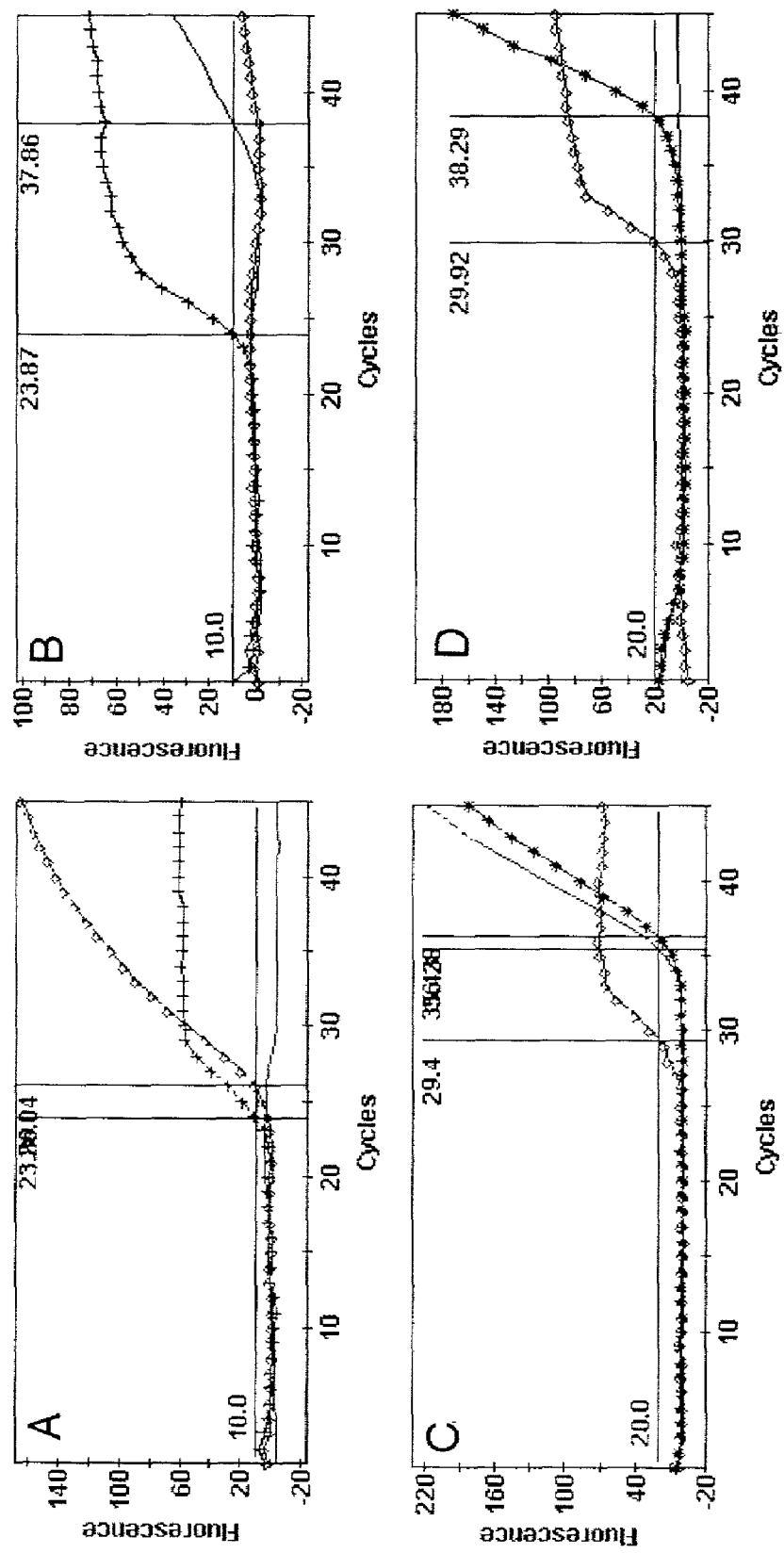
FIG. 18 shows four representative amplification plots for samples with the expression of CEA (A) and tyrosinase (C), and samples without the expression of CEA (B) and tyrosinase (D). In panels A and B, the fluorescence curves for β-gus (+),CEA (◊) and CEA IC (−) are shown. Similarly in panels C and D, the fluorescence curves for β-gus (◊), tyrosinase (−) and tyrosinase IC (*) are shown.

Lymph node analysis using rapid, multiplex RT-PCR: For lymph node analysis internal positive control mimics for CEA and tyrosinase were included in the multiplex reactions. This internally controlled, rapid RT-PCR multiplex was used to evaluate lymph nodes from patients with esophageal cancer and with melanoma as well as benign lymph nodes from patients without cancer. In three histologically positive esophageal cancer lymph nodes, high levels of CEA expression were detected. In lymph nodes from non-cancer patients, 2 of 5 nodes had no detectable levels of CEA expression and the remaining three had low levels of CEA expression (FIG. 17). Furthermore, in cases where CEA signal was detected, the internal positive control was not amplified (FIG. 18, panel A). However, in CEA-negative samples, there was amplification of the CEA internal positive control confirming that negative results were indeed due to the absence of CEA expression and not a failed CEA PCR (FIG. 18, panel B). Similar results were obtained for melanoma lymph nodes using tyrosinase mRNA as the cancer marker. Five lymph nodes that were histologically positive for melanoma and 5 lymph nodes without any evidence of cancer were tested. Tyrosinase was detected at high levels in the all histologically positive nodes and at very low levels in only one of the five negative nodes (data not shown). In the positive nodes, the expression of tyrosinase was higher than that of β-gus and as a result only the tyrosinase gene amplification was seen. In all the five negative nodes the amplification of β-gus and the IPC was seen (FIG. 18, panels C and D).

Discussion

The introduction of rapid cycling PCR instruments capable of real time fluorescence-based quantitation has opened the door for application of molecular diagnostic assays in clinical situations where time is limited or where a rapid result would be of psychological or physical benefit to the patient. One case where rapid molecular assays may be advantageous is in intra-operative lymph node staging of malignancies such as melanoma, breast and lung cancer. Conventional analysis of frozen tissue sections is very quick (approximately 20 minutes in most institutions) but the sensitivity of this technique for detecting small foci of tumor is relatively low. Furthermore, many patients who are staged as lymph node negative by histologic examination suffer recurrence of their disease, probably as a result of occult disseminated tumor cells that were missed by routine examination. There is much evidence that RT-PCR, and particularly quantitative RT-PCR, can detect these occult cells and identify patients at high risk for recurrence. If this information can be obtained intraoperatively, surgeons will be able to make more informed treatment decisions regarding the need for adjuvant therapy and extent of resection.

It has been shown that it is feasible to carry out QRT-PCR in an intraoperative time frame and that this technique can be superior to frozen sectioning and, at least, comparable to formalin fixed histology. In the present Example, these rapid QRT-PCR protocols are tested and it is shown that this complete assay can be carried out in under 20 minutes. While this time frame is adequate for intra-operative testing there are still several practical and technical hurdles that need to be addressed before rapid QRT-PCR can be considered feasible in the clinical diagnostic setting. It is believed that the assays must be standardized to allow data comparison between sites in multi-center trials, automated (including RNA isolation) to eliminate operator dependent variability and contamination and controlled for all aspects of the assay including internal endogenous and exogenous positive controls.

The latter of these requirements, quality controls, necessitates the incorporation of multiplexing into the rapid QRT-PCR. At least two control reactions are required, an endogenous control gene to verify presence and adequate quantity and quality of RNA and an exogenous positive control to verify that the target gene QRT-PCR functioned with adequate sensitivity in samples that are negative for target gene expression. Together these two controls ensure that a negative result is truly negative and not a result of failed RT-PCR. Thus, at least a triplex PCR reaction is needed. Unfortunately, maintaining quantitation in a multiplex PCR has not been easy even in a standard, slow PCR assay. This is because accumulation of one PCR product (from the most abundant target gene) inhibits amplification of other targets.

Initially this inhibition is seen as a shift of the cycle threshold value to a higher cycle number, and a drop in the total fluorescence, when compared with a singleplex reaction (FIG. 15 panels A, C and D). If the difference in abundance of the two genes is too great however, the less abundant gene will fail to amplify completely. Thus the typical multiplex reaction lacks quantitation and suffers from a poor dynamic range. Inhibition of the less abundant target sequence is probably a consequence of several factors including the accumulation of pyrophosphate released from the addition of nucleotides during DNA synthesis and inhibition/sequestration of the Taq enzyme by accumulating PCR product. One way to overcome this inhibition is to somehow stop amplification of the more abundant gene soon after signal has been detected and before pyrophosphate and PCR product have accumulated enough to cause inhibition. Conventional methods for this rely on limiting the primer concentration for the more abundant target gene such that the primers are used up, and PCR of that specific target stops, before inhibition can occur. While this method works reasonably well in a slow PCR assay, reducing primer concentration in a rapid assay results in a lower PCR efficiency, and eventually, complete PCR failure. In our studies the lowest primer concentration that did not change the cycle threshold value for β-gus was determined and tested in a conventional primer limited assay using our rapid PCR protocol. While this proved slightly better than multiplexing without a primer limit, quantitation and dynamic range were still poor compared with singleplex reactions. In the method described herein, the melting temperature (Tm) of the primers for the more abundant species (β-gus) are designed to function at a lower temperature than those for the target gene (CEA or Tyrosinase). The PCR itself is carried out in two stages. The annealing step for the first stage of the PCR is performed at a relatively low annealing temperature (53° C. in this example) until the amplification curve of the more abundant species reaches detection threshold. Following this, the second stage of the PCR is carried out with an annealing temperature that is at least 10° C. higher than the Tm of the low temperature primers (64° C. for this example). The higher temperature of the second stage shifts the binding state of the low temperature β-gus PCR primers to favor the single stranded state, effectively terminating amplification of β-gus while amplification of the CEA target continues uninhibited. Thus, it is possible to maintain the high primer concentration needed for rapid PCR of the more abundant control gene and still maintain quantitation over a large dynamic range of the target gene.

In addition to developing the rapid multiplexing technology, an internal positive control mimic is incorporated that can be used to prove that adequate RT-PCR sensitivity was achieved in samples that are negative for target gene expression. This mimic utilizes the same primers as the target gene and therefore controls for the function of these oligonucleotides. The DNA mimic might be replaced with an RNA mimic that also includes the reverse transcription primer site. This will then control for both the RT and PCR steps of target gene amplification. By adding this mimic to samples at concentrations that are low enough to produce Ct values greater than 35 cycles, one can be sure that the RNA isolation and RT-PCR reaction not only worked but that it worked well enough to detect a very low abundance of target gene if it were present. In cases where the target gene is highly expressed, the internal mimic may fail to amplify. This is acceptable because the mimic is only intended as a control for negative reactions.

Therefore, the potential use of rapid QRT-PCR for detection of metastatic tumor cells in lymph nodes of cancer patients has been shown. While this is a particularly exciting use of rapid molecular diagnostics it is only one potential application. As new cancer markers are developed it is possible that rapid QRT-PCR could also be used intraoperatively for analysis of surgical margins, in the clinic for analysis of biopsies or fine needle aspirates or for analysis of primary tumors to predict response to chemotherapy or new biotherapies such as tyrosine kinase inhibitors. Although the dual temperature PCR cycling required for the temperature controlled multiplex adds approximately 2 minutes to the overall reaction time, a complete, multiplexed QRT-PCR assay can still be carried out in under 22 minutes. With the addition of external cooling to the SmartCycler™, or its future generations, it is believe that an extra 3–4 minutes can be saved. Also, in the current work, the cycle number at which the temperature change needed to be initiated was pre-determined. Ultimately, a minor modification in the instrument's software will automatically increase the PCR annealing temperature after the endogenous control gene fluorescence reaches threshold. Since all PCR sites are independently controlled, this will allow multiple reactions to be run at the same time with unknown amounts of starting RNA template. Finally, rapid QRT-PCR is now becoming feasible in a clinical setting. Using technology currently under development, RNA isolation can also be carried out very quickly in an automated process. To this end, certain fully integrated RNA isolation, reverse transcription and quantitative PCR instruments, such as Cepheid's GenXpert™, will automate, according to a series of programming steps, all of these processes and provide a QRT-PCR result in under 30 minutes. The combination of the rapid, internally controlled multiplex technology described herein with an automated sample processing platform will allow for accurate and yet expeditious measurements in a closed environment. The simplicity and sensitivity of this integrated system should enable many new applications of molecular assays in cancer diagnostics.

The use of numerical values in the various ranges specified in this application, unless expressly indicated otherwise, are stated as approximations as though the minimum and maximum values within the stated ranges were both preceded by the word "about". In this manner slight variations above and below the stated ranges can be used to achieve substantially the same results as values within the ranges. Also, the disclosure of these ranges is intended as a continuous range including every value between the minimum and maximum values.

We claim:

1. A one-tube RT-PCR method, comprising:
   (a) conducting a reverse transcription reaction for less than about 10 minutes on an RNA sample in a reaction mixture to produce a DNA sample;
   (b) adding a PCR reagent composition containing a PCR primer set and a thermostable DNA polymerase to the reaction mixture; and
   (c) conducting a PCR amplification on the reaction mixture.

2. The method of claim 1, wherein prior to the PCR amplification, the PCR reagent composition is separated from the reaction mixture in a reaction vessel by a physical barrier which is removed prior to or during the first cycle of the PCR reaction, thereby adding the PCR reagent composition to the reaction mixture.

3. The method of claim 1, wherein the reverse transcription reaction is conducted for about 2 minutes.

4. The method of claim 1, wherein the RT-PCR method is performed in an automated system and the reagents for the RT-PCR method are stored in a cartridge having a plurality of compartments in which the reagents are stored prior to use in the RT-PCR method, wherein the automated system adds the reagents to a reaction vessel from the cartridge according to a programmed sequence.

5. A multiplex, quantitative PCR method, comprising conducting a PCR amplification in a PCR reaction mixture on a DNA sample comprising a first nucleic acid species containing a first target amplification sequence and a second nucleic acid species different from the first nucleic acid species containing a second target amplification sequence, wherein the PCR amplification is conducted in a first amplification stage and a second amplification stage, each amplification stage comprising one or more PCR cycles and each PCR cycle comprises a denaturing step, an annealing step and an elongation step that may be conducted at the same temperature as the annealing step, wherein the PCR amplification of the second amplification stage is conducted under different reaction conditions than the PCR amplification of the first amplification stage to modulate the relative rate of production of a first amplicon corresponding to the first target amplification sequence by a first primer set and a second amplicon corresponding to the second target amplification sequence by a second primer set during the first and second amplification stages, thereby balancing the multiplex PCR amplification, wherein one of the first PCR primer set and the second PCR primer set produce one of a β-glucuronidase-specific amplicon, an 18S rRNA-specific amplicon, a carcinoembryonic antigen-specific amplicon and a tyrosinase-specific amplicon.

6. The method of claim 5, wherein one of the first PCR primer set and the second PCR primer set includes a primer comprising the sequence of one of SEQ ID NOS:3, 4, 6, 7, 11, 12, 13, 14, 16, 17, 19 and 20.

7. The method of claim 5, wherein the first primer set produces a β-glucuronidase-specific amplicon and the second primer set produces a carcinoembryonic antigen-specific amplicon, the Tm of the first primer set being about 1° C. lower than the Tm of the second primer set and the annealing temperature for the PCR amplification of the first amplification stage is about 1° C. lower than the annealing temperature for the PCR amplification of the second amplification stage.

8. The method of claim 5, wherein the first PCR primer set consists of SEQ ID NOS: 16 and 17, and the second PCR primer set consists of SEQ ID NOS: 6 and 7, the annealing temperature for the PCR amplification of the first amplification stage is the equivalent of about 53° C. and the annealing temperature for the PCR amplification of the second amplification stage is the equivalent of about 64° C., based on initial primer concentration of both PCR primer sets of 400 nM/L and an effective Tm for the first PCR primer set of about 50° C. and an effective Tm for the second PCR primer set of about 60° C.

9. A multiplex, quantitative PCR method, comprising conducting a PCR amplification in a PCR reaction mixture on a DNA sample comprising a first nucleic acid species containing a first target amplification sequence and a second nucleic acid species different from the first nucleic acid species containing a second target amplification sequence, wherein the PCR amplification is conducted in a first amplification stage and a second amplification stage, each amplification stage comprising one or more PCR cycles and each PCR cycle comprises a denaturing step, an annealing step and an elongation step that may be conducted at the same temperature as the annealing step, wherein the PCR amplification of the second amplification stage is conducted under different reaction conditions than the PCR amplification of the first amplification stage to modulate the relative rate of production of a first amplicon corresponding to the first target amplification seciuence by a first primer set and a second amplicon corresponding to the second target amplification sequence by a second primer set during the first and second amplification stages, thereby balancing the multiplex PCR amplification, wherein the amplification stages include one or more quantitative PCR reactions using a fluorescent reporter to indicate accumulation of a specific amplicon.

10. The method of claim 9, wherein the quantitative PCR reactions are fluorescent 5' nuclease assays.

11. The method of claim 9, wherein the fluorescent reporter is a molecular beacon.

12. A multiplex PCR method, comprising conducting a PCR amplification on a DNA sample in a PCR reaction mixture, wherein the PCR amplification is conducted in a first amplification stage and a second amplification stage, each amplification stage comprising one or more PCR cycles and each PCR cycle comprises a denaturing step, an annealing step and an elongation step that may be conducted at the same temperature as the annealing step, wherein the PCR amplification of the second amplification stage is conducted under different reaction conditions than the PCR amplification of the first amplification stage to modulate the relative rate of production of a first amplicon by a first primer set and a second amplicon by a second primer set during the first and second amplification stages, wherein the denaturation step for one or more cycles is about 1 second or less.

13. The method of claim 12, wherein the denaturation step for each cycle is about 1 second or less.

14. A multiplex, quantitative PCR method, comprising conducting a PCR amplification in a PCR reaction mixture on a DNA sample comprising a first nucleic acid species containing a first target amplification seciuence and a second nucleic acid species different from the first nucleic acid species containing a second target amplification sequence wherein the PCR amplification is conducted in a first amplification stage and a second amplification stage, each amplification stage comprising one or more PCR cycles and each PCR cycle comprises a denaturing step, an annealing step and an elongation step that is conducted at the same temperature as the annealing step, wherein the PCR amplification of the second amplification stage is conducted under different reaction conditions than the PCR amplification of the first amplification stage to modulate the relative rate of production of a first amplicon corresponding to the first target amplification sequence by a first primer set and a second amplicon corresponding to the second target amplification sequence by a second primer set during the first and second amplification stages, thereby balancing the multiplex PCR amplification.

15. A multiplex, quantitative PCR method, comprising conducting a PCR amplification on a PCR reaction mixture in a first stage and a second stage, the reaction mixture comprising a DNA sample comprising a first nucleic acid species containing a first target amplification sequence and a second nucleic acid species different from the first nucleic acid species containing a second target amplification sequence, a first primer set for amplification of the first target amplification sequence and having a first effective Tm and a second primer set for amplification of the second target amplification seciuence and having a second effective Tm different from the first effective Tm, each amplification stage comprising one or more PCR cycles, each PCR cycle comprising a denaturing step, an annealing step and an elongation step that may be conducted at the same temperature as the annealing step, wherein the annealing step of the first amplification stage is conducted at a greater temperature than the annealing step of the second amplification stage to modulate the relative rate of production of a first amplicon by the first primer set and a second amplicon by the second primer set during the first and second amplification stages, thereby balancing the multiplex PCR amplification.

16. An RT-PCR method comprising:
(a) conducting a reverse transcription reaction for less than about 10 minutes on an RNA sample in a reaction mixture; and
(b) conducting a POR reaction on the reaction mixture, wherein the reverse transcription reaction is conducted prior to the PCR reaction, and prior to the addition of one of POR primers and a thermostable DNA polymerase to the reaction mixture, to produce DNA in the DNA sample of the reaction mixture.

17. The method of claim 16, wherein the reverse transcription reaction is conducted for about 2 minutes.

18. A multiplex, quantitative PCR method, comprising conducting a PCR amplification in a PCR reaction mixture on a DNA sample comprising a first nucleic acid species containing a first target amplification sequence and a second nucleic acid species different from the first nucleic acid species containing a second target amplification sequence, wherein the PCR amplification is conducted in a first amplification stage and a second amplification stage, each amplification stage comprising one or more PCR cycles and each PCR cycle comprises a denaturing step, an annealing step and an elongation step that may be conducted at the same temperature as the annealing step, wherein the PCR amplification of the second amplification stage is conducted under different reaction conditions than the PCR amplification of the first amplification stage to modulate the relative rate of production of a first amplicon corresponding to the first target amplification sequence by a first primer set and a second amplicon corresponding to the second target amplification sequence by a second primer set during the first and second amplification stages, thereby balancing the multiplex PCR amplification.

19. The method of claim 18, wherein the second primer set is added to the reaction mixture at the beginning of the second amplification stage.

20. The method of claim 18, wherein one of the first PCR primer set and the second PCR primer set produce one of a β-glucuronidase-specific amplicon, an 18S rRNA-specific amplicon, a carcinoembryonic antigen-specific amplicon and a tyrosinase-specific amplicon.

21. The method of claim 20, wherein one of the first PCR primer set and the second PCR primer set includes a primer comprising the sequence of one of SEQ ID NOS: 3, 4, 6, 7, 11, 12, 13, 14, 16, 17, 19 and 20.

22. The method of claim 20, wherein one of the first PCR primer set and the second PCR primer set includes a primer consisting of one of SEQ ID NOS: 3, 4, 6, 7, 11, 12, 13, 14, 16, 17, 19 and 20.

23. The method of claim 18, wherein the reaction mixture comprises a DNA sample, the first primer set having a first effective Tm and the second primer set having a second effective Tm different from the first effective Tm, wherein the annealing step of the first amplification stage is conducted at a different temperature than the annealing step of the second amplification stage.

24. The method of claim 23, wherein the annealing step and the elongation step in a PCR cycle of at least one of the first amplification stage and the second amplification stage are conducted at the same temperature.

25. The method of claim 23, wherein the annealing step and the elongation step in a PCR cycle of at least one of the first amplification stage and the second amplification stage are conducted at different temperatures.

26. The method of claim 23, wherein the first primer set produces a β-glucuronidase-specific amplicon and the second primer set produces a carcinoembryonic antigen-specific amplicon, the Tm of the first primer set being about 1° C. lower than the Tm of the second primer set and the annealing temperature for the PCR amplification of the first amplification stage is about 1° C. lower than the annealing temperature for the PCR amplification of the second amplification stage.

27. The method of claim 25, wherein the first PCR primer set consists of SEQ ID NOS: 16 and 17, and the second PCR primer set consists of SEQ ID NOS: 6 and 7, the annealing temperature for the PCR amplification of the first amplification stage is the equivalent of about 53° C. and the annealing temperature for the PCR amplification of the second amplification stage is the equivalent of about 64° C., based on initial primer concentration of both PCR primer sets of 400 nM/L and an effective Tm for the first PCR primer set of about 50° C. and an effective Tm for the second PCR primer set of about 60° C.

28. The method of claim 18, wherein the denaturation step for each cycle is about 1 second.

29. The method of claim 18, wherein the denaturation step for each cycle is less than about 1 second.

30. The method of claim 18, further comprising conducting a reverse transcription reaction on an RNA sample prior to the first amplification stage, and prior to the addition of PCR primers to the reaction mixture, to produce the DNA of the DNA sample of the reaction mixture.

31. The method of claim 30, wherein the reverse transcription reaction is conducted for less than about 10 minutes.

32. The method of claim 30, wherein the reverse transcription reaction is conducted for about 2 minutes.

33. The method of claim 30, wherein one or both of an Internal Positive Control RNA and an Internal Positive Control DNA is added to the reverse transcription reaction.

34. The method of claim 18, wherein an Internal Positive Control DNA is added to the PCR reaction mixture.

35. The method of claim 34, wherein the Internal Positive Control DNA comprises the sequence of one of SEQ ID NOS 23–25.

36. The method of claim 34, wherein the Internal Positive Control DNA contains one or more uracil residues.

37. The method of claim 18, wherein the amplification stages include quantitative PCR reactions using a fluorescent reporter to indicate accumulation of a specific amplicon.

38. The method of claim 37, wherein the quantitative PCR reactions are fluorescent 5' nuclease assays.

39. The method of claim 37, wherein the fluorescent reporter is a molecular beacon.

40. The method of claim 18, wherein one or more reagents for the reaction mixture are provided for use in the reaction mixture in a cartridge suitably configured for use in an automated system.

41. The method of claim 40, wherein the cartridge is disposable after a single use.

42. The method of claim 40, wherein the cartridge contains additional reagents or mechanical components compartmentalized separately or together with the reagents for the reaction mixture, the additional reagents or mechanical components adapted for one of cell or tissue lysis, RNA purification and reverse transcription.

43. The method of claim 40, wherein the amplification stages include quantitative PCR reactions using a fluorescent reporter to indicate accumulation of a specific amplicon and the automated system automatically shifts the PCR reaction from the first amplification stage to the second amplification stage when the fluorescent reporter accumulates in the reaction mixture to a threshold level.

44. The method of claim 18, wherein the first and second stages are conducted sequentially in the same reaction vessel.

45. The method of claim 18, wherein there is expected to be at least about a 30–100-fold difference in the number of target sequences of the first primer set and of the second primer set in the DNA sample.

46. A multiplex, quantitative PCR method, comprising conducting a PCR amplification in a PCR reaction mixture in a first stage and a second stage, the reaction mixture comprising a DNA sample comprising a first nucleic acid species containing a first target amplification sequence and a second nucleic acid species different from the first nucleic acid species containing a second target amplification sequence, a first primer set for amplification of the first target amplification sequence and having a first effective Tm and a second primer set for amplification of the second target amplification sequence and having a second effective Tm different from the first effective Tm, each amplification stage comprising one or more PCR cycles, each PCR cycle comprising a denaturing step, an annealing step and an elongation step that may be conducted at the same temperature as the annealing step, wherein the annealing step of the first amplification stage is conducted at a different temperature than the annealing step of the second amplification stage to modulate the relative rate of production of a first amplicon by the first primer set and a second amplicon by the second primer set during the first and second amplification stages, thereby balancing the multiplex PCR amplification.

47. The method of claim 46, wherein the annealing step and the elongation step in a PCR cycle of at least one of the first amplification stage and the second amplification stage are conducted at the same temperature.

48. The method of claim 46, wherein the annealing step and the elongation step in PCR cycles of at least one of the first amplification stage and the second amplification stage are conducted at different temperatures.

49. The method of claim 46, wherein the effective Tm of the first primer set and the effective Tm of the second primer set differ by at least about 5° C.

50. The method of claim 46, wherein one of the first PCR primer set and the second PCR primer set produce one of a β-glucuronidase-specific amplicon, an 18S rRNA-specific amplicon, a carcinoembryonic antigen-specific amplicon and a tyrosinase-specific amplicon.

51. The method of claim 50, wherein one of the first PCR primer set and the second PCR primer set includes a primer comprising the sequence of one of SEQ ID NOS: 3, 4, 6, 7, 11, 12, 13, 14, 16, 17, 19 and 20.

52. The method of claim 50, wherein one of the first PCR primer set and the second PCR primer set includes a primer consisting of one of SEQ ID NOS: 3, 4, 6, 7, 11, 12, 13, 14, 16, 17, 19 and 20.

53. The method of claim 50, wherein the annealing step of the first amplification stage is conducted at a temperature greater than the annealing step of the second amplification stage.

54. The method of claim 53, wherein one of the first and second primer sets produces one of a β-glucuronidase-specific amplicon, a carcinoembryonic antigen-specific amplicon, an 18S rRNA amplicon and a tyrosinase amplicon.

55. The method of claim 53, wherein the first primer set produces a β-glucuronidase-specific amplicon and the second primer set produces a carcinoembryonic antigen-specific amplicon.

56. The method of claim 46, wherein the annealing step of the first amplification stage is conducted at a temperature less than the annealing step of the second amplification stage.

57. The method of claim 46, further comprising conducting a reverse transcription reaction on an RNA sample prior to the first amplification stage, and prior to the addition of one of PCR primers and a thermostable DNA polymerase to the reaction mixture, to produce DNA in the DNA sample of the reaction mixture.

58. The method of claim 57, wherein the reverse transcription reaction is conducted for less than about 10 minutes.

59. The method of claim 57, wherein the reverse transcription reaction is conducted for about 2 minutes.

60. The method of claim 57, wherein one or both of an Internal Positive Control RNA and an Internal Positive Control DNA is added to the reverse transcription reaction.

61. The method of claim 46, wherein an Internal Positive Control DNA is added to the PCR reaction mixture.

62. The method of claim 46, wherein the Internal Positive Control RNA comprises the sequence of one of SEQ ID NOS 23–25.

63. The method of claim 46, wherein one or more reagents for the reaction mixture are provided for use in the reaction mixture in a cartridge suitably configured for use in an automated system.

64. The method of claim 63, wherein the cartridge is disposable after a single use.

65. The method of claim 63, wherein the cartridge contains additional reagents or mechanical components compartmentalized separately or together with the reagents for the reaction mixture, the additional reagents or mechanical components adapted for one of cell or tissue lysis, RNA purification and reverse transcription.

66. The method of claim 46, wherein the amplification stages include one or more quantitative PCR reaction using a fluorescent reporter to indicate accumulation of a specific amplicon.

67. The method of claim 66, wherein the quantitative PCR reactions are fluorescent 5' nuclease assays.

68. The method of claim 66, wherein the fluorescent reporter is a molecular beacon.

69. An RT-PCR method, comprising:
  (a) conducting a reverse transcription reaction on an RNA sample in a reaction mixture to produce a DNA sample;
  (b) adding to the reaction mixture a first primer set having a first effective Tm, a second primer set having a second effective Tm different from the first effective Tm and a thermostable DNA polymerase; and
  (c) conducting a PCR amplification on the reaction mixture in a first amplification stage and a second amplification stage, each amplification stage comprising one or more PCR cycles and each PCR cycle comprises a denaturing step, an annealing step that may be conducted at the same temperature and the same time as the annealing step, wherein the annealing step of the first amplification stage is conducted at a lower temperature than the annealing step of the second amplification stage to modulate the relative rate of amplification of a first target sequence by the first primer set and a second target sequence by the second primer set during the first and second amplification stages, wherein first target sequence is expected to be at least about 30-fold more prevalent in the DNA sample than the second target sequence, and wherein:
  d) the RT reaction is conducted for less than about 10 minutes; or
  e) the denaturing step is conducted for about 1 second or less.

70. The method of claim 69, wherein the RT reaction is conducted for less than about 10 minutes, and, for one or both of the first and second amplification stages, the denaturing step is conducted for about 1 second or less, the annealing step is conducted for less than about 10 seconds and the elongation step is conducted for less than about 10 seconds.

* * * * *

SEQUENCE LISTING

<160> NUMBER OF SEQ ID NOS: 25

<210> SEQ ID NO 1
<211> LENGTH: 2975
<212> TYPE: DNA
<213> ORGANISM: Homo Sapiens

<400> SEQUENCE: 1

| | | | | | |
|---|---|---|---|---|---|
| ctcagggcag | agggaggaag | gacagcagac | cagacagtca | cagcagcctt | gacaaaacgt | 60 |
| tcctggaact | caagctcttc | tccacagagg | aggacagagc | agacagcaga | gaccatggag | 120 |
| tctccctcgg | cccctcccca | cagatggtgc | atccctggc | agaggctcct | gctcacagcc | 180 |
| tcacttctaa | ccttctggaa | cccgcccacc | actgccaagc | tcactattga | atccacgccg | 240 |
| ttcaatgtcg | cagaggggaa | ggaggtgctt | ctacttgtcc | acaatctgcc | ccagcatctt | 300 |
| tttggctaca | gctggtacaa | aggtgaaaga | gtggatggca | accgtcaaat | tataggatat | 360 |
| gtaataggaa | ctcaacaagc | taccccaggg | cccgcataca | gtggtcgaga | gataatatac | 420 |
| cccaatgcat | ccctgctgat | ccagaacatc | atccagaatg | acacaggatt | ctacacccta | 480 |
| cacgtcataa | agtcagatct | tgtgaatgaa | gaagcaactg | gccagttccg | ggtatacccg | 540 |
| gagctgccca | agccctccat | ctccagcaac | aactccaaac | ccgtggagga | caaggatgct | 600 |
| gtggccttca | cctgtgaacc | tgagactcag | gacgcaacct | acctgtggtg | ggtaaacaat | 660 |
| cagagcctcc | cggtcagtcc | caggctgcag | ctgtccaatg | gcaacaggac | cctcactcta | 720 |
| ttcaatgtca | caagaaatga | cacagcaagc | tacaaatgtg | aaacccagaa | cccagtgagt | 780 |
| gccaggcgca | gtgattcagt | catcctgaat | gtcctctatg | gcccggatgc | ccccaccatt | 840 |
| tcccctctaa | acacatctta | cagatcaggg | gaaaatctga | acctctcctg | ccacgcagcc | 900 |
| tctaacccac | ctgcacagta | ctcttggttt | gtcaatggga | cttttcagca | atccacccaa | 960 |
| gagctctttta | tccccaacat | cactgtgaat | aatagtggat | cctatacgtg | ccaagcccat | 1020 |
| aactcagaca | ctggcctcaa | taggaccaca | gtcacgacga | tcacagtcta | tgcagagcca | 1080 |
| cccaaaccct | tcatcaccag | caacaactcc | aaccccgtgg | aggatgagga | tgctgtagcc | 1140 |
| ttaacctgtg | aacctgagat | tcagaacaca | acctacctgt | ggtgggtaaa | taatcagagc | 1200 |
| ctcccggtca | gtcccaggct | gcagctgtcc | aatgacaaca | ggaccctcac | tctactcagt | 1260 |
| gtcacaagga | atgatgtagg | acccatatgag | tgtggaatcc | agaacaaatt | aagtgttgac | 1320 |
| cacagcgacc | cagtcatcct | gaatgtcctc | tatggcccag | acgacccac | catttccccc | 1380 |
| tcatacacct | attaccgtcc | agggtgaac | ctcagcctct | cctgccatgc | agcctctaac | 1440 |
| ccacctgcac | agtattcttg | gctgattgat | gggaacatcc | agcaacacac | acaagagctc | 1500 |
| tttatctcca | acatcactga | gaagaacagc | ggactctata | cctgccaggc | caataactca | 1560 |
| gccagtggcc | acagcaggac | tacagtcaag | acaatcacag | tctctgcgga | gctgccaag | 1620 |
| ccctccatct | ccagcaacaa | ctccaaaccc | gtggaggaca | aggatgctgt | ggccttcacc | 1680 |
| tgtgaacctg | aggctcagaa | cacaacctac | ctgtggtggg | taaatggtca | gagcctccca | 1740 |
| gtcagtccca | ggctgcagct | gtccaatggc | aacaggaccc | tcactctatt | caatgtcaca | 1800 |
| agaaatgacg | caagagccta | tgtatgtgga | atccagaact | cagtgagtgc | aaaccgcagt | 1860 |
| gacccagtca | ccctggatgt | cctctatggg | ccggacaccc | catcatttc | cccccagac | 1920 |
| tcgtcttacc | tttcgggagc | gaacctcaac | ctctcctgcc | actcggcctc | taacccatcc | 1980 |
| ccgcagtatt | cttggcgtat | caatgggata | ccgcagcaac | acacacaagt | tctctttatc | 2040 |

-continued

```
gccaaaatca cgccaaataa taacgggacc tatgcctgtt ttgtctctaa cttggctact    2100
ggccgcaata attccatagt caagagcatc acagtctctg catctggaac ttctcctggt    2160
ctctcagctg gggccactgt cggcatcatg attggagtgc tggttggggt tgctctgata    2220
tagcagccct ggtgtagttt cttcatttca ggaagactga cagttgtttt gcttcttcct    2280
taaagcattt gcaacagcta cagtctaaaa ttgcttcttt accaaggata tttacagaaa    2340
agactctgac cagagatcga gaccatccta gccaacatcg tgaaacccca tctctactaa    2400
aaatacaaaa atgagctggg cttggtggcg cgcacctgta gtcccagtta ctcgggaggc    2460
tgaggcagga gaatcgcttg aacccgggag gtggagattg cagtgagccc agatcgcacc    2520
actgcactcc agtctggcaa cagagcaaga ctccatctca aaagaaaag aaaagaagac    2580 tctgacctgt actcttgaat acaagtttct gataccactg cactgtctga gaatttccaa    2640
aactttaatg aactaactga cagcttcatg aaactgtcca ccaagatcaa gcagagaaaa    2700
taattaattt catgggacta aatgaactaa tgaggattgc tgattcttta aatgtcttgt    2760
ttcccagatt tcaggaaact tttttctttt taagctatcc acagcttaca gcaatttgat    2820
aaaatatact tttgtgaaca aaaattgaga catttacatt ttctccctat gtggtcgctc    2880
cagacttggg aaactattca tgaatattta tattgtatgg taatatagtt attgcacaag    2940
ttcaataaaa atctgctctt tgtatgacag aatac                              2975
```

<210> SEQ ID NO 2
<211> LENGTH: 20
<212> TYPE: DNA
<213> ORGANISM: Artificial Sequence
<220> FEATURE:
<223> OTHER INFORMATION: B-gus RT primer

<400> SEQUENCE: 2
tttggttgtc tctgccgagt                                                20

<210> SEQ ID NO 3
<211> LENGTH: 22
<212> TYPE: DNA
<213> ORGANISM: Artificial Sequence
<220> FEATURE:
<223> OTHER INFORMATION: B-gus forward PCR primer

<400> SEQUENCE: 3
ctcatttgga attttgccga tt                                             22

<210> SEQ ID NO 4
<211> LENGTH: 22
<212> TYPE: DNA
<213> ORGANISM: Artificial Sequence
<220> FEATURE:
<223> OTHER INFORMATION: B-gus Reverse PCR primer

<400> SEQUENCE: 4
ccgagtgaag atccccttttt ta                                            22

<210> SEQ ID NO 5
<211> LENGTH: 26
<212> TYPE: DNA
<213> ORGANISM: Artificial Sequence
<220> FEATURE:
<223> OTHER INFORMATION: B-gus taqman probe

<400> SEQUENCE: 5

-continued

| | |
|---|---|
| tgaacagtca ccgacgagag tgctgg | 26 |

<210> SEQ ID NO 6
<211> LENGTH: 22
<212> TYPE: DNA
<213> ORGANISM: Artificial Sequence
<220> FEATURE:
<223> OTHER INFORMATION: CEA Forward PCR primer

<400> SEQUENCE: 6

| | |
|---|---|
| agacaatcac agtctctgcg ga | 22 |

<210> SEQ ID NO 7
<211> LENGTH: 20
<212> TYPE: DNA
<213> ORGANISM: Artificial Sequence
<220> FEATURE:
<223> OTHER INFORMATION: CEA Reverse PCR Primer

<400> SEQUENCE: 7

| | |
|---|---|
| atccttgtcc tccacgggtt | 20 |

<210> SEQ ID NO 8
<211> LENGTH: 26
<212> TYPE: DNA
<213> ORGANISM: Artificial Sequence
<220> FEATURE:
<223> OTHER INFORMATION: CEA Taqman probe

<400> SEQUENCE: 8

| | |
|---|---|
| caagccctcc atctccagca acaact | 26 |

<210> SEQ ID NO 9
<211> LENGTH: 16
<212> TYPE: DNA
<213> ORGANISM: Artificial Sequence
<220> FEATURE:
<223> OTHER INFORMATION: CEA RT primer

<400> SEQUENCE: 9

| | |
|---|---|
| gtgaaggcca cagcat | 16 |

<210> SEQ ID NO 10
<211> LENGTH: 22
<212> TYPE: DNA
<213> ORGANISM: Artificial Sequence
<220> FEATURE:
<223> OTHER INFORMATION: 18SrRNS Taqman probe

<400> SEQUENCE: 10

| | |
|---|---|
| tgctggcacc agacttgccc tc | 22 |

<210> SEQ ID NO 11
<211> LENGTH: 23
<212> TYPE: DNA
<213> ORGANISM: Artificial Sequence
<220> FEATURE:
<223> OTHER INFORMATION: 18SrRNA forward PCR primer

<400> SEQUENCE: 11

| | |
|---|---|
| ccctgtaatt ggaatgagtc cac | 23 |

<210> SEQ ID NO 12
<211> LENGTH: 18
<212> TYPE: DNA
<213> ORGANISM: Artificial Sequence -continued

```
<220> FEATURE:
<223> OTHER INFORMATION: 18SrRNA Reverse PCR primer

<400> SEQUENCE: 12
gctggaatta ccgcggct                                                 18

<210> SEQ ID NO 13
<211> LENGTH: 19
<212> TYPE: DNA
<213> ORGANISM: Artificial Sequence
<220> FEATURE:
<223> OTHER INFORMATION: 18SrRNA Forward - low temp -PCR primer

<400> SEQUENCE: 13
ccctgtaatt ggaatgagt                                                19

<210> SEQ ID NO 14
<211> LENGTH: 15
<212> TYPE: DNA
<213> ORGANISM: Artificial Sequence
<220> FEATURE:
<223> OTHER INFORMATION: 18SrRNA Reverse - low temp PCR primer

<400> SEQUENCE: 14
gctggaatta ccgcg                                                    15

<210> SEQ ID NO 15
<211> LENGTH: 16
<212> TYPE: DNA
<213> ORGANISM: Artificial Sequence
<220> FEATURE:
<223> OTHER INFORMATION: B-gus RT primer

<400> SEQUENCE: 15
tggttgtctc tgccga                                                   16

<210> SEQ ID NO 16
<211> LENGTH: 18
<212> TYPE: DNA
<213> ORGANISM: Artificial Sequence
<220> FEATURE:
<223> OTHER INFORMATION: B-gus Forward PCR Primer - low temp

<400> SEQUENCE: 16
ctcatttgga attttgcc                                                 18

<210> SEQ ID NO 17
<211> LENGTH: 17
<212> TYPE: DNA
<213> ORGANISM: Artificial Sequence
<220> FEATURE:
<223> OTHER INFORMATION: B-gus Reverse Primer - Low temp

<400> SEQUENCE: 17
cgagtgaaga tcccctt                                                  17

<210> SEQ ID NO 18
<211> LENGTH: 15
<212> TYPE: DNA
<213> ORGANISM: Artificial Sequence
<220> FEATURE:
<223> OTHER INFORMATION: CEA taqman probe
<221> NAME/KEY: misc_feature
<222> LOCATION: (15)..(15)
<223> OTHER INFORMATION: Uracil residue
<221> NAME/KEY: misc_feature
<222> LOCATION: (4)..(4)
```

<223> OTHER INFORMATION: Uracil residue

<400> SEQUENCE: 18
agcngcccaa gcccn                                                     15

<210> SEQ ID NO 19
<211> LENGTH: 23
<212> TYPE: DNA
<213> ORGANISM: Artificial Sequence
<220> FEATURE:
<223> OTHER INFORMATION: Tyrosinase Forward PCR primer

<400> SEQUENCE: 19
acttactcag cccagcatca ttc                                            23

<210> SEQ ID NO 20
<211> LENGTH: 23
<212> TYPE: DNA
<213> ORGANISM: Artificial Sequence
<220> FEATURE:
<223> OTHER INFORMATION: Tyrosinase Reverse PCR Primer

<400> SEQUENCE: 20
actgatggct gttgtactcc tcc                                            23

<210> SEQ ID NO 21
<211> LENGTH: 29
<212> TYPE: DNA
<213> ORGANISM: Artificial Sequence
<220> FEATURE:
<223> OTHER INFORMATION: Tyrosinase Taqman probe

<400> SEQUENCE: 21
tctcctcttg gcagattgtc tgtagccga                                      29

<210> SEQ ID NO 22
<211> LENGTH: 17
<212> TYPE: DNA
<213> ORGANISM: Artificial Sequence
<220> FEATURE:
<223> OTHER INFORMATION: Tyrosinase RT primer

<400> SEQUENCE: 22
cgttccattg cataaag                                                   17

<210> SEQ ID NO 23
<211> LENGTH: 28
<212> TYPE: DNA
<213> ORGANISM: Artificial Sequence
<220> FEATURE:
<223> OTHER INFORMATION: Internal control probe

<400> SEQUENCE: 23
agcatcatcc tctgcatggt caggtcat                                       28

<210> SEQ ID NO 24
<211> LENGTH: 77
<212> TYPE: DNA
<213> ORGANISM: Artificial Sequence
<220> FEATURE:
<223> OTHER INFORMATION: CEA mimic - Internal Control

<400> SEQUENCE: 24
agacaatcac agtctctgcg gaagcatcat cctctgcatg gtcaggtcat aactccaaac    60
ccgtggagga caaggat                                                   77

```
<210> SEQ ID NO 25
<211> LENGTH: 77
<212> TYPE: DNA
<213> ORGANISM: Artificial Sequence
<220> FEATURE:
<223> OTHER INFORMATION: Tyrosinase mimic - Internal Control Probe
<221> NAME/KEY: misc_feature
<222> LOCATION: (7)..(7)
<223> OTHER INFORMATION: Uracil residue
<221> NAME/KEY: misc_feature
<222> LOCATION: (18)..(18)
<223> OTHER INFORMATION: Uracil residue
<221> NAME/KEY: misc_feature
<222> LOCATION: (62)..(62)
<223> OTHER INFORMATION: Uracil residue
<221> NAME/KEY: misc_feature
<222> LOCATION: (73)..(73)
<223> OTHER INFORMATION: Uracil residue

<400> SEQUENCE: 25
acttacncag cccagcanca ttctagcatc atcctctgca tggtcaggtc atttggagga        60
gnacaacagc cancagt                                                      77
```